(12) United States Patent
Lacrampe et al.

(10) Patent No.: US 6,911,444 B2
(45) Date of Patent: Jun. 28, 2005

(54) NON-STEROIDAL IL-5 INHIBITORS, PROCESSES AND INTERMEDIATES FOR THEIR PREPARATION AND PHARMACEUTICAL COMPOSITIONS COMPRISING SAID INHIBITORS

(75) Inventors: Jean Fernand Armand Lacrampe, Le Mesnil Esnard (FR); Eddy Jean Edgard Freyne, Rumst (BE); Frederik Dirk Deroose, Drongen (BE); Jérôme Michel Claude Fortin, Lery (FR); Erwin Coesemans, Nijlen (BE)

(73) Assignee: Janssen Pharmaceutics N.V., Beerse (BE)

( * ) Notice: Subject to any disclaimer, the term of this patent is extended or adjusted under 35 U.S.C. 154(b) by 64 days.

(21) Appl. No.: 10/075,876

(22) Filed: Feb. 14, 2002

(65) Prior Publication Data

US 2003/0114453 A1 Jun. 19, 2003

Related U.S. Application Data

(63) Continuation-in-part of application No. 10/049,038, filed as application No. PCT/EP00/07358 on Jul. 31, 2000, now abandoned.

(30) Foreign Application Priority Data

Aug. 6, 1999 (EP) .............................. 99870170
Dec. 27, 1999 (EP) ............................ 99126035

(51) Int. Cl.$^7$ ................. C07D 253/075; C07D 417/10; A61K 31/53; A61P 37/08
(52) U.S. Cl. ...................................... 514/242; 544/182
(58) Field of Search .......................... 544/182; 514/242

(56) References Cited

U.S. PATENT DOCUMENTS

| 4,631,278 A | 12/1986 | Boeckx et al. |
| 2002/0010177 A1 | 1/2002 | Freyne et al. |
| 2002/0042416 A1 | 4/2002 | Freyne et al. |

FOREIGN PATENT DOCUMENTS

| EP | 0170316 B1 | 5/1990 |
| EP | 0232932 B1 | 1/1991 |
| EP | 0987265 A1 * | 3/2000 |
| FR | 2 532 313 A2 | 2/1984 |
| WO | WO 99/02504 A1 | 1/1999 |
| WO | WO 99/02505 A1 | 1/1999 |

OTHER PUBLICATIONS

Wang–Lin, Y., et al., "Synthesis of 1,4–bis(1,3, 4–oxadiazol–2–yl)–2,5–dialkoxybenzene–oligothiophene copolymers with different emissive colors: synthetically tuning the photoluminescence of conjugated polymers." *Chemical Comm.* 1957, pp. 1957–1958.

Buzas, A., et al., CAPLUS Accession No. 1961:131401, Chemical Abstract, 1961, vol. 55, Abstract # 131,401.

Peet, N.P., et al., "Synthesis of a Novel indolobenzodiazepine." *J. Heterocyclic Chem.*, 1983, pp. 1355–1357, vol. 20.

Carr, M. W. et al., "Monocyte chemoattractant protein 1 acts as a T–lymphocyte chemoattractant.". *Proc. Natl. Acad. Sci.* 1994, 91, 3652–3656.

Baggiolini, M., et al., CC chemokines in allergic inflammation, *Immunology Today*, 1994, 15(3), 127–133.

PCT International Search Report PCT/EP00/07358 dated Jan. 25, 2001, which relates to U.S. Appl. 10/075,876.

Published Application for U.S. Patent 2002/0010177 (A1), which relates in family to EP 0987265, and a MicroPatent® Family Lookup.

Office Action received in U.S. Appl. No. 10/049,038 to which U.S. Appl. No. 10/075,876 claims priority as a continuation–in–part thereof.

Published Application for U.S. Patent 20020042416 (A1), and a MicroPatent® Family Lookup.

* cited by examiner

Primary Examiner—Richard L. Raymond
Assistant Examiner—Venkataraman Balasubramanian
(74) Attorney, Agent, or Firm—Alana G. Kriegsman; Gabriel Lopez

(57) ABSTRACT

The present invention relates to IL-5 inhibiting 6-azauracil derivatives useful for treating eosinophil-dependent inflammatory diseases, to processes and intermediates for their preparation as well as to pharmaceutical compositions comprising the said derivatives. It further relates to the use of such derivatives as a medicine, and to processes for marking a receptor or imaging an organ using the said derivatives.

13 Claims, No Drawings

NON-STEROIDAL IL-5 INHIBITORS, PROCESSES AND INTERMEDIATES FOR THEIR PREPARATION AND PHARMACEUTICAL COMPOSITIONS COMPRISING SAID INHIBITORS

CROSS REFERENCE TO RELATED APPLICATIONS

This application is a continuation-in-part application of Ser. No. 10/049,038, filed Feb. 5, 2002, abandoned, which is a 371 of PCT/EP00/107358, filed Jul. 31, 2000, which application claims priority from EP 99870170.0, filed Aug. 6, 1999, and EP 99126035.7, filed Dec. 27, 1999.

The present invention relates to IL-5 inhibiting 6-azauracil derivatives useful for treating eosinophil-dependent inflammatory diseases, to processes and intermediates for their preparation as well as to pharmaceutical compositions comprising the said derivatives. It further relates to the use of such derivatives as a medicine, and to processes for marking a receptor or imaging an organ using the said derivatives.

Eosinophil influx, leading to subsequent tissue damage, is an important pathogenic event in bronchial asthma and allergic diseases. The cytokine interleukin-5 (IL-5), produced mainly by T lymphocytes as a glycoprotein, induces the differentiation of eosinophils in bone marrow and, primes eosinophils for activation in peripheral blood and sustains their survival in tissues. As such, IL-5 plays a critical role in the process of eosinophilic inflammation. Hence, the possibility that inhibitors of IL-5 production would reduce the production, activation and/or survival of eosinophils provides a therapeutic approach to the treatment of bronchial asthma and allergic diseases such as, atopic dermatitis, allergic rhinitis, allergic conjunctivitis, and also other eosinophil-dependent inflammatory diseases.

Steroids, which strongly inhibit IL-5 production in vitro, have long been used as the only drugs with remarkable efficacy for bronchial asthma and atopic dermatitis, but they cause various serious adverse reactions such as diabetes, hypertension and cataracts. Therefore, it would be desirable to find non-steroidal compounds having the ability to inhibit IL-5 production in human T-cells and which have little or no adverse reactions.

U.S. Pat. No. 4,631,278 discloses α-aryl-4-(4,5-dihydro-3,5-dioxo-1,2,4-triazin-2(3H)-yl)-benzene-acetonitriles and U.S. Pat. No. 4,767,760 discloses 2-(substituted phenyl)-1,2,4-triazine-3,5(2H,4H)-diones, all having anti-protozoal activity, in particular, anti-coccidial activity. EP 831,088 discloses 1,2,4-triazine-3,5-diones as anticoccidial agents. WO99/02505 discloses 6-azauracil derivatives which prove to be potent inhibitors of the production of IL-5.

The present invention first relates to compounds having the formula:

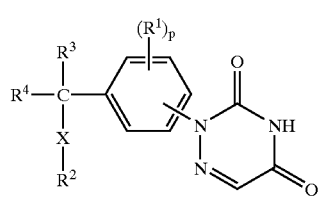

(I)

the N-oxides, the pharmaceutically acceptable addition salts and the stereochemically isomeric forms thereof, wherein:
p represents an integer being 0, 1, 2, 3 or 4;

X represents O, S, $NR^5$ or a direct bond or —X—$R^2$ taken together may represent cyano;
Y represents O, S, $NR^5$, or $S(O)_2$;
each R independently represents $C(=O)\cdot Z—R^{14}$, $C_{1-6}$alkyl, halo, polyhalo$C_{1-6}$alkyl, hydroxy, mercapto, $C_{1-6}$alkyloxy, $C_{1-6}$alkylthio, $C_{1-6}$alkylcarbonyloxy, aryl, cyano, nitro, $Het^3$, $R^6$, $NR^7R^8$ or $C_{1-4}$alkyl substituted with $C(=O)—Z\cdot R^{14}$, $Het^3$, $R^6$ or $NR^7R^8$;
$R^2$ represents $Het^1$, $C_{3-7}$cycloalkyl optionally substituted with $C(=O)—Z—R^{14}$, $C_{1-6}$alkyl or $C_{1-6}$alkyl substituted with one or two substituents selected from $C(=O)\cdot Z—R^{14}$, hydroxy, mercapto, cyano, amino, mono- or di($C_{1-4}$alkyl)amino, $C_{1-6}$alkyloxy optionally substituted with $C(=O)—Z—R^{14}$, $C_{1-6}$alkylthio optionally substituted with $C(=O)—Z—R^{14}$, $C_{1-6}$alkylsulfonyloxy, $C_{3-7}$cycloalkyl optionally substituted with $C(=O)—Z—R^{14}$, aryl, aryloxy, arylthio, $Het^1$, $Het^1$oxy and $Het^1$thio; and if X is O, S or $NR^5$, then $R^2$ may also represent aminothiocarbonyl, $C_{1-4}$alkylcarbonyl optionally substituted with $C(=O)—Z—R^{14}$, $C_{1-4}$alkylthiocarbonyl optionally substituted with $C(=O)—Z—R^{14}$, arylcarbonyl, arylthiocarbonyl, $Het^1$carbonyl or $Het^1$thiocarbonyl;
$R^3$ represents hydrogen, $C_{1-6}$alkyl or $C_{3-7}$cycloalkyl;
$R^4$ represents hydrogen, $C_{1-6}$alkyl or $C_{3-7}$cycloalkyl; or
$R^3$ and $R^4$ taken together form a $C_{2-6}$alkanediyl;
$R^5$ represents hydrogen or $C_{1-4}$alkyl;
each $R^6$ independently represents $C_{1-6}$alkylsulfonyl, aminosulfonyl, piperidinylsulfonyl, mono- or di($C_{1-4}$alkyl)aminosulfonyl, mono- or di(benzyl)aminosulfonyl, polyhalo$C_{1-6}$alkylsulfonyl, $C_{1-6}$alkylsulfinyl, phenyl$C_{1-4}$alkylsulfonyl, piperazinylsulfonyl, aminopiperidinylsulfonyl, piperidinyl-aminosulfonyl, N—$C_{1-4}$alkyl-N-piperidinylaminosulfonyl, Y—$R^{14}$, mono- or di-($C_{1-4}$alkyl)amino$C_{1-4}$alkylsulfonyl, $Het^6$sulfonyl or $C_{3-7}$ cycloalkylsulfonyl;
each $R^7$ and each $R^8$ are independently selected from hydrogen, $C_{1-4}$alkyl, hydroxy$C_{1-4}$alkyl, mercapto-$C_{1-4}$alkyl, dihydroxy$C_{1-4}$alkyl, aryl, aryl$C_{1-4}$alkyl, $C_{1-4}$alkyloxy$C_{1-4}$alkyl, $C_{1-4}$alkylcarbonyl, $C_{1-4}$alkyl-thiocarbonyl, arylcarbonyl, arylthiocarbonyl, $Het^3$thiocarbonyl, $Het^3$carbonyl, mono- or di($C_{1-4}$alkyl)amino$C_{1-4}$alkyl, arylaminocarbonyl, arylaminothiocarbonyl, $Het^3$aminocarbonyl, $Het^3$aminothiocarbonyl, $C_{3-7}$cycloalkyl, pyridinyl$C_{1-4}$alkyl, $C_{1-4}$alkanediyl-C(=O)—Z—$R^{14}$, —C(=O)—Z—$R^{14}$, —Y—$C_{1-4}$alkanediyl-C(=O)—Z—$R^{14}$, $Het^3$, $Het^4$ and $R^6$; or $R^7$ and $R^8$ taken together with the nitrogen atom to which they are attached form a radical of formula

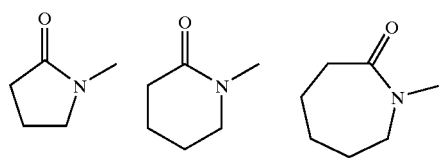

$R^9$ and $R^{10}$ are each independently selected from hydrogen, $C_{1-4}$alkyl, hydroxy$C_{1-4}$alkyl, mercapto-$C_{1-4}$alkyl, dihydroxy$C_{1-4}$alkyl, phenyl, phenyl$C_{1-4}$alkyl, $C_{1-4}$alkyloxy$C_{1-4}$alkyl, $C_{1-4}$alkylcarbonyl, arylcarbonyl, $Het^3$carbonyl, $Het^3$thiocarbonyl, mono- or di($C_{1-4}$alkyl)amino$C_{1-4}$alkyl, arylaminocarbonyl, arylaminothiocarbonyl, $Het^3$aminocarbonyl, $Het^3$aminothiocarbonyl, $C_{3-7}$cycloalkyl, pyridinyl$C_{1-4}$alkyl, $C_{1-4}$alkanediyl-C(=O)—Z—$R^{14}$, —C(=O)—Z—$R^{14}$, —Y—$C_{1-4}$alkanediyl-C(=O)—Z—$R^{14}$, $Het^3$, $Het^4$ and $R^6$;

or $R^9$ and $R^{10}$ taken together with the nitrogen atom to which they are attached form a radical of formula

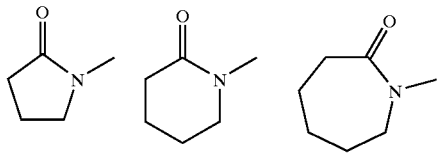

each $R^{11}$ independently being selected from hydroxy, mercapto, cyano, nitro, halo, trihalomethyl, $C_{1-4}$alkyloxy optionally substituted with $C(=O)$—Z—$R^{14}$, $C_{1-6}$alkylthio optionally substituted with $C(=O)$—Z—$R^{14}$, formyl, trihalo$C_{1-4}$alkylsulfonyloxy, $R^6$, $NR^7R^8$, $C(=O)NR^{15}R^{16}$, —$C(=O)$—Z—$R^{14}$—Y—$C_{1-4}$alkanediyl-$C(=O)$—Z—$R^{14}$, aryl, aryloxy, arylcarbonyl, arylthiocarbonyl, $C_{3-7}$cycloalkyl optionally substituted with $C(=O)$—Z—$R^{14}$, $C_{3-7}$cycloalkyloxy optionally substituted with $C(=O)$—Z—$R^{14}$, $C_{3-7}$cycloalkylthio optionally substituted with $C(=O)$—Z—$R^{14}$, phthalimide-2-yl, H Het$^4$, $C(=O)$Het$^3$, $C(=O)C_{1-4}$alkyl optionally be substituted with one or more substituents independently selected from hydroxy, mercapto, halo and phenyl;

$R^{12}$ and $R^{13}$ are each independently selected from hydrogen, $C_{1-4}$alkyl, hydroxy$C_{1-4}$alkyl, mercapto-$C_{1-4}$alkyl, dihydroxy$C_{1-4}$alkyl, phenyl, phenyl-$C_{1-4}$alkyl, $C_{1-4}$alkyloxy$C_{1-4}$alkyl, $C_{1-4}$alkylcarbonyl, $C_{1-4}$alkylthiocarbonyl, arylcarbonyl, mono- or di($C_{1-4}$alkyl)amino$C_{1-4}$alkyl, arylaminocarbonyl, arylaminothiocarbonyl, $C_{3-7}$cycloalkyl, pyridinyl$C_{1-4}$alkyl, $C_{1-4}$alkanediyl-$C(=O)$—Z—$R^{14}$, —$C(=O)$—Z—$R^{14}$, —Y—$C_{1-4}$alkanediyl-$C(=O)$—Z—$R^{14}$ and $R^6$; or $R^{12}$ and $R^{13}$ taken together with the nitrogen atom to which they are attached form a radical of formula

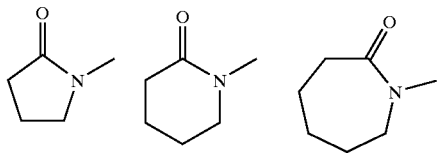

each $R^{14}$ independently represents hydrogen; $C_{1-20}$acyl or $C_{1-20}$alkyl$C_{1-20}$acyl (having a straight or branched, saturated or unsaturated hydrocarbon chain having 1 to 20 carbon atoms) optionally substituted with one or more substituents selected from hydroxy, mercapto, hydroxy$C_{1-4}$alkyl, mercapto-$C_{1-4}$alkyl, $NR^{17}R^{18}$, aryl, mono- or di-($C_{1-4}$alkyl)amino, cyano and Het$^5$; $C_{1-20}$alkyl optionally substituted with one or more substituents selected from hydroxy, halo, mercapto, $C_{1-4}$alkyloxy$C_{1-4}$alkyloxy, mercapto$C_{1-4}$alkyl, $NR^{17}R^{18}$, aryl, mono- or di-($C_{1-4}$alkyl)amino, cyano, Het$^5$, $C_{1-4}$alkyloxycarbonyl, aryl$C_{1-4}$alkyloxycarbonyl, aryl$C_{1-4}$alkyloxy, aryl$C_{1-4}$alkylthiocarbonyl, aryl$C_{1-4}$alkylthio, Het$^5C_{1-4}$alkyloxy, aryl$C_{1-4}$alkylthio, $C_{3-7}$ cycloalkyl and Het$^5C_{1-4}$alkylthio; $C_{3-20}$alkenyl optionally substituted with phenyl; $C_{3-20}$alkynyl; $C_{3-7}$ cycloalkyl optionally substituted with one or more substituents selected from hydroxy, mercapto, halo, mercapto$C_{1-4}$alkyl and hydroxy$C_{1-4}$alkyl; Het$^5$ or phenyl or $R^{14}$ represents a radical having any of the following formulae:

(a) 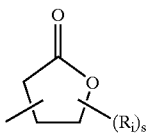

(b) 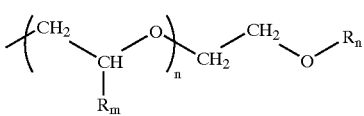

(c) 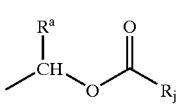

(d) 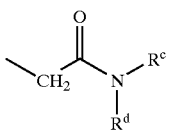

(e) 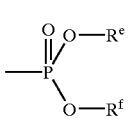

(h) 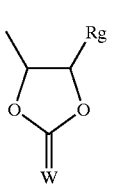

(i) 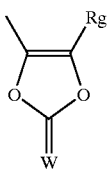

(j) 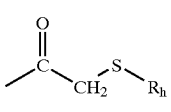

(k) 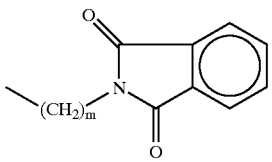

(l) 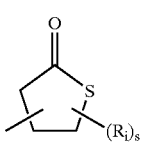

(m) 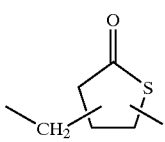

-continued

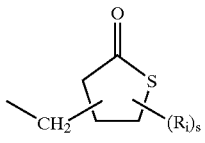 (n)

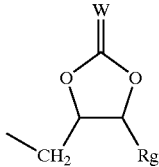 (o)

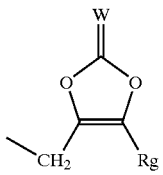 (p)

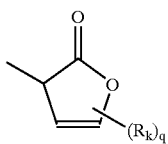 (q)

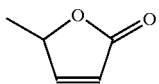 (r)

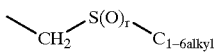 (s)

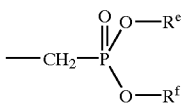 (t)

wherein m is 1 to 4, n is 0 to 5, q is 0 to 2, r is 0 to 2 and s is 0 to 4;

$R^b$ is selected from hydrogen, $C_{1-6}$alkyl, phenyl, $C_{3-7}$cycloalkyl, $C_{1-4}$ alkyloxy$C_{1-6}$alkyl and $C_{1-4}$ alkyl-Y—$C_{1-4}$alkyl;

$R^a$, $R^c$, $R^d$, $R^e$ and $R^f$ are each independently selected from hydrogen, $C_{1-6}$alkyl, phenyl and $C_{3-7}$cycloalkyl, or $R^e$ and $R^f$ taken together may form —CH$_2$—CH$_2$—, —CH$_2$—CH$_2$—CH$_2$— or —CH$_2$—CH$_2$—CH$_2$—CH$_2$—;

$R_g$, $R_h$ and $R_k$ are each independently hydrogen or $C_{1-4}$ alkyl;

$R_i$ is selected from hydroxy, $C_{3-7}$cycloalkyl and $C_{1-4}$alkyl, or two $R_i$ taken together may form —CH$_2$—CH$_2$—, —CH$_2$—CH$_2$—CH$_2$— or —CH$_2$—CH$_2$—CH$_2$—CH$_2$— (thus building a spiro radical);

$R_j$ is selected from —O—$R_b$; $C_{1-6}$alkyl optionally substituted with phenyl or $C_{3-7}$cycloalkyl; phenyl; $C_{3-7}$cycloalkyl optionally substituted with $C_{1-4}$ alkyloxy and mono- or di($C_{1-4}$alkyl)amino;

$R_m$ is hydrogen or $C_{1-4}$ alkyloxy;

$R_n$ is hydrogen, $C_{1-4}$alkyl, $C_{3-7}$cycloalkyl, phenyl or phenyl$C_{1-4}$alkyl; and W represents O or S;

each Z independently represents O, S, NH, —CH$_2$—O— or —CH$_2$—S— whereby —CH$_2$— is attached to the carbonyl group; or —Z—$R^{14}$ taken together form a radical of formula

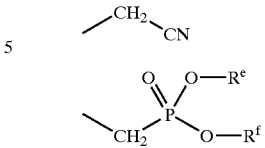 (f)

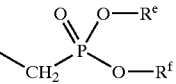 (g)

$R^{15}$ and $R^{15}$ are each independently selected from hydrogen; $C_{1-4}$alkyl optionally substituted with one or more substituents independently selected from hydroxy, mercapto, aryl, mono- or di($C_{1-4}$alkyl) amino and pyridinyl; $C_{1-4}$alkyloxy; aryl; —C(=O)—Z—$R^{14}$; arylcarbonyl; arylthiocarbonyl; arylaminocarbonyl; arylaminothiocarbonyl; aminocarbonylmethylene; mono- or di($C_{1-4}$alkyl) aminocarbonylmethylene; Het$^3$aminocarbonyl; Het$^3$aminothio-carbonyl; pyridinyl$C_{1-4}$alkyl; Het$^3$ and $R^6$; or $R^{15}$ and $R^{16}$ taken together with the nitrogen atom to which they are attached form a radical of formula

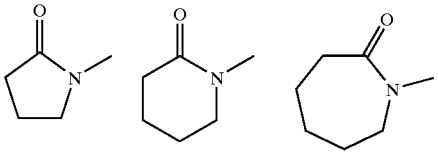

$R^{17}$ and $R^{13}$ are each independently selected from hydrogen, $C_{1-6}$alkyl optionally substituted with one or more substituents independently selected from hydroxy, mercapto, aryl, mono- or di($C_{1-4}$alkyl) amino, $C_{1-4}$ alkyloxy and pyridinyl; $C_{1-4}$alkyloxycarbonyl; aryl; $C_{1-4}$alkylcarbonyl; $C_{1-4}$alkylthiocarbonyl; arylcarbonyl; arylthiocarbonyl; arylaminocarbonyl; arylaminothiocarbonyl; $C_{3-7}$cycloalkyl; $C_{1-4}$alkane-diyl-C(=O)—Z—$C_{1-6}$alkyl; —C(=O)—Z—$C_{1-6}$alkyl;

—Y—$C_{1-4}$alkanediyl-C(=O)—Z—$C_{1-6}$alkyl and $R^6$;

aryl represents phenyl optionally substituted with one, two or three substituents each independently selected from nitro, azido, cyano, halo, hydroxy, mercapto, $C_{1-4}$alkyl, $C_{3-7}$cycloalkyl, $C_{1-4}$alkyloxy, $C_{1-4}$alkylthio, formyl, polyhalo$C_{1-4}$alkyl, NR$^9$R$^{10}$, C(=O)NR$^9$R$^{10}$, C(=O)—Z—$R^{14}$, $R^6$, —O—$R^6$, phenyl, Het$^3$, C(=O)Het$^3$ and $C_{1-4}$alkyl substituted with one or more substituents each independently selected from halo, hydroxy, mercapto, $C_{1-4}$alkyloxy, $C_{1-4}$alkylthio, C(=O)—Z—$R^{14}$, —Y—$C_{1-4}$alkanediyl-C(=O)—Z—$R^{14}$, Het$^3$ or NR$^9$R$^{10}$;

Het$^1$ represents a three-membered, four-membered, five-membered or six-membered aromatic or non-aromatic, monocyclic or polycyclic heterocycle comprising one or more, preferably one to four, heteroatoms, preferably selected from nitrogen, oxygen, sulfur and phosphorus, or a fused polycyclic ring system including such heterocycle (such as for instance a fused benzoheterocycle); non-limiting examples of such heterocycles include for instance pyrrolyl, pyrrolinyl, imidazolyl, imidazolinyl, pyrazolyl, pyrazolinyl, triazolyl, tetrazolyl, furanyl, tetrahydrofuranyl, thienyl, thiolanyl, dioxolanyl, oxazolyl, oxazolinyl, isoxazolyl, thiazolyl, thiazolinyl, isothiazolyl, thiadiazolyl, oxadiazolyl, pyridinyl, pyrimidinyl, pyrazinyl, pyranyl, pyridazinyl, pyrrolidinyl, piperidinyl, piperazinyl, morpholinyl, thiomorpholinyl, dioxanyl, dithianyl, trithianyl, triazinyl, benzothienyl, isobenzothienyl, benzofuranyl, isobenzofuranyl, benzothiazolyl, benzoxazolyl, benzodioxanyl, indolyl, isoindolyl, indolinyl, purinyl, 1H-pyrazolo[3,4-d]pyrimidinyl, benzimidazolyl, quinolyl, isoquinolyl, cinnolinyl, phtalazinyl, quinazolinyl, quinoxalinyl, thiazolopyridinyl, oxazolopyridinyl and imidazo[2,1-b]thiazolyl; wherein said heterocycles each independently may optionally be substituted with one, or where possible, two or three substituents each independently selected from Het$^2$, R$^{11}$ and C$_{1-4}$alkyl optionally substituted with one or, where possible, two or three substituents each independently selected from Het$^2$ and R$^{11}$;

Het$^2$ represents a three-membered, four-membered, five-membered or six-membered aromatic or non-aromatic, monocyclic or polycyclic heterocycle comprising one or more, preferably one to four, heteroatoms, preferably selected from nitrogen, oxygen, sulfur and phosphorus, or a fused polycyclic ring system including such heterocycle (such as for instance a fused benzoheterocycle); non-limiting examples of such heterocycles include for instance pyrrolyl, pyrrolinyl, imidazolyl, imidazolinyl, pyrazolyl, pyrazolinyl, triazolyl, tetrazolyl, furanyl, tetrahydrofuranyl, thienyl, thiolanyl, dioxolanyl, oxazolyl, oxazolinyl, isoxazolyl, thiazolyl, thiazolinyl, isothiazolyl, thiadiazolyl, oxadiazolyl, pyridinyl, pyrimidinyl, pyrazinyl, pyranyl, pyridazinyl, dioxanyl, dithianyl, trithianyl, triazinyl, benzothienyl, isobenzothienyl, benzofuranyl, isobenzofuranyl, benzothiazolyl, benzoxazolyl, indolyl, isoindolyl, indolinyl, purinyl, 1H-pyrazolo[3,4-d]pyrimidinyl, benzimidazolyl, quinolyl, isoquinolyl, cinnolinyl, phtalazinyl, quinazolinyl, quinoxalinyl, thiazolopyridinyl, oxazolopyridinyl and imidazo[2,1-b]thiazolyl; wherein said heterocycles each independently may optionally be substituted with one, or where possible, two or three substituents each independently selected from Het$^4$, R$^{11}$ and C$_{1-4}$alkyl optionally substituted with one or, where possible, two or three substituents each independently selected from Het$^4$ and R$^{11}$;

Het$^3$ represents a three-membered, four-membered, five-membered or six-membered aromatic or non-aromatic monocyclic heterocycle comprising one or more, preferably one to four, heteroatoms, preferably selected from nitrogen, oxygen, sulfur and phosphorus; non-limiting examples of such heterocycles include for instance pyrrolidinyl, piperidinyl, piperazinyl, morpholinyl, thiomorpholinyl, dioxolanyl and tetrahydropyranyl; wherein said monocyclic heterocycles each independently may optionally be substituted with, where possible, one, two, three or four substituents each independently selected from hydroxy, C$_{1-4}$alkyl, C$_{1-4}$alkyloxy, C$_{1-4}$alkylcarbonyl, piperidinyl, NR$^{12}$R$^{13}$, C(=O)—Z—R$^{14}$, R$^6$ and C$_{1-4}$alkyl substituted with one or two substituents independently selected from hydroxy, carbonyl C$_{1-4}$alkyloxy, phenyl, C(=O)—Z—R$^{14}$, —Y—C$_{1-4}$alkanediyl-C(=O)—Z—R$^{14}$, R$^6$ and NR$^{12}$R$^{13}$;

Het$^4$ represents a three-membered, four-membered, five-membered or six-membered aromatic or non-aromatic monocyclic heterocycle comprising one or more, preferably one to four, heteroatoms, preferably selected from nitrogen, oxygen, sulfur and phosphorus; non-limiting examples of such heterocycles include for instance pyrrolyl, imidazolyl, pyrazolyl, triazolyl, tetrazolyl, furanyl, thienyl, oxazolyl, isoxazolyl, thiazolyl, isothiazolyl, thiadiazolyl, oxadiazolyl, pyridinyl, pyrimidinyl, pyrazinyl, pyranyl, pyridazinyl and triazinyl;

Het$^5$ represents a three-membered, four-membered, five-membered or six-membered aromatic or non-aromatic, monocyclic or polycyclic heterocycle comprising one or more, preferably one to four, heteroatoms, preferably selected from nitrogen, oxygen, sulfur and phosphorus, or a fused polycyclic ring system including such heterocycle (such as for instance a fused benzoheterocycle); non-limiting examples of such heterocycles include for instance pyrrolyl, pyrrolinyl, imidazolyl, imidazolinyl, pyrazolyl, pyrazolinyl, triazolyl, tetrazolyl, furanyl, tetrahydrofuranyl, thienyl, thiolanyl, dioxolanyl, oxazolyl, oxazolinyl, isoxazolyl, thiazolyl, thiazolinyl, isothiazolyl, thiadiazolyl, oxadiazolyl, pyridinyl, pyrimidinyl, pyrazinyl, pyranyl, pyridazinyl, pyrrolidinyl, piperidinyl, piperazinyl, morpholinyl, thiomorpholinyl, tetrahydropyranyl, dioxanyl, dithianyl, trithianyl, triazinyl, benzothienyl, isobenzothienyl, benzofuranyl, isobenzofuranyl, benzothiazolyl, benzoxazolyl, benzodioxanyl, indolyl, isoindolyl, indolinyl, purinyl, 1H-pyrazolo[3,4-d]pyrimidinyl, benzimidazolyl, quinolyl, isoquinolyl, cinnolinyl, phtalazinyl, quinazolinyl, quinoxalinyl, thiazolopyridinyl, oxazolopyridinyl and imidazo[2,1-b]thiazolyl; wherein said heterocycles each independently may be substituted with, where possible, one, two, three or four substituents each independently selected from hydroxy, mercapto, carbonyl, C$_{1-4}$alkyl, C$_{1-4}$alkyloxy, C$_{1-4}$alkylthio, C$_{1-4}$alkylcarbonyl, piperidinyl, NR$^{17}$R$^{18}$, C(=O)—Z—C$_{1-6}$alkyl, R$^6$, sulfonamido and C$_{1-4}$alkyl substituted with one or two substituents independently selected from hydroxy, C$_{1-4}$alkyloxy, mercapto, C$_{1-4}$alkylthio, phenyl, C(=O)—Z—C$_{1-16}$alkyl, —Y—C$_{1-4}$alkanediyl-C(=O)—Z—C$_{1-6}$alkyl, R$^6$ and NR$^{17}$R$^{18}$;

Het$^6$ represents a three-membered, four-membered, five-membered or six-membered aromatic or non-aromatic monocyclic heterocycle comprising one or more, preferably one to four, heteroatoms, preferably selected from nitrogen, oxygen, sulfur and phosphorus; non-limiting examples of such heterocycles include for instance pyrrolidinyl, piperidinyl, azaridinyl, pyrazolinyl and pyrolinyl, wherein said heterocycle may optionally be substituted with one, or where possible, two or three substituents each independently selected from Het$^2$, R$^{11}$ and C$_{1-4}$alkyl optionally substituted with one or more substituents independently selected from Het$^2$ and R$^{11}$, provided however that R$^2$ is other than C$_{1-6}$ alkyloxycarbonylC$_{1-6}$alkyl or aminocarbonyl; and R$^7$, R$^8$, R$^9$ and R$^{10}$ are other than aminocarbonyl, C$_{1-4}$alkylcarbonyloxy-C$_{1-4}$alkylcarbonyl, hydroxyC$_{1-4}$alkylcarbonyl, C$_{1-4}$alkyloxycarbonylcarbonyl, C(=O)—O—R$^{19}$, C$_{1-4}$alkanediylC(=O)—O—R$^{19}$ or —Y—C$_{1-4}$alkanediylC(=O)—O—R$^{19}$; and R$^{12}$ and R$^{13}$ are other than C$_{1-4}$alkylcarbonyloxy-C$_{1-4}$alkylcarbonyl, hydroxyC$_{1-4}$alkylcarbonyl or C$_{1-4}$alkylcarbonylcarbonyl; and R$^{11}$ is other than C(=O)—O—R$^{19}$, Y—C$_{1-4}$alkanediyl—C(=O)—OR$^{19}$, C(=O)NH$_2$, C(=O)NHC$_{1-4}$alkyl or C(=O)NHC$_{3-7}$cycloalkyl; and R$^{15}$ and R$^{16}$ are other than aminocarbonyl, C$_{1-4}$alkylcarbonyloxy-C$_{1-4}$alkylcarbonyl, hydroxy C$_{1-4}$alkylcarbonyl or C$_{1-4}$alkyloxycarbonylcarbonyl; and aryl is other than phenyl substituted with C(=O)—O—R$^{19}$, C(=O)NH$_2$, C(=O)NHC$_{1-4}$alkyl, C(=O)NHC$_{3-7}$ cycloalkyl and/or with C$_{1-4}$alkyl substituted with C(=O)—O—R$^{19}$ or Y—C$_{1-4}$alkanediyl—C(=O)—O—R$^{14}$; and Het$^3$ is other than a monocyclic heterocycle substituted with C(=O)·O—R$^{19}$ and/or with C$_{1-4}$alkyl substituted with C(=O)—O—R$^{19}$ and/or Y—C$_{1-4}$alkanediyl C(=O)—O—R$^{19}$; and in each of the above proviso's R$^{19}$ is defined as hydrogen, C$_{1-4}$alkyl, C$_{3-7}$cycloalkyl, aminocarbonylmethylene or mono- or di(C$_{1-4}$alkyl)aminocarbonylmethylene; and wherein the said compound having the formula (1) contains at least one —C(=O)—Z—R$^{14}$ moiety.

As used in the foregoing definitions and hereinafter:

the term "halo" is generic to fluoro, chloro, bromo and iodo;

the term "C$_{3-7}$cycloalkyl" is generic to cyclopropyl, cyclobutyl, cyclopentyl, cyclohexyl and cycloheptyl;

the term "C$_{1-4}$alkyl" defines straight and branched chain saturated hydrocarbon radicals having from 1 to 4 carbon atoms such as, for example, methyl, ethyl, propyl, butyl, 1-methylethyl, 2-methylpropyl, 2,2-dimethylethyl and the like;

the term "C$_{1-6}$alkyl" is meant to include C$_{1-4}$alkyl and the higher homologues thereof having 5 or 6 carbon atoms such as, for example, pentyl, 2-methylbutyl, hexyl, 2-methylpentyl and the like;

the term "C$_{1-20}$alkyl" is meant to include C$_{1-6}$alkyl and the higher homologues thereof having 7 to 20 carbon atoms such as, for example, heptyl, octyl, nonyl, decyl, undecyl, dodecyl, tridecyl, tetradecyl, pentadecyl, octadecyl, nonadecyl, eicosyl and the like;

the term "C$_{5-20}$alkyl" is meant to include C$_{1-20}$alkyl except for C$_{1-4}$alkyl;

the term "C$_{3-20}$alkenyl" defines straight and branched chain hydrocarbon radicals containing one double bond and having from 3 to 20 carbon atoms such as, for example, 2-propenyl, 3-butenyl, 2-butenyl, 2-pentenyl, 3-pentenyl, 3-methyl-2-butenyl, 3-hexenyl and the like, the carbon atom of the said C$_{3-20}$alkenyl connected to the remainder of the molecule being preferably saturated;

the term "C$_{3-20}$alkynyl" defines straight and branched chain hydrocarbon radicals containing one triple bond and having from 3 to 20 carbon atoms such as, for example, 2-propynyl, 3-butynyl, 2-butynyl, 2-pentynyl, 3-pentynyl, 3-methyl-2-butynyl, 3-hexynyl and the like, the carbon atom of the said C$_{3-20}$alkynyl connected to the remainder of the molecule being preferably saturated;

the term "polyhaloC$_{1-4}$alkyl" is defined as polyhalosubstituted C$_{1-4}$alkyl, in particular C$_{1-4}$alkyl substituted with 1 to 6 halogen atoms, more particularly difluoro- or trifluoromethyl;

the term "polyhaloC$_{1-6}$alkyl" is defined as polyhalosubstituted C$_{1-6}$alkyl;

the term "polyhaloC$_{1-20}$alkyl" is defined as polyhalosubstituted C$_{1-20}$alkyl;

the term "C$_{1-4}$alkanediyl" defines bivalent straight or branch chained alkanediyl radicals having from 1 to 4 carbon atoms such as, for example, methylene, 1,2-ethanediyl, 1,3-propanediyl, 1,4-butanediyl and the like;

the term "C$_{2-6}$alkanediyl" defines bivalent straight or branch chained alkanediyl radicals having from 2 to 6 carbon atoms such as, for example, 1,2-ethanediyl, 1,3-propanediyl, 1,4-butanediyl, 1,5-pentanediyl, 1,6-hexanediyl and the like.

Het$^1$, Het$^2$, Het$^3$, Het$^4$ and Het$^5$ are meant to include all possible isomeric forms of the heterocycles mentioned in the above definitions, for instance pyrrolyl also includes 2H-pyrrolyl; triazolyl includes 1,2,4-triazolyl and 1,3,4-triazolyl; oxadiazolyl includes 1,2,3-oxadiazolyl, 1,2,4-oxadiazolyl, 1,2,5-oxadiazolyl and 1,3,4-oxadiazolyl; thiadiazolyl includes 1,2,3-thiadiazolyl, 1,2,4-thiadiazolyl, 1,2,5-thiadiazolyl and 1,3,4-thiadiazolyl; pyranyl includes 2H-pyranyl and 4H-pyranyl.

The heterocycles represented by Het$^1$, Het$^2$, Het$^3$, Het$^4$ and Het$^5$ may be attached to the remainder of the molecule of formula (I) through any ring carbon or heteroatom as appropriate. Thus, for example, when the heterocycle is imidazolyl, it may be a 1-imidazolyl, 2-imidazolyl, 4-imidazolyl and 5-imidazolyl; when it is thiazolyl, it may be 2-thiazolyl, 4-thiazolyl and 5-thiazolyl; when it is triazolyl, it may be 1,2,4-triazol-1-yl, 1,2,4-triazol-3-yl, 1,2,4-triazol-5-yl, 1,3,4-triazol-1-yl and 1,3,4-triazol-2-yl; when it is benzothiazolyl, it may be 2-benzothiazolyl, 4-benzothiazolyl, 5-benzothiazolyl, 6-benzothiazolyl and 7-benzothiazolyl.

The C$_{1-20}$acyl is derived from:

| acetic acid | CH$_3$COOH | tridecanoic acid | C$_{12}$H$_{25}$COOH |
| propionic acid | C$_2$H$_5$COOH | myristic acid | C$_{13}$H$_{27}$COOH |
| butyric acid | C$_3$H$_7$COOH | pentadecanoic acid | C$_{14}$H$_{29}$COOH |
| valeric acid | C$_4$H$_9$COOH | palmitic acid | C$_{15}$H$_{31}$COOH |
| hexanoic acid | C$_5$H$_{11}$COOH | heptadecanoic acid | C$_{16}$H$_{33}$COOH |
| heptanoic acid | C$_6$H$_{13}$COOH | stearic acid | C$_{17}$H$_{35}$COOH |
| octanoic acid | C$_7$H$_{15}$COOH | oleic acid | C$_{17}$H$_{33}$COOH |
| nonanoic acid | C$_8$H$_{17}$COOH | linolic acid | C$_{17}$H$_{31}$COOH |
| decanoic acid | C$_9$H$_{19}$COOH | linolenic acid | C$_{17}$H$_{29}$COOH |
| undecanoic acid | C$_{10}$H$_{21}$COOH | nonadecanoic acid | C$_{18}$H$_{37}$COOH |
| lauric acid | C$_{11}$H$_{23}$COOH | icosanoic acid | C$_{19}$H$_{39}$COOH |

The pharmaceutically acceptable addition salts as mentioned hereinabove are meant to comprise the therapeutically active non-toxic acid addition salt forms which the compounds having the formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, ethanedioic, propanedioic, butanedioic, 2-butenedioic, 2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like. Conversely the salt form can be converted by treatment with alkali into the free base form.

Compounds having the formula (I) which contain acidic protons may be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, 2-amino-2-(hydroxymethyl)-1,3-propanediol, hydrabamine salts, and salts with naturally occurring aminoacids such as, for example, arginine, lysine and the like. Conversely the salt form can be converted by treatment with an acid into the free acid form. The term addition salt also comprises the hydrates and solvent addition forms of such salts which the compounds having the formula (I) are able to form. Examples of such forms are e.g. hydrates, alcoholates and the like.

The N-oxide forms of the present compounds are meant to comprise compounds having the formula (I), wherein one or several nitrogen atoms are oxidized to the so-called N-oxide. For example, one or more nitrogen atoms of any of the heterocycles in the definition of Het$^1$, Het$^2$, Het$^3$, Het$^4$ and Het$^5$ may be N-oxidized.

Some of the compounds of formula (I) may also exist in their tautomeric forms. Such forms although not explicitly indicated in the above formula are intended to be included within the scope of the present invention. For example, a hydroxy substituted triazine moiety may also exist as the corresponding triazinone moiety; a hydroxy substituted pyrimidine moiety may also exist as the corresponding pyrimidinone moiety.

The term "stereochemically isomeric forms" as used hereinbefore defines all the possible stereoisomeric forms in which the compounds of formula (I) can exist. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration, used herein in accordance with Chemical Abstracts nomenclature. Stereochemically isomeric forms of the compounds of formula (I) certainly are intended to be embraced within the scope of this invention.

The compounds of formula (I) and some of the intermediates in the present invention contain one or more asymmetric carbon atoms. The pure and mixed stereochemically isomeric forms of the compounds of formula (I) are also intended to be embraced within the scope of the present invention. Whenever used hereinafter, the term "compounds of formula (I)" is meant to also include their N-oxide forms, their pharmaceutically acceptable addition salts, and their stereochemically isomeric forms.

An interesting group of compounds are those compounds of formula (I) wherein the 6-azauracil moiety is connected to the phenyl ring in the para or meta position relative to the carbon atom bearing the $-X-R^2$, $R^3$ and $R^4$ substituents; preferably in the para position. Another interesting group contains those compounds of formula (I) wherein one or more of the following restrictions apply:

p is 0, 1 or 2;

X is S, $NR^5$ or a direct bond; more preferably a direct bond;

each $R^1$ independently is halo, polyhalo$C_{1-6}$alkyl, $C_{1-6}$alkyl, $C_{1-6}$alkyloxy or aryl, preferably, chloro or trifluoromethyl, more preferably chloro;

the at least one $-C(=O)-Z-R^{14}$ moiety contained by the compound of formula (I) is born by R.

R is $Het^1$ or $C_{1-6}$alkyl substituted with one or two substituents selected from hydroxy, cyano, amino, mono- or di($C_{1-4}$alkyl)amino, $C(=O)-Z-R^{14}$, $C_{1-6}$alkyloxy optionally substituted with $C(=O)-Z-R^{14}$, $C_{1-6}$alkylsulfonyloxy, $C_{3-7}$cycloalkyl optionally substituted with $C(=O)-Z-R^{14}$, aryl, aryloxy, arylthio, $Het^1$, $Het^1$oxy and $Het^1$thio; and if X is O, S or $NR^5$, then $R^2$ may also represent aminothiocarbonyl, $C_{1-4}$alkylcarbonyl optionally substituted with $C(=O)-Z-R^{14}$, $C_{1-4}$alkylthiocarbonyl optionally substituted with $C(=O)-Z-R^{14}$, arylcarbonyl, arylthiocarbonyl, $Het^1$carbonyl or $Het^1$thiocarbonyl; more preferably $R^2$ is $Het^1$ $R^3$ is hydrogen, methyl, ethyl, propyl or cyclohexyl, more preferably methyl;

$R^4$ is hydrogen or methyl, more preferably methyl;

$R^3$ and $R^4$ are taken together to form a 1,4-butanediyl;

$R^6$ is $C_{1-6}$alkylsulfonyl, aminosulfonyl or $Het^6$sulfonyl, more preferably $Het^6$sulfonyl;

$R^7$ and $R^8$ are each independently hydrogen, $C_{1-4}$alkyl, $Het^3$ or $R^6$;

$R^9$ and $R^{10}$ are each independently hydrogen, $C_{1-4}$alkyloxy$C_{1-4}$alkyl, $C_{1-4}$alkylcarbonyl, aminocarbonyl, $Het^3$carbonyl, $Het^3$ or $R^6$;

$R^{11}$ is cyano, nitro, halo, $C_{1-4}$alkyloxy, formyl, $NR^7R^8$, $C(=O)NR^{15}R^{16}$, $-C(=O)-Z-R^{14}$, aryl, arylcarbonyl, $Het^3$ or $C(=O)Het^3$; more preferably $R^{11}$ is phenyl, $-C(=O)-O-R^{14}$, $-C(=O)-S-R^{14}$ or $-C(=O)-NH-R^{14}$.

each $R^{11}$ independently being selected from hydroxy, mercapto, cyano, nitro, halo, trihalomethyl, $C_{1-4}$alkyloxy optionally substituted with $C(=O)-Z-R^{14}$, $C_{1-6}$alkylthio optionally substituted with $C(=O)-Z-R^{14}$, formyl, trihalo$C_{1-4}$alkylsulfonyloxy, $R^6$, $NR^7R^3$, $C(=O)NR^{15}R^{16}$, $-C(=O)-Z-R^{14}$, $-Y-C_{1-4}$alkanediyl-$C(=O)-Z-R^{14}$, aryl, aryloxy, arylcarbonyl, arylthiocarbonyl, $C_{3-7}$cycloalkyl optionally substituted with $C(=O)-Z-R^{14}$, $C_{3-7}$cycloalkyloxy optionally substituted with $C(=O)-Z-R^{14}$, $C_{3-7}$cycloalkylthio optionally substituted with $C(=O)-Z-R^{14}$, phthalimide-2-yl, $Het^3$, $C(=O)Het^3$, $C(=O)C_{1-4}$alkyl optionally be substituted with one or more substituents independently selected from hydroxy, mercapto, halo and phenyl;

$R^{14}$ is dihydrofuranyl, $C_{5-20}$alkyl, $C_{3-20}$alkenyl, polyhalo$C_{1-6}$alkyl, $Het^5$, a radical of formula (a) or $C_{1-20}$alkyl substituted with one or more substituents selected from phenyl, $C_{1-4}$alkylamino, cyano, $Het^1$, $Het^5$, hydroxy and $C_{3-7}$cycloalkyl, more preferably a radical of formula (a) in which $R^j$ is $C_{1-6}$alkyl and s is 2, or $C_{1-20}$alkyl substituted with hydroxy or $Het^5$;

$R^{17}$ and $R^{18}$ are each independently hydrogen or phenyl;

aryl is phenyl optionally substituted with one, two or three substituents each independently selected from nitro, cyano, halo, hydroxy, $C_{1-4}$alkyl, $C_{3-7}$cycloalkyl, $C_{1-4}$alkyloxy, formyl, polyhalo$C_{1-4}$alkyl, $NR^9R^{10}$, $C(=O)NR^9R^{10}$, $C(=O)-O-R^{14}$, $-O-R^6$, phenyl, $C(=O)Het^3$ and $C_{1-4}$alkyl substituted with one or more substituents each independently selected from halo, hydroxy, $C_{1-4}$alkyloxy, $C(=O)-Z-R^{14}$, $Het^3$ and $NR^9R^{10}$;

$Het^1$ is a monocyclic heterocycle selected from pyrrolyl, imidazolyl, pyrazolyl, triazolyl, tetrazolyl, furanyl, thienyl, oxazolyl, isoxazolyl, thiazolyl, isothiazolyl, thiadiazolyl, oxadiazolyl, pyridinyl, pyrimidinyl, pyrazinyl, pyranyl, pyridazinyl and triazinyl, in particular imidazolyl, oxadiazolyl, thiazolyl, pyrimidinyl or pyridinyl, wherein said monocyclic heterocycles each independently may optionally be substituted with one, or where possible, two or three substituents each independently selected from $Het^2$, $R^{11}$ and $C_{1-4}$alkyl optionally substituted with $Het^2$ or $R^{11}$; more preferably $Het^1$ is imidazolyl, oxadiazolyl, thiazolyl or pyridinyl, especially thiazolyl, each independently and optionally substituted with one, or where possible, two or three substituents each independently selected from $Het^2$, $R^{11}$ and $C_{1-4}$alkyl optionally substituted with $Het^2$ or $R^{11}$, more preferably two substituents each independently selected from $R^{11}$ and $C_{1-4}$alkyl substituted with $R^{11}$;

$Het^2$ is an aromatic heterocycle; more in particular furanyl, thienyl, pyridinyl or benzothienyl, wherein said aromatic heterocycles each independently may optionally be substituted with one, or where possible, two or three substituents each independently selected from $R^{11}$ and $C_{1-4}$alkyl;

$Het^3$ is piperidinyl, piperazinyl, morpholinyl or tetrahydropyranyl each independently and optionally substituted with, where possible, one, two, three or four substituents each independently selected from hydroxy, $C_{1-4}$alkyl, $C_{1-4}$alkylcarbonyl, piperidinyl and $C_{1-4}$alkyl substituted with one or two substituents independently selected from hydroxy, $C_{1-4}$alkyloxy and phenyl;

$Het^4$ is thienyl;

$Het^5$ is piperidinyl or piperazinyl optionally substituted with $C_{1-4}$alkyl, sulfonamido or $R^6$, more preferably $R^6$;

$Het^6$ is pyrrrolidinyl.

Particular compounds are those compounds of formula (I) wherein p is 2 and both $R^1$ substituents are chloro; more preferably the two chloro substituents are in the ortho positions relative to the carbon atom bearing the —X—$R^2$, $R^3$ and $R^4$ substituents.

Other particular compounds are those compounds of formula (I) wherein the 6-azauracil moiety is in the para position relative to the carbon atom bearing the —X—$R^2$, $R^3$ and $R^4$ substituents, and p is 2 whereby both $R^1$ substituents are chloro positioned ortho relative to the carbon atom bearing the —X—$R^2$, $R^3$ and $R^4$ substituents.

Other particular compounds are those compounds of formula (I) wherein X is a direct bond and $R^2$ is a monocyclic heterocycle selected from pyrrolyl, imidazolyl, pyrazolyl, triazolyl, tetrazolyl, furanyl, thienyl, oxazolyl, isoxazolyl, thiazolyl, isothiazolyl, thiadiazolyl, oxadiazolyl, pyridinyl, pyrimidinyl, pyrazinyl, pyranyl, pyridazinyl and triazinyl, in particular imidazolyl, oxadiazolyl, thiazolyl, pyrimidinyl or pyridinyl, wherein said monocyclic heterocycles each independently may optionally be substituted with one, or where possible, two or three substituents each independently selected from $Het^2$, $R^{11}$ and $C_{1-4}$alkyl optionally substituted with $Het^2$ or $R^{11}$; more in particular $R^2$ is optionally substituted thiazolyl, pyridinyl or oxadiazolyl.

Preferred compounds are those compounds of formula (I) wherein $R^3$ and $R^4$ are both methyl and —X—$R^2$ is $Het^1$ wherein $Het^1$ suitably is optionally substituted thiazolyl, pyridinyl or oxadiazolyl.

More preferred compounds are those compounds of formula (I) wherein $R^3$ and $R^4$ are both methyl, —X—$R^2$ is optionally substituted 2-thiazolyl or 3-oxadiazolyl, the 6-azauracil moiety is in the para position relative to the carbon atom bearing the —X—$R^2$, $R^3$ and $R^4$ substituents, and p is 2 whereby both $R^1$ substituents are chloro positioned ortho relative to the carbon atom bearing the —X—$R^2$, $R^3$ and $R^4$ substituents. Particularly preferred such compounds are those in which —X—$R^2$ is di-substituted with phenyl and either (i) $R^{11}$ where $R^{11}$ is a group of formula —C(=O)—Z—$R^{14}$ in which Z is 0 and $R^{14}$ is $C_{1-20}$alkyl substituted with hydroxy or with $Het^5$ especially where $Het^5$ is piperazinyl substituted with $Het^6$sulfonyl, especially where $Het^6$ is pyrrolidinyl, or $R^{14}$ is a radical of formula (a) in which $R^j$ is $C_{1-6}$alkyl and s is 2, or (ii) $C_{1-4}$alkyl substituted with $R^{11}$ where $R^{11}$ is a a group of formula —C(=O)—Z—$R^{14}$ in which Z is 0 and $R^{14}$ is a radical of formula (a) in which $R^j$ is $C_{1-6}$alkyl and s is 2.

Particularly preferred compounds are those of formulae (A), (B), (C) and (D) below:

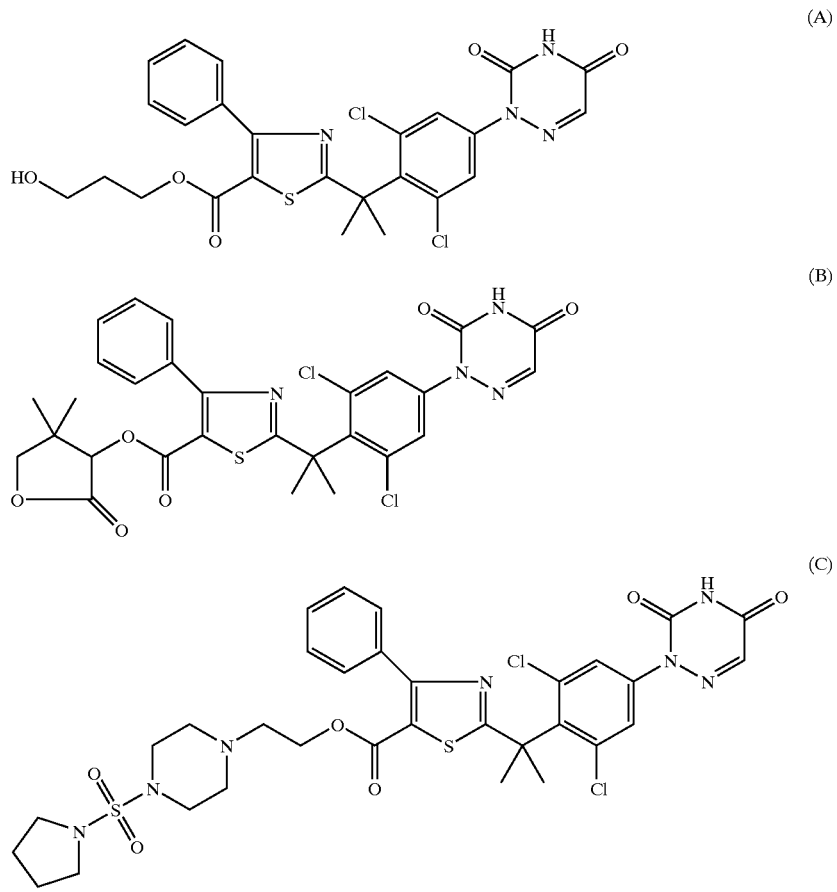

-continued

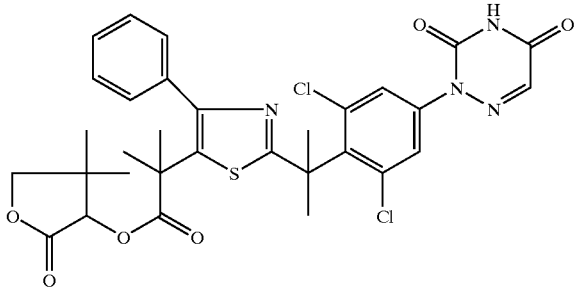

(D)

Examples of compounds of formula (I) further includes compounds of formula (I') in which p, X, Y, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, n, m, $R^a$, $R^b$, $R^c$, $R^d$, $R^e$, $R^f$, $R^g$, $R^h$, $R^{15}$, $R^{16}$, Z, aryl, 'Het$^1$, Het$^2$, Het$^3$, Het$^4$ as used in relation to compounds of formula (1') have the meanings below:

The present invention is concerned with the compounds of formula

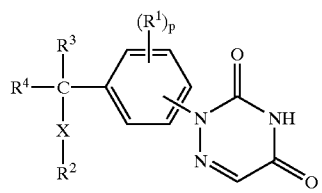

(I')

the N-oxides, the pharmaceutically acceptable addition salts and the stereochemically
isomeric forms thereof, wherein p represents an integer being 0, 1, 2, 3 or 4;
X represents O, S, $NR^5$ or a direct bond or —X—$R^2$ taken together may represent cyano;
Y represents O, S, $NR^5$, or $S(O)_2$;
each $R^1$ independently represents C(=O)·Z—$R^{14}$, $C_{1-6}$alkyl, halo, polyhalo$C_{1-6}$alkyl, hydroxy, mercapto, $C_{1-6}$alkyloxy, $C_{1-6}$alkylthio, $C_{1-6}$alkylcarbonyloxy, aryl, cyano, nitro, Het$^3$, $R^6$, $NR^7R^8$ or $C_{1-4}$alkyl substituted with C(=O)—Z·$R^{14}$, Het$^3$, $R^6$ or $NR^7R^8$;
$R^2$ represents Het$^1$, $C_{3-7}$cycloalkyl optionally substituted with C(=O)—Z—$R^{14}$, $C_{1-6}$alkyl or $C_{1-6}$alkyl substituted with one or two substituents selected from C(=O)·Z—$R^{14}$, hydroxy, cyano, amino, mono- or di($C_{1-4}$alkyl)amino, $C_{1-6}$alkyloxy optionally substituted with C(=O)—Z—$R^{14}$, $C_{1-6}$alkylsulfonyloxy, $C_{3-7}$cycloalkyl optionally substituted with C(=O)—Z—$R^{14}$, aryl, aryloxy, arylthio, Het$^1$, Het$^1$oxy and Het$^1$thio; and if X is O, S or $NR^5$, then $R^2$ may also represent aminothiocarbonyl, $C_{1-4}$alkylcarbonyl optionally substituted with C(=O)—Z—$R^{14}$, $C_{1-4}$alkylthiocarbonyl optionally substituted with C(=O)—Z—$R^{14}$, arylcarbonyl, arylthiocarbonyl, Het$^1$carbonyl or Het$^1$thiocarbonyl;
$R^3$ represents hydrogen, $C_{1-6}$alkyl or $C_{3-7}$cycloalkyl;
$R^4$ represents hydrogen, $C_{1-6}$alkyl or $C_{3-7}$cycloalkyl; or
$R^3$ and $R^4$ taken together form a $C_{2-6}$alkanediyl;
$R^5$ represents hydrogen or $C_{1-4}$alkyl;
each $R^6$ independently represents $C_{1-6}$alkylsulfonyl, aminosulfonyl, mono- or di-($C_{1-4}$alkyl)aminosulfonyl, mono- or di(benzyl)aminosulfonyl, polyhalo$C_{1-6}$alkylsulfonyl, $C_{1-6}$alkylsulfinyl, phenyl$C_{1-4}$alkylsulfonyl, piperazinylsulfonyl, aminopiperidinylsulfonyl, piperidinylaminosulfonyl, N—$C_{1-4}$alkyl-N-piperidinylaminosulfonyl or mono- or di($C_{1-4}$alkyl)amino$C_{1-4}$alkylsulfonyl;
each $R^7$ and each $R^8$ are independently selected from hydrogen, $C_{1-4}$alkyl, hydroxy$C_{1-4}$alkyl, dihydroxy$C_{1-4}$alkyl, aryl, aryl$C_{1-4}$alkyl, $C_{1-4}$alkyloxy$C_{1-4}$alkyl, $C_{1-4}$alkylcarbonyl, arylcarbonyl, Het$^3$carbonyl, mono- or di($C_{1-4}$alkyl)amino$C_{1-4}$alkyl, arylaminocarbonyl, arylaminothiocarbonyl, Het$^3$aminocarbonyl, Het$^3$aminothiocarbonyl, $C_{3-7}$cycloalkyl, pyridinyl$C_{1-4}$alkyl, $C_{1-4}$alkanediylC(=O)—Z—$R^{14}$, —C(=O)—Z—$R^{14}$, —Y—$C_{1-4}$alkanediyl-C(=O)—Z—$R^{14}$, Het$^3$ and $R^6$;
$R^9$ and $R^{10}$ are each independently selected from hydrogen, $C_{1-4}$alkyl, hydroxy$C_{1-4}$alkyl, dihydroxy$C_{1-4}$alkyl, phenyl, phenyl$C_{1-4}$alkyl, $C_{1-4}$alkyloxy$C_{1-4}$alkyl, $C_{1-4}$alkylcarbonyl, phenylcarbonyl, Het$^3$carbonyl, mono- or di($C_{1-4}$alkyl)amino$C_{1-4}$alkyl, phenylaminocarbonyl, phenylaminothiocarbonyl, Het$^3$aminocarbonyl, Het$^3$aminothiocarbonyl, $C_{3-7}$cycloalkyl, pyridinyl$C_{1-4}$alkyl, $C_{1-4}$alkanediyl-C(=O)—Z—$R^{14}$, —C(=O)—Z—$R^{14}$, —Y—$C_{1-4}$alkanediyl-C(=O)—Z—$R^{14}$, Het$^3$ and $R^6$;
each $R^{11}$ independently being selected from hydroxy, mercapto, cyano, nitro, halo, trihalomethyl, $C_{1-4}$alkyloxy optionally substituted with C(=O)—Z—$R^{14}$, formyl, trihalo$C_{1-4}$alkylsulfonyloxy, $R^6$, $NR^7R^8$, C(=O) $NR^{15}R^{16}$, —C(=O)—Z—$R^{14}$, —Y—$C_{1-4}$alkanediyl-C (=O)—Z—$R^{14}$, aryl, aryloxy, arylcarbonyl, $C_{3-7}$cycloalkyl optionally substituted with C(=O)—Z—$R^{14}$, $C_{3-7}$cycloalkyloxy optionally substituted with C(=O)—Z—$R^{14}$, phthalimide-2-yl, Het$^3$, Het$^4$ and C(=O)Het$^3$;
$R^{12}$ and $R^{13}$ are each independently selected from hydrogen, $C_{1-4}$alkyl, hydroxy$C_{1-4}$alkyl, dihydroxy$C_{1-4}$alkyl, phenyl, phenyl$C_{1-4}$alkyl, $C_{1-4}$alkyloxy$C_{1-4}$alkyl, $C_{1-4}$alkylcarbonyl, phenylcarbonyl, mono- or di($C_{1-4}$alkyl)amino$C_{1-4}$alkyl, phenylaminocarbonyl, phenylaminothiocarbonyl, $C_{3-7}$cycloalkyl, pyridinyl$C_{1-4}$alkyl, $C_{1-4}$alkanediyl-C(=O)—Z—$R^{14}$, —C(=O)—Z—$R^{14}$, —Y—$C_{1-4}$alkanediyl-C(=O)—Z—$R^{14}$ and $R^5$;
each $R^{14}$ independently represents $C_{1-4}$ alkyl substituted with one or more substituents selected from phenyl, di-$C_{1-4}$alkylamino, cyano, Het$^1$ and $C_{3-7}$ cycloalkyl, hydrogen, $C_{1-20}$acyl (having a straight or branched, saturated or unsaturated hydrocarbon chain having 1 to 20 carbon atoms), $C_{1-20}$alkyl, $C_{3-7}$cycloalkyl, polyhalo$C_{1-20}$alkyl or a radical of formula (a) 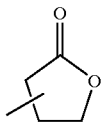

(b) 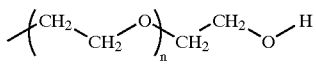

(c) 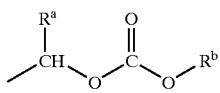

(d) 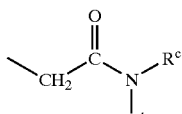

(e) 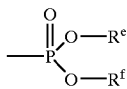

wherein n is 0 to 5;
$R^a$, $R^b$, $R^c$, $R^d$, $R^e$ and $R^f$ are each independently hydrogen, $C_{1-6}$alkyl or $C_{3-7}$cycloalkyl; or
$R^e$ and $R^f$ taken together may form —CH$_2$—CH$_2$—, —CH$_2$—CH$_2$—CH$_2$— or —CH$_2$—CH$_2$—CH$_2$—CH$_2$—; or a radical of formula (h) 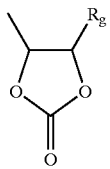

(i) 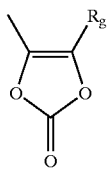

(j) 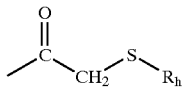

(k) 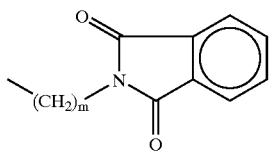

wherein m is 1 to 4
$R_g$ and $R_h$ are each independently $C_{1-4}$ alkyl;
each Z independently represents O, S, NH, —CH$_2$—O— or —CH$_2$—S— whereby —CH$_2$— is attached to the carbonyl group;
—Z—R$^{14}$ taken together form a radical of formula (f)

\[structure: CH$_2$—CN\]

(g)

\[structure: phosphonate with O—R$^e$ and O—R$^f$, CH$_2$\]

$R^{15}$ and $R^{16}$ are each independently selected from dihydroxyC$_{1-4}$alkyl, aryl, arylC$_{1-4}$alkyl, C$_{1-4}$alkyloxyC$_{1-4}$alkyl, —C(=O)—Z—R$^{14}$, arylcarbonyl, mono- or di(C$_{1-4}$ alkyl)aminoC$_{1-4}$alkyl, arylaminocarbonyl, arylaminothiocarbonyl, Het$^3$aminocarbonyl, Het$^3$aminothiocarbonyl, pyridinylC$_{1-4}$alkyl, Het$^3$ or R$^6$;
aminocarbonylmethylene or mono- or di(C$_{1-4}$alkyl) aminocarbonyl methylene;
aryl represents phenyl optionally substituted with one, two or three substituents each independently selected from nitro, azido, cyano, halo, hydroxy, C$_{1-4}$alkyl, C$_{3-7}$cycloalkyl, C$_{1-4}$alkyloxy, formyl, polyhaloC$_{1-4}$alkyl, NR$^9$R$^{10}$, C(=O)NR$^9$R$^{10}$, C(=O)—Z—R$^{14}$, R$^6$, —O—R$^6$, phenyl, Het$^3$, C(=O)Het$^3$ and C$_{1-4}$alkyl substituted with one or more substituents each independently selected from halo, hydroxy, C$_{1-4}$alkyloxy, C(=O)—Z—R$^{14}$, —Y—C$_{1-4}$alkanediyl-C(=O)—Z—R$^{14}$, Het$^3$ or NR$^9$R$^{10}$;
Het$^1$ represents a heterocycle selected from pyrrolyl, pyrrolinyl, imidazolyl, imidazolinyl, pyrazolyl, pyrazolinyl, triazolyl, tetrazolyl, furanyl, tetrahydrofuranyl, thienyl, thiolanyl, dioxolanyl, oxazolyl, oxazolinyl, isoxazolyl, thiazolyl, thiazolinyl, isothiazolyl, thiadiazolyl, oxadiazolyl, pyridinyl, pyrimidinyl, pyrazinyl, pyranyl, pyridazinyl, pyrrolidinyl, piperidinyl, piperazinyl, morpholinyl, thiomorpholinyl, dioxanyl, dithianyl, trithianyl, triazinyl, benzothienyl, isobenzothienyl, benzofuranyl, isobenzofuranyl, benzothiazolyl, benzoxazolyl, indolyl, isoindolyl, indolinyl, purinyl, 1H-pyrazolo[3,4-d]pyrimidinyl, benzimidazolyl, quinolyl, isoquinolyl, cinnolinyl, phtalazinyl, quinazolinyl, quinoxalinyl, thiazolopyridinyl, oxazolopyridinyl and imidazo[2,1-b]thiazolyl; wherein said heterocycles each independently may optionally be substituted with one, or where possible, two or three substituents each independently selected from Het$^2$, R$^{11}$ and C$_{1-4}$alkyl optionally substituted with one or two substituents independently selected from Het$^2$ and R$^{11}$;
Het$^2$ represents a heterocycle selected from pyrrolyl, pyrrolinyl, imidazolyl, imidazolinyl, pyrazolyl, pyrazolinyl, triazolyl, tetrazolyl, furanyl, tetrahydrofuranyl, thienyl, thiolanyl, dioxolanyl, oxazolyl, oxazolinyl, isoxazolyl, thiazolyl, thiazolinyl, isothiazolyl, thiadiazolyl, oxadiazolyl, pyridinyl, pyrimidinyl, pyrazinyl, pyranyl, pyridazinyl, dioxanyl, dithianyl, trithianyl, triazinyl, benzothienyl, isobenzothienyl, benzofuranyl, isobenzofuranyl, benzothiazolyl, benzoxazolyl, indolyl, isoindolyl, indolinyl, purinyl, 1H-pyrazolo[3,4-d]pyrimidinyl, benzimidazolyl, quinolyl, isoquinolyl, cinnolinyl, phtalazinyl, quinazolinyl, quinoxalinyl, thiazolopyridinyl, oxazolopyridinyl and imidazo[2,1-b]thiazolyl; wherein said heterocycles each independently may optionally be substituted with one, or where possible, two or three substituents each independently selected from $R^{11}$ and $C_{1-4}$alkyl optionally substituted with one or two substituents independently selected from $R^{11}$;

Het$^3$ represents a monocyclic heterocycle selected from pyrrolidinyl, piperidinyl, piperazinyl, morpholinyl, thiomorpholinyl and tetrahydropyranyl; wherein said monocyclic heterocycles each independently may optionally be substituted with, where possible, one, two, three or four substituents each independently selected from hydroxy, $C_{1-4}$alkyl, $C_{1-4}$alkyloxy, $C_{1-4}$alkylcarbonyl, piperidinyl, $NR^{12}R^{13}$, $C(=O)-Z-R^{14}$, $R^6$ and $C_{1-4}$alkyl substituted with one or two substituents independently selected from hydroxy, $C_{1-4}$alkyloxy, phenyl, $C(=O)-Z-R^{14}$, $-Y-C_{1-4}$alkanediyl-$C(=O)-Z-R^{14}$, $R^6$ and $NR^{12}R^{13}$;

Het$^4$ represents a monocyclic heterocycle selected from pyrrolyl, imidazolyl, pyrazolyl, triazolyl, tetrazolyl, furanyl, thienyl, oxazolyl, isoxazolyl, thiazolyl, isothiazolyl, thiadiazolyl, oxadiazolyl, pyridinyl, pyrimidinyl, pyrazinyl, pyranyl, pyridazinyl and triazinyl provided however that $R^2$ is other than $C_{1-6}$ alkyloxycarbonyl$C_{1-6}$alkyl, aminocarbonyl; and $R^7$, $R^8$, $R^9$ and $R^{10}$ are other than aminocarbonyl, $C_{1-4}$alkylcarbonyloxy-$C_{1-4}$alkylcarbonyl, hydroxy $C_{1-4}$alkylcarbonyl, $C_{1-4}$alkyloxycarbonylcarbonyl $C(=O)-O-R^{14}$, $C_{1-4}$alkanediyl$C(=O)-O-R^{14}$ and $-Y-C_{1-4}$alkanediyl$C(=O)-O-R^{14}$; and $R^{12}$ and $R^{13}$ are other than $C_{-4}$alkylcarbonyloxy-$C_{1-4}$alkylcarbonyl, hydroxy $C_{1-4}$alkylcarbonyl, $C_{1-4}$alkylcarbonylcabonyl; and $R^{11}$ is other than $C(=O)-O-R^{14}$, $Y-C_{1-4}$alkanediyl $-C(=O)-OR^{14}$, $C(=O)NH_2$, $C(=O)NHC_{1-4}$alkyl or $C(=O)NHC_{3-7}$cycloalkyl; and $R^{14}$ is other than hydrogen, $C_{1-4}$alkyl, $C_{3-7}$cycloalkyl, aminocarbonylmethylene, mono- or di ($C_{1-4}$alkyl) aminocarbonylmethylene in the event Z is 0; and $R^{15}$ and $R^{16}$ are other than aminocarbonyl, $C_{1-4}$alkylcarbonyloxy-$C_{1-4}$alkylcarbonyl, hydroxy $C_{1-4}$alkylcarbonyl or $C_{1-4}$alkyloxycarbonylcarbonyl; and Aryl is other than phenyl substituted with $C(=O)-O-R^{14}$ $C(=O)NH_2$, $C(=O)NHC_{1-4}$alkyl, $C(=O)NHC_{3-7}$ cycloalkyl and/or with $C_{1-4}$alkyl substituted with $C(=O)-O-R^{14}$ or $Y-C_{1-4}$alkanediyl $-C(=O)-O-R^{14}$; and Het$^3$ is other than a monocyclic heterocycle substituted with $C(=O)\cdot O-R^{14}$ and/or with $C_{1-4}$alkyl substituted with $C(=O)-O-R^{14}$ and/or $Y-C_{1-4}$alkanediyl $(=O)-O-R^{14}$; and The said compound of formula (I) contains at least one $-C(=O)-Z-R^{14}$ moiety.

An interesting group of compounds are those compounds of formula (I') wherein the 6-azauracil moiety is connected to the phenyl ring in the para or meta position relative to the carbon atom bearing the $-X-R^2$, $R^3$ and $R^4$ substituents; preferably in the para position.

Further compounds according to the invention include compounds of formula (I') wherein one or more of the following restrictions apply:

p is 0, 1 or 2;

X is S, $NR^5$, or a direct bond; more in particular NH or a direct bond;

each $R^1$ independently is halo, polyhalo$C_{1-6}$alkyl, $C_{1-6}$alkyl, $C_{1-6}$alkyloxy or aryl, preferably, chloro or trifluoromethyl, more preferably chloro;

R is Het$^1$ or $C_{1-6}$alkyl substituted with one or two substituents selected from hydroxy, cyano, amino, mono- or di($C_{1-4}$alkyl)amino, $C(=O)-Z-R^{14}$ $C_{1-6}$alkyloxy optionally substituted with $C(=O)-Z-R^{14}$, $C_{1-6}$alkylsulfonyloxy, $C_{3-7}$cycloalkyl optionally substituted with $C(=O)-Z-R^{14}$, aryl, aryloxy, arylthio, Het$^1$, Het$^1$oxy and Het$^1$thio; and if X is O, S or $NR^5$, then $R^2$ may also represent aminothiocarbonyl, $C_{1-4}$alkylcarbonyl optionally substituted with $C(=O)-Z-R^{14}$, $C_{1-4}$alkylthiocarbonyl optionally substituted with $C(=O)-Z-R^{14}$, arylcarbonyl, arylthiocarbonyl, Het$^1$carbonyl or Het$^1$thiocarbonyl; particularly $R^2$ is Het$^1$ or in the event X is NH, $R^2$ may also be aminothiocarbonyl or Het$^1$carbonyl;

$R^3$ is hydrogen, methyl, ethyl, propyl or cyclohexyl; preferably, methyl;

$R^4$ is hydrogen or methyl; preferably, methyl;

$R^3$ and $R^4$ are taken together to form a 1,4-butanediyl;

$R^6$ is $C_{1-6}$alkylsulfonyl or aminosulfonyl;

$R^7$ and $R^8$ are each independently hydrogen, $C_{1-4}$alkyl, Het$^3$ or $R^6$;

$R^9$ and $R^{10}$ are each independently hydrogen, $C_{1-4}$alkyloxy$C_{1-4}$alkyl, $C_{1-4}$alkylcarbonyl, aminocarbonyl, Het$^3$carbonyl, Het$^3$ or $R^6$;

$R^{11}$ is cyano, nitro halo, $C_{1-4}$alkyloxy, formyl, $NR^7R^8$, $C(=O)NR^{15}R^{16}$, $-C(=O)-Z-R^{14}$, aryl, arylcarbonyl, Het$^3$, Het$^4$ and $C(=O)$Het$^3$;

$R^{14}$ isdihydrofuranyl, $C_{5-20}$alkyl, $C_{1-4}$alkyl substituted with one or more substituents selected from phenyl, $C_{1-4}$alkylamino, cyano, Het$^1$ and $C_{3-7}$cycloalkyl;

aryl is phenyl optionally substituted with one, two or three substituents each independently selected from nitro, cyano, halo, hydroxy, $C_{1-4}$alkyl, $C_{3-7}$cycloalkyl, $C_{1-4}$alkyloxy, formyl, polyhalo$C_{1-4}$alkyl, $NR^9R^{10}$, $C(=O)NR^9R^{10}$, $C(=O)-O-R^{14}$, $-O-R^6$, phenyl, $C(=O)$Het$^3$ and $C_{1-4}$alkyl substituted with one or more substituents each independently selected from halo, hydroxy, $C_{1-4}$alkyloxy, $C(=O)-Z-R^{14}$, Het$^3$ or $NR^9R^{10}$;

Het$^1$ is a monocyclic heterocycle selected from pyrrolyl, imidazolyl, pyrazolyl, triazolyl, tetrazolyl, furanyl, thienyl, oxazolyl, isoxazolyl, thiazolyl, isothiazolyl, thiadiazolyl, oxadiazolyl, pyridinyl, pyrimidinyl, pyrazinyl, pyranyl, pyridazinyl and triazinyl, in particular imidazolyl, oxadiazolyl, thiazolyl, pyrimidinyl or pyridinyl, wherein said monocyclic heterocycles each independently may optionally be substituted with one, or where possible, two or three substituents each independently selected from Het$^2$, $R^{11}$ and $C_{1-4}$alkyl optionally substituted with Het$^2$ or $R^{11}$; preferably Het$^1$ is imidazolyl, oxadiazolyl, thiazolyl or pyridinyl each independently and optionally substituted with one, or where possible, two or three substituents each independently selected from Het$^2$, $R^{11}$ and $C_{1-4}$alkyl optionally substituted with Het$^2$ or $R^{11}$;

Het$^2$ is an aromatic heterocycle; more in particular furanyl, thienyl, pyridinyl or benzothienyl, wherein said aromatic heterocycles each independently may optionally be substituted with one, or where possible, two or three substituents each independently selected from $R^{11}$ and $C_{1-4}$alkyl;

Het$^3$ is piperidinyl, piperazinyl, morpholinyl and tetrahydropyranyl each independently and optionally substituted with, where possible, one, two, three or four substituents each independently selected from hydroxy, $C_{1-4}$alkyl, $C_{1-4}$alkylcarbonyl, piperidinyl and $C_{1-4}$alkyl substituted with one or two substituents independently selected from hydroxy, $C_{1-4}$alkyloxy and phenyl;
Het$^4$ is thienyl.

Special compounds are those compounds of formula (I') wherein p is 2 and both $R^1$ substituents are chloro; more preferably the two chloro substituents are in the ortho positions relative to the carbon atom bearing the —X—$R^2$, $R^3$ and $R^4$ substituents.

Particular compounds are those compounds of formula (I') wherein the 6-azauracil moiety is in the para position relative to the carbon atom bearing the —X—$R^2$, $R^3$ and $R^4$ substituents, and p is 2 whereby both $R^1$ substituents are chloro positioned ortho relative to the carbon atom bearing the —X—$R^2$, $R^3$ and $R^4$ substituents.

Other particular compounds are those compounds of formula (I') wherein X is a direct bond and $R^2$ is a monocyclic heterocycle selected from pyrrolyl, imidazolyl, pyrazolyl, triazolyl, tetrazolyl, furanyl, thienyl, oxazolyl, isoxazolyl, thiazolyl, isothiazolyl, thiadiazolyl, oxadiazolyl, pyridinyl, pyrimidinyl, pyrazinyl, pyranyl, pyridazinyl and triazinyl, in particular imidazolyl, oxadiazolyl, thiazolyl, pyrimidinyl or pyridinyl, wherein said monocyclic heterocycles each independently may optionally be substituted with one, or where possible, two or three substituents each independently selected from Het$^2$, $R^{11}$ and $C_{1-4}$alkyl optionally substituted with Het$^2$ or $R^{11}$; more in particular $R^2$ is optionally substituted thiazolyl, pyridinyl or oxadiazolyl.

Preferred compounds are those compounds of formula (I') wherein $R^3$ and $R^4$ are both methyl and —X—$R^2$ is Het$^1$ wherein Het$^1$ suitably is optionally substituted thiazolyl, pyridinyl or oxadiazolyl.

More preferred compounds are those compounds of formula (I') wherein $R^3$ and $R^4$ are both methyl, —X—$R^2$ is optionally substituted 2-thiazolyl or 3-oxadiazolyl, the 6-azauracil moiety is in the para position relative to the carbon atom bearing the —X—$R^2$, $R^3$ and $R^4$ substituents, and p is 2 whereby both $R^1$ substituents are chloro positioned ortho relative to the carbon atom bearing the —X—$R^2$, $R^3$ and $R^4$ substituents.

Examples of compounds of formula (I) further includes compounds of formula (I in which p, X, Y $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, m, n, q, r, s $R^a$, $R^b$, $R^c$, $R^d$, $R^e$, $R^f$, $R^g$, $R_h$, $R_k$, $R_i$, $R_j$, $R_m$, $R_n$, $R^{15}$, $R^{16}$, $R^{17}$, $R^{18}$, Z, aryl, 'Het$^1$, Het$^2$, Het$^3$, Het$^4$, Het$^5$ as used in relation to compounds of formula (I") have the meanings below:

The present invention is concerned with the compounds of formula

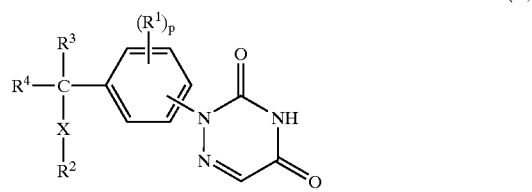

(I")

the N-oxides, the pharmaceutically acceptable addition salts and the stereochemically isomeric forms thereof, wherein:

p represents an integer being 0, 1, 2, 3 or 4;
X represents O, S, NR$^5$ or a direct bond or —X—$R^2$ taken together may represent cyano;
Y represents O, S, NR$^5$, or S(O)$_2$;
each $R^1$ independently represents C(=O)·Z—$R^{14}$, $C_{1-6}$alkyl, halo, polyhalo$C_{1-6}$alkyl, hydroxy, mercapto, $C_{1-6}$alkyloxy, $C_{1-6}$alkylthio, $C_{1-6}$alkylcarbonyloxy, aryl, cyano, nitro, Het$^3$, $R^6$, NR$^7$R$^8$ or $C_{1-4}$alkyl substituted with C(=O)—Z·$R^{14}$, Het$^3$, $R^6$ or NR$^7$R$^8$;

R represents Het$^1$, $C_{3-7}$cycloalkyl optionally substituted with C(=O)—Z—$R^{14}$, $C_{1-6}$alkyl or $C_{1-6}$alkyl substituted with one or two substituents selected from C(=O)·Z—$R^{14}$, hydroxy, cyano, amino, mono- or di($C_{1-4}$alkyl)amino, $C_{1-6}$alkyloxy optionally substituted with C(=O)—Z—$R^{14}$, $C_{1-6}$alkylsulfonyloxy, $C_{3-7}$cycloalkyl optionally substituted with C(=O)—Z—$R^{14}$, aryl, aryloxy, arylthio, Het$^1$, Het$^1$oxy and Het$^1$thio; and if X is O, S or NR$^5$, then $R^2$ may also represent aminothiocarbonyl, $C_{1-4}$alkylcarbonyl optionally substituted with C(=O)—Z—$R^{14}$, $C_{1-4}$alkylthiocarbonyl optionally substituted with C(=O)—Z—$R^{14}$, arylcarbonyl, arylthiocarbonyl, Het$^1$carbonyl or Het$^1$thiocarbonyl;

$R^3$ represents hydrogen, $C_{1-6}$alkyl or $C_{3-7}$cycloalkyl;
$R^4$ represents hydrogen, $C_{1-6}$alkyl or $C_{3-7}$cycloalkyl; or
$R^3$ and $R^4$ taken together form a $C_{2-6}$alkanediyl;
$R^5$ represents hydrogen or $C_{1-4}$alkyl;

each $R^6$ independently represents $C_{1-6}$alkylsulfonyl, aminosulfonyl, piperidinylsulfonyl, mono- or di($C_{1-4}$alkyl)aminosulfonyl, mono- or di(benzyl)aminosulfonyl, polyhalo$C_{1-6}$alkylsulfonyl, $C_{1-6}$alkylsulfinyl, phenyl$C_{1-4}$alkylsulfonyl, piperazinylsulfonyl, aminopiperidinylsulfonyl, piperidinylaminosulfonyl, N—$C_{1-4}$alkyl-N-piperidinylaminosulfonyl or mono- or di($C_{1-4}$alkyl)amino$C_{1-4}$alkylsulfonyl;

each $R^7$ and each $R^8$ are independently selected from hydrogen, $C_{1-4}$alkyl, hydroxy$C_{1-4}$alkyl, dihydroxy$C_{1-4}$alkyl, aryl, aryl$C_{1-4}$alkyl, $C_{1-4}$alkyloxy$C_{1-4}$alkyl, $C_{1-4}$alkylcarbonyl, arylcarbonyl, Het$^3$carbonyl, mono- or di($C_{1-4}$alkyl)amino$C_{1-4}$alkyl, arylaminocarbonyl, arylaminothiocarbonyl, Het$^3$aminocarbonyl, Het$^3$aminothiocarbonyl, $C_{3-7}$cycloalkyl, pyridinyl$C_{1-4}$alkyl, $C_{1-4}$alkanediylC(=O)—Z—$R^{14}$, —C(=O)—Z—$R^{14}$, —Y—$C_{1-4}$alkanediyl-C(=O)—Z—$R^{14}$, Het$^3$, Het$^4$ and $R^6$; or $R^7$ and $R^8$ taken together with the nitrogen atom to which they are attached form a radical of formula

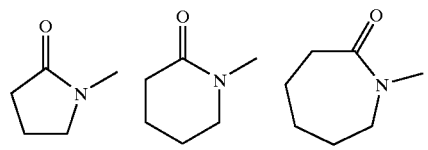

$R^9$ and $R^{10}$ are each independently selected from hydrogen, $C_{1-4}$alkyl, hydroxy$C_{1-4}$alkyl, dihydroxy$C_{1-4}$alkyl, phenyl, phenyl$C_{1-4}$alkyl, $C_{1-4}$alkyloxy$C_{1-4}$alkyl, $C_{1-4}$alkylcarbonyl, phenylcarbonyl, Het$^3$carbonyl, mono- or di($C_{1-4}$alkyl)amino$C_{1-4}$alkyl, phenylaminocarbonyl, phenylaminothiocarbonyl, Het$^3$aminocarbonyl, Het$^3$aminothiocarbonyl, $C_{3-7}$cycloalkyl, pyridinyl$C_{1-4}$alkyl, $C_{1-4}$alkanediyl-C(=O)—Z—$R^{14}$, —C(=O)—Z—$R^{14}$, —Y—$C_{1-4}$alkanediyl-C(=O)—Z—$R^{14}$, Het$^3$, Het$^4$ and $R^6$; or $R^9$ and $R^{10}$ taken together with the nitrogen atom to which they are attached form a radical of formula

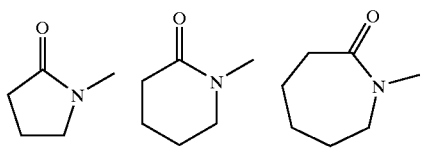

each R¹¹ independently being selected from hydroxy, mercapto, cyano, nitro, halo, trihalomethyl, $C_{1-4}$alkyloxy optionally substituted with $C(=O)-Z-R^{14}$, formyl, trihalo$C_{1-4}$alkylsulfonyloxy, $R^6$, $NR^7R^8$, $C(=O)NR^{15}R^{16}$, $-C(=O)-Z-R^{14}-Y-C_{1-4}$alkanediyl-$C(=O)-Z-R^{14}$, aryl, aryloxy, arylcarbonyl, $C_{3-7}$cycloalkyl optionally substituted with $C(=O)-Z-R^{14}$, $C_{3-7}$cycloalkyloxy optionally substituted with $C(=O)-Z-R^{14}$, phthalimide-2-yl, Het³ and $C(=O)$Het³;

$R^{12}$ and $R^{13}$ are each independently selected from hydrogen, $C_{1-4}$alkyl, hydroxy$C_{1-4}$alkyl, dihydroxy$C_{1-4}$alkyl, phenyl, phenyl$C_{1-4}$alkyl, $C_{1-4}$alkyloxy$C_{1-4}$alkyl, $C_{1-4}$alkylcarbonyl, phenylcarbonyl, mono- or di($C_{1-4}$alkyl)amino$C_{1-4}$alkyl, phenylaminocarbonyl, phenylaminothiocarbonyl, $C_{3-7}$cycloalkyl, pyridinyl$C_{1-4}$alkyl, $C_{1-4}$alkanediyl-$C(=O)-Z-R^{14}$, $-C(=O)-Z-R^{14}$, $-Y-C_{1-4}$alkanediyl-$C(=O)-Z-R^{14}$ and $R^6$; or $R^{12}$ and $R^{13}$ taken together with the nitrogen atom to which they are attached form a radical of formula

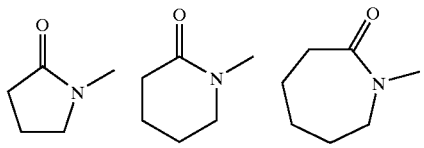

each R¹⁴ independently represents hydrogen, $C_{1-20}$acyl (having a straight or branched, saturated or unsaturated hydrocarbon chain having 1 to 20 carbon atoms), $C_{1-20}$alkyl, $C_{3-20}$alkenyl optionally substituted with phenyl, $C_{3-20}$alkynyl, $C_{3-7}$ cycloalkyl, polyhalo$C_{1-20}$alkyl, Het⁵, phenyl or $C_{1-20}$ alkyl substituted with one or more substituents selected from hydroxy, $NR^{17}R^{18}$, phenyl, mono- or di-($C_{1-4}$alkyl)amino, cyano, Het⁵, $C_{1-4}$ alkyloxycarbonyl, phenyl $C_{1-4}$ alkyloxycarbonyl and $C_{3-7}$ cycloalkyl, or $R^{14}$ represents a radical of formula

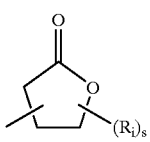 (a)

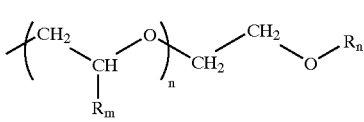 (b)

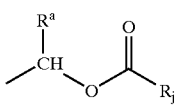 (c)

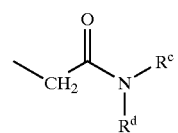 (d)

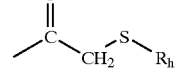 (e)

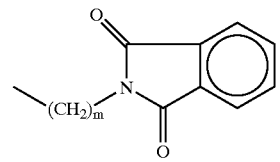 (h)

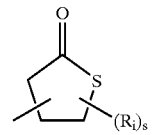 (i)

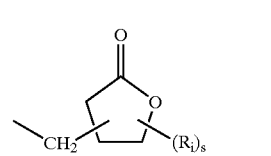 (j)

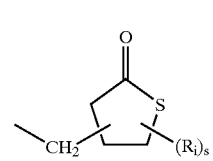 (k)

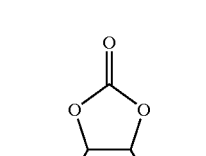 (l)

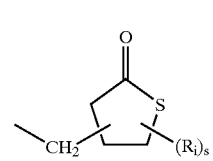 (m)

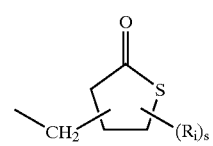 (n)

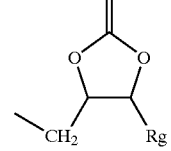 (o)

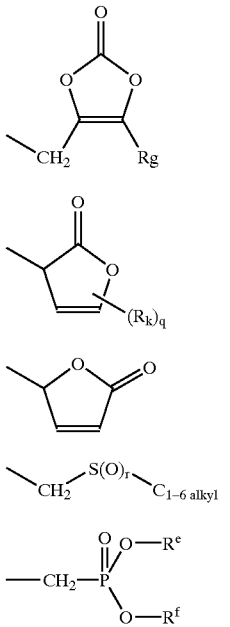

(p)

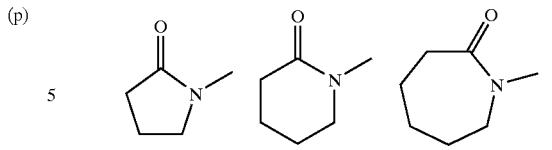

(q)

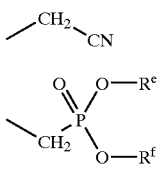

wherein m is 1 to 4, n is 0 to 5, q is 0 to 2, r is 0 to 2 and s is 0 to 4;

$R^a$, $R^b$, $R^c$, $R^d$, $R^e$ and $R^f$ are each independently hydrogen, $C_{1-6}$alkyl, phenyl or $C_{3-7}$cycloalkyl; or $R^e$ and $R^f$ taken together may form —$CH_2$—$CH_2$—, —$CH_2$—$CH_2$—$CH_2$— or —$CH_2$—$CH_2$—$CH_2$—$CH_2$—;

$R_g$, $R_h$ and $R_k$ are each independently hydrogen or $C_{1-4}$alkyl $R_i$ is $C_{1-4}$alkyl;

$R_j$ is —O—$R_b$, $C_{1-6}$alkyl, phenyl or $C_{3-7}$cycloalkyl optionally substituted with $C_{1-4}$ alkyloxy;

where $R_m$ is hydrogen or $C_{1-4}$ alkyloxy and $R_n$ is hydrogen, $C_{1-4}$alkyl, $C_{3-7}$cycloalkyl, phenyl or phenyl$C_{1-4}$alkyl each Z independently represents O, S, NH, —$CH_2$—O— or —$CH_2$—S— whereby —$CH_2$— is attached to the carbonyl group; or —Z—$R^{14}$ taken together form a radical of formula (f)

$\diagup^{CH_2}\diagdown_{CN}$ (g)

$\underset{CH_2}{\overset{O}{\diagdown}}\overset{O—R^e}{\underset{O—R^f}{P}}$ $R^{15}$ and $R^{16}$ are each independently selected from hydrogen, $C_{1-4}$alkyl, hydroxy$C_{1-4}$alkyl, dihydroxy$C_{1-4}$alkyl, aryl, aryl$C_{1-4}$alkyl, $C_{1-4}$alkyloxy$C_{1-4}$alkyl, —C(=O)—Z—$R^{14}$, arylcarbonyl, mono- or di($C_{1-4}$alkyl)amino$C_{1-4}$alkyl, arylaminocarbonyl, arylaminothiocarbonyl, aminocarbonylmethylene, mono- or di($C_{1-4}$alkyl)aminocarbonylmethylene, $Het^3$aminocarbonyl, $Het^3$aminothiocarbonyl, pyridinyl$C_{1-4}$alkyl, $Het^3$ or $R^6$; or $R^{15}$ and $R^{16}$ taken together with the nitrogen atom to which they are attached form a radical of formula $R^{17}$ and $R^{18}$ are each independently selected from hydrogen, $C_{1-4}$alkyl, hydroxy$C_{1-4}$alkyl, dihydroxy$C_{1-4}$alkyl, phenyl, phenyl$C_{1-4}$alkyl, $C_{1-4}$alkyloxy$C_{1-4}$alkyl, $C_{1-4}$alkylcarbonyl, phenylcarbonyl, mono- or di($C_{1-4}$alkyl)amino$C_{1-4}$alkyl, phenylaminocarbonyl, phenylaminothiocarbonyl, $C_{3-7}$cycloalkyl, pyridinyl$C_{1-4}$alkyl, $C_{1-4}$alkanediyl-C(=O)—Z—$C_{1-6}$alkyl, —C(=O)—Z—$C_{1-6}$alkyl, —Y—$C_{1-4}$alkanediyl-C(=O)—Z—$C_{1-6}$alkyl and $R^6$;

aryl represents phenyl optionally substituted with one, two or three substituents each independently selected from nitro, azido, cyano, halo, hydroxy, $C_{1-4}$alkyl, $C_{3-7}$cycloalkyl, $C_{1-4}$alkyloxy, formyl, polyhalo$C_{1-4}$alkyl, $NR^9R^{10}$, C(=O)$NR^9R^{10}$, C(=O)—Z—$R^{14}$ $R^6$, —O—$R^6$, phenyl, $Het^3$, C(=O)$Het^3$ and $C_{1-4}$alkyl substituted with one or more substituents each independently selected from halo, hydroxy, $C_{1-4}$alkyloxy, C(=O)—Z—$R^{14}$, —Y—$C_{1-4}$alkanediyl-C(=O)—Z—$R^{14}$, $Het^3$ or $NR^9R^{10}$;

$Het^1$ represents a heterocycle selected from pyrrolyl, pyrrolinyl, imidazolyl, imidazolinyl, pyrazolyl, pyrazolinyl, triazolyl, tetrazolyl, furanyl, tetrahydrofuranyl, thienyl, thiolanyl, dioxolanyl, oxazolyl, oxazolinyl, isoxazolyl, thiazolyl, thiazolinyl, isothiazolyl, thiadiazolyl, oxadiazolyl, pyridinyl, pyrimidinyl, pyrazinyl, pyranyl, pyridazinyl, pyrrolidinyl, piperidinyl, piperazinyl, morpholinyl, thiomorpholinyl, dioxanyl, dithianyl, trithianyl, triazinyl, benzothienyl, isobenzothienyl, benzofuranyl, isobenzofuranyl, benzothiazolyl, benzoxazolyl, benzodioxanyl, indolyl, isoindolyl, indolinyl, purinyl, 1H-pyrazolo[3,4-d]pyrimidinyl, benzimidazolyl, quinolyl, isoquinolyl, cinnolinyl, phtalazinyl, quinazolinyl, quinoxalinyl, thiazolopyridinyl, oxazolopyridinyl and imidazo[2,1-b]thiazolyl; wherein said heterocycles each independently may optionally be substituted with one, or where possible, two or three substituents each independently selected from $Het^2$, $R^{11}$ and $C_{1-4}$alkyl optionally substituted with one or two substituents independently selected from $Het^2$ and $R^{11}$;

$Het^2$ represents a heterocycle selected from pyrrolyl, pyrrolinyl, imidazolyl, imidazolinyl, pyrazolyl, pyrazolinyl, triazolyl, tetrazolyl, furanyl, tetrahydrofuranyl, thienyl, thiolanyl, dioxolanyl, oxazolyl, oxazolinyl, isoxazolyl, thiazolyl, thiazolinyl, isothiazolyl, thiadiazolyl, oxadiazolyl, pyridinyl, pyrimidinyl, pyrazinyl, pyranyl, pyridazinyl, dioxanyl, dithianyl, trithianyl, triazinyl, benzothienyl, isobenzothienyl, benzofuranyl, isobenzofuranyl, benzothiazolyl, benzoxazolyl, indolyl, isoindolyl, indolinyl, purinyl, 1H-pyrazolo[3,4-d]pyrimidinyl, benzimidazolyl, quinolyl, isoquinolyl, cinnolinyl, phtalazinyl, quinazolinyl, quinoxalinyl, thiazolopyridinyl, oxazolopyridinyl and imidazo[2,1-b]thiazolyl; wherein said heterocycles each independently may optionally be substituted with one, or where possible, two or three substituents each independently selected from $Het^4$, $R^{11}$ and $C_{1-4}$alkyl optionally substituted with one or two substituents independently selected from $Het^4$ and $R^{11}$;

Het³ represents a monocyclic heterocycle selected from pyrrolidinyl, piperidinyl, piperazinyl, morpholinyl, thiomorpholinyl and tetrahydropyranyl; wherein said monocyclic heterocycles each independently may optionally be substituted with, where possible, one, two, three or four substituents each independently selected from hydroxy, $C_{1-4}$alkyl, $C_{1-4}$alkyloxy, $C_{1-4}$alkylcarbonyl, piperidinyl, $NR^{12}R^{13}$, $C(=O)-Z-R^{14}$, $R^6$ and $C_{1-4}$alkyl substituted with one or two substituents independently selected from hydroxy, $C_{1-4}$alkyloxy, phenyl, $C(=O)-Z-R^{14}$, $-Y-C_{1-4}$alkanediyl-$C(=O)-Z-R^{14}$, $R^6$ and $NR^{12}R^{13}$;

Het⁴ represents a monocyclic heterocycle selected from pyrrolyl, imidazolyl, pyrazolyl, triazolyl, tetrazolyl, furanyl, thienyl, oxazolyl, isoxazolyl, thiazolyl, isothiazolyl, thiadiazolyl, oxadiazolyl, pyridinyl, pyrimidinyl, pyrazinyl, pyranyl, pyridazinyl and triazinyl;

Het⁵ represents a heterocycle selected from pyrrolyl, pyrrolinyl, imidazolyl, imidazolinyl, pyrazolyl, pyrazolinyl, triazolyl, tetrazolyl, furanyl, tetrahydrofuranyl, thienyl, thiolanyl, dioxolanyl, oxazolyl, oxazolinyl, isoxazolyl, thiazolyl, thiazolinyl, isothiazolyl, thiadiazolyl, oxadiazolyl, pyridinyl, pyrimidinyl, pyrazinyl, pyranyl, pyridazinyl, pyrrolidinyl, piperidinyl, piperazinyl, morpholinyl, thiomorpholinyl, tetrahydropyranyl, dioxanyl, dithianyl, trithianyl, triazinyl, benzothienyl, isobenzothienyl, benzofuranyl, isobenzofuranyl, benzothiazolyl, benzoxazolyl, benzodioxanyl, indolyl, isoindolyl, indolinyl, purinyl, 1H-pyrazolo[3,4-d]pyrimidinyl, benzimidazolyl, quinolyl, isoquinolyl, cinnolinyl, phtalazinyl, quinazolinyl, quinoxalinyl, thiazolopyridinyl, oxazolopyridinyl and imidazo[2,1-b]thiazolyl; wherein said heterocycles each independently may be substituted with, where possible, one, two, three or four substituents each independently selected from hydroxy, $C_{1-4}$alkyl, $C_{1-4}$alkyloxy, $C_{1-4}$alkylcarbonyl, piperidinyl, $NR^{17}R^{18}$, $C(=O)-Z-C_{1-6}$alkyl, $R^6$, sulfonamido and $C_{1-4}$alkyl substituted with one or two substituents independently selected from hydroxy, $C_{1-4}$alkyloxy, phenyl, $C(=O)-Z-C_{1-6}$alkyl, $-Y-C_{1-4}$alkanediyl-$C(=O)-Z-C_{1-6}$alkyl, $R^6$ and $NR^{17}R^{18}$; provided however that $R^2$ is other than $C_{1-6}$ alkyloxycarbonyl$C_{1-6}$alkyl or aminocarbonyl; and $R^7$, $R^8$, $R^9$ and $R^{10}$ are other than aminocarbonyl, $C_{1-4}$alkylcarbonyloxy-$C_{1-4}$alkylcarbonyl, hydroxy $C_{1-4}$alkylcarbonyl, $C_{1-4}$alkyloxycarbonylcarbonyl, $C(=O)-O-R^{19}$, $C_{1-4}$alkanediyl$C(=O)-O-R^{19}$ or $-Y-C_{1-4}$alkanediyl$C(=O)-O-R^{19}$; and $R^{12}$ and $R^{13}$ are other than $C_{1-4}$alkylcarbonyloxy-$C_{1-4}$alkylcarbonyl, hydroxy $C_{1-4}$alkylcarbonyl or $C_{1-4}$alkylcarbonylcarbonyl; and $R^{11}$ is other than $C(=O)-O-R^{19}$, $Y-C_{1-4}$alkanediyl $-C(=O)-OR^{19}$, $C(=O)NH_2$, $C(=O)NHC_{1-4}$alkyl or $C(=O)NHC_{3-7}$cycloalkyl; and $R^{15}$ and $R^{16}$ are other than aminocarbonyl, $C_{1-4}$alkylcarbonyloxy-$C_{1-4}$alkylcarbonyl, hydroxy $C_{1-4}$alkylcarbonyl or $C_{1-4}$alkyloxycarbonylcarbonyl; and aryl is other than phenyl substituted with $C(=O)-O-R^{19}$, $C(=O)NH_2$, $C(=O)NHC_{1-4}$alkyl, $C(=O)NHC_{3-7}$cycloalkyl and/or with $C_{1-4}$alkyl substituted with $C(=O)-O-R^{19}$ or $Y-C_{1-4}$alkanediyl $-C(=O)-O-R^{14}$; and Het³ is other than a monocyclic heterocycle substituted with $C(=O) \cdot O-R^{19}$ and/or with $C_{1-4}$alkyl substituted with $C(=O)-O-R^{19}$ and/or $Y-C_{1-4}$alkanediyl $(=O)-O-R^{19}$; and in each of the above proviso's $R^{19}$ is defined as hydrogen, $C_{1-4}$alkyl, $C_{3-7}$cycloalkyl, aminocarbonylmethylene or mono- or di($C_{1-4}$alkyl)aminocarbonylmethylene; and the said compound of formula (I) contains at least one $-C(=O)-Z-R^{14}$ moiety.

An interesting group of compounds are those compounds of formula (I″) wherein the 6-azauracil moiety is connected to the phenyl ring in the para or meta position relative to the carbon atom bearing the $-X-R^2$, $R^3$ and $R^4$ substituents; preferably in the para position. Another interesting group contains those compounds of formula (I″) wherein one or more of the following restrictions apply:

p is 0, 1 or 2;

X is S, $NR^5$ or a direct bond; more preferably a direct bond;

each $R^1$ independently is halo, polyhalo$C_{1-6}$alkyl, $C_{1-6}$alkyl, $C_{1-6}$alkyloxy or aryl, preferably, chloro or trifluoromethyl, more preferably chloro;

the at least one $-C(=O)-Z-R^{14}$ moiety contained by the compound of formula (I″) is born by $R^2$;

$R^2$ is Het¹ or $C_{1-6}$alkyl substituted with one or two substituents selected from hydroxy, cyano, amino, mono- or di($C_{1-4}$alkyl)amino, $C(=O)-Z-R^{14}$, $C_{1-6}$alkyloxy optionally substituted with $C(=O)-Z-R^{14}$, $C_{1-6}$alkylsulfonyloxy, $C_{3-7}$cycloalkyl optionally substituted with $C(=O)-Z-R^{14}$, aryl, aryloxy, arylthio, Het¹, Het¹oxy and Het¹thio; and if X is O, S or $NR^5$, then $R^2$ may also represent aminothiocarbonyl, $C_{1-4}$alkylcarbonyl optionally substituted with $C(=O)-Z-R^{14}$, $C_{1-4}$alkylthiocarbonyl optionally substituted with $C(=O)-Z-R^{14}$, arylcarbonyl, arylthiocarbonyl, Het¹carbonyl or Het¹thiocarbonyl; more preferably $R^2$ is Het¹;

$R^3$ is hydrogen, methyl, ethyl, propyl or cyclohexyl, more preferably methyl;

$R^4$ is hydrogen or methyl, more preferably methyl;

$R^3$ and $R^4$ are taken together to form a 1,4-butanediyl;

$R^6$ is $C_{1-6}$alkylsulfonyl or aminosulfonyl;

$R^7$ and $R^8$ are each independently hydrogen, $C_{1-4}$alkyl, Het³ or $R^6$;

$R^9$ and $R^{10}$ are each independently hydrogen, $C_{1-4}$alkyloxy$C_{1-4}$alkyl, $C_{1-4}$alkylcarbonyl, aminocarbonyl, Het³carbonyl, Het³ or $R^6$;

$R^{11}$ is cyano, nitro, halo, $C_{1-4}$alkyloxy, formyl, $NR^7R^3$, $C(=O)NR^{15}R^{16}$, $-C(=O)-Z-R^{14}$, aryl, arylcarbonyl, Het³ or $C(=O)$Het³; more preferably $R^{11}$ is phenyl, $-C(=O)-O-R^{14}$, $-C(=O)-S-R^{14}$ or $-C(=O)-NH-R^{14}$, $R^{14}$ is dihydrofuranyl, $C_{5-20}$alkyl, $C_{3-20}$alkenyl, polyhalo$C_{1-6}$alkyl, Het⁵ or $C_{1-20}$alkyl substituted with one or more substituents selected from phenyl, $C_{1-4}$alkylamino, cyano, Het¹, hydroxy and $C_{3-7}$cycloalkyl;

$R^{17}$ and $R^{18}$ are each independently hydrogen or phenyl;

aryl is phenyl optionally substituted with one, two or three substituents each independently selected from nitro, cyano, halo, hydroxy, $C_{1-4}$alkyl, $C_{3-7}$cycloalkyl, $C_{1-4}$alkyloxy, formyl, polyhalo$C_{1-4}$alkyl, $NR^9R^{10}$, $C(=O)NR^9R^{10}$, $C(=O)-O-R^{14}$, $-O-R^6$, phenyl, $C(=O)$Het³ and $C_{1-4}$alkyl substituted with one or more substituents each independently selected from halo, hydroxy, $C_{1-4}$alkyloxy, $C(=O)-Z-R^{14}$, Het³ and $NR^9R^{10}$;

Het$^1$ is a monocyclic heterocycle selected from pyrrolyl, imidazolyl, pyrazolyl, triazolyl, tetrazolyl, furanyl, thienyl, oxazolyl, isoxazolyl, thiazolyl, isothiazolyl, thiadiazolyl, oxadiazolyl, pyridinyl, pyrimidinyl, pyrazinyl, pyranyl, pyridazinyl and triazinyl, in particular imidazolyl, oxadiazolyl, thiazolyl, pyrimidinyl or pyridinyl, wherein said monocyclic heterocycles each independently may optionally be substituted with one, or where possible, two or three substituents each independently selected from Het$^2$, R$^{11}$ and C$_{1-4}$alkyl optionally substituted with Het$^2$ or R$^{11}$; more preferably Het$^1$ is imidazolyl, oxadiazolyl, thiazolyl or pyridinyl each independently and optionally substituted with one, or where possible, two or three substituents each independently selected from Het$^2$, R$^{11}$ and C$_{1-4}$alkyl optionally substituted with Het$^2$ or R$^{11}$;

Het$^2$ is an aromatic heterocycle; more in particular furanyl, thienyl, pyridinyl or benzothienyl, wherein said aromatic heterocycles each independently may optionally be substituted with one, or where possible, two or three substituents each independently selected from R$^{11}$ and C$_{1-4}$alkyl;

Het$^3$ is piperidinyl, piperazinyl, morpholinyl or tetrahydropyranyl each independently and optionally substituted with, where possible, one, two, three or four substituents each independently selected from hydroxy, C$_{1-4}$alkyl, C$_{1-4}$alkylcarbonyl, piperidinyl and C$_{1-4}$alkyl substituted with one or two substituents independently selected from hydroxy, C$_{1-4}$alkyloxy and phenyl;

Het$^4$ is thienyl;

Het$^5$ is piperidinyl or piperazinyl optionally substituted with C$_{1-4}$alkyl or sulfonamido.

Special compounds are those compounds of formula (I") wherein p is 2 and both R$^1$ substituents are chloro; more preferably the two chloro substituents are in the ortho positions relative to the carbon atom bearing the —X—R$^2$, R$^3$ and R$^4$ substituents.

Particular compounds are those compounds of formula (I") wherein the 6-azauracil moiety is in the para position relative to the carbon atom bearing the —X—R$^2$, R$^3$ and R$^4$ substituents, and p is 2 whereby both R$^1$ substituents are chloro positioned ortho relative to the carbon atom bearing the —X—R$^2$, R$^3$ and R$^4$ substituents.

Other particular compounds are those compounds of formula (I") wherein X is a direct bond and R$^2$ is a monocyclic heterocycle selected from pyrrolyl, imidazolyl, pyrazolyl, triazolyl, tetrazolyl, furanyl, thienyl, oxazolyl, isoxazolyl, thiazolyl, isothiazolyl, thiadiazolyl, oxadiazolyl, pyridinyl, pyrimidinyl, pyrazinyl, pyranyl, pyridazinyl and triazinyl, in particular imidazolyl, oxadiazolyl, thiazolyl, pyrimidinyl or pyridinyl, wherein said monocyclic heterocycles each independently may optionally be substituted with one, or where possible, two or three substituents each independently selected from Het$^2$, R$^{11}$ and C$_{1-4}$alkyl optionally substituted with Het$^2$ or R$^{11}$; more in particular R$^2$ is optionally substituted thiazolyl, pyridinyl or oxadiazolyl.

Preferred compounds are those compounds of formula (I") wherein R$^3$ and R$^4$ are both methyl and —X—R$^2$ is Het$^1$ wherein Het$^1$ suitably is optionally substituted thiazolyl, pyridinyl or oxadiazolyl.

More preferred compounds are those compounds of formula (I") wherein R$^3$ and R$^4$ are both methyl, —X—R$^2$ is optionally substituted 2-thiazolyl or 3-oxadiazolyl, the 6-azauracil moiety is in the para position relative to the carbon atom bearing the —X—R$^2$, R$^3$ and R$^4$ substituents, and p is 2 whereby both R$^1$ substituents are chloro positioned ortho relative to the carbon atom bearing the —X—R$^2$, R$^3$ and R$^4$ substituents.

In order to simplify the structural representation of the compounds of formula (I), the group

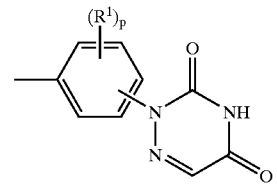

will hereinafter be represented by the symbol D.

Compounds of formula (I) can generally be prepared by a series of reactions comprising the step of reacting an intermediate of formula (II) wherein W$^1$ is a suitable leaving group such as, for example, a halogen atom, with an appropriate reagent of formula (III).

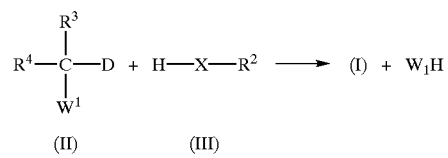

Said reaction may be performed in a reaction-inert solvent such as, for example, acetonitrile, N,N-dimethylformamide, acetic acid, tetrahydrofuran, ethanol or a mixture thereof. Alternatively, in case the reagent of formula (III) acts as a solvent, no additional reaction-inert solvent is required. The reaction is optionally carried out in the presence of a base such as, for example, 1,8-diazabicyclo[5.4.0]undec-7-ene, sodium bicarbonate, sodiumethanolate and the like. Convenient reaction temperatures range between −70° C. and reflux temperature. In this and the following preparations, the reaction products may be isolated from the reaction medium and, if necessary, further purified according to methodologies generally known in the art such as, for example, extraction, crystallization, distillation, trituration and chromatography.

Some of the compounds and intermediates of the present invention can be prepared according to or analogous to the procedures described in EP-A-0,170,316, EP-A-0,232,932 and WO99/02505.

Alternatively, for instance, compounds of formula (I) may generally be prepared by cyclizing an intermediate of formula (IV) wherein L is a suitable leaving group such as, for example, C$_{1-6}$alkyloxy or halo, and E represents an appropriate electron attracting group such as, for example, an ester, an amide, a cyanide, C$_{1-6}$alkylsulfonyloxy and the like groups; and eliminating the group E of the thus obtained triazinedione of formula (V). The cyclization can suitably be carried out by refluxing the intermediate (IV) in acidic medium such as acetic acid and in the presence of a base such as, for example, potassium acetate.

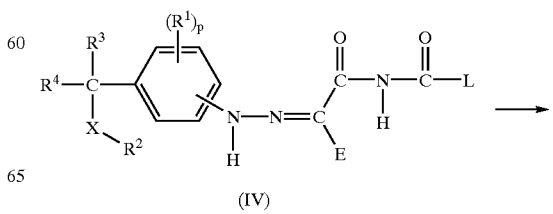

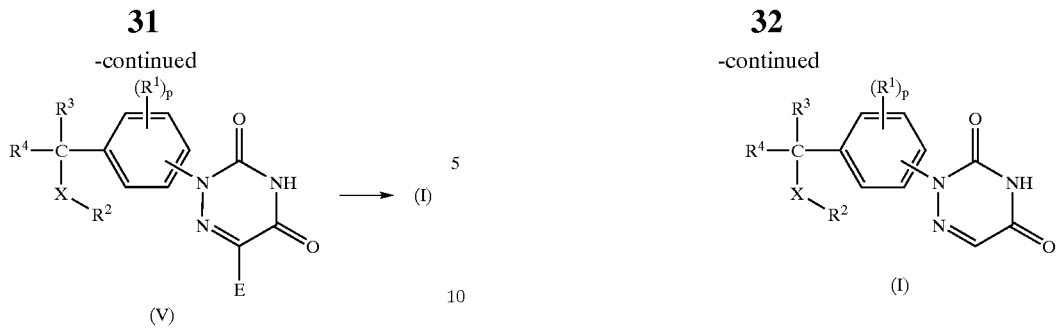

Depending on its nature, E can be eliminated using various art-known elimination procedures. For example when E is an amide or a cyano moiety, it can be hydrolized to a carboxylic moiety by for instance refluxing the intermediate bearing the E group in hydrochloric acid and acetic acid. The thus obtained intermediate can then be further reacted with mercaptoacetic acid or a functional derivative thereof to obtain a compound of formula (I). Said reaction is conveniently carried out at elevated temperatures ranging up to reflux temperature.

A suitable way to prepare intermediates of formula (IV) involves the reaction of an intermediate of formula (VI) with sodium nitrate or a functional derivative thereof in an acidic medium such as for example hydrochloric acid in acetic acid, and preferably in the same reaction mixture, further reacting the thus obtained intermediate with a reagent of formula (VII) wherein L and E are as defined above, in the presence of a base such as, for example, sodium acetate.

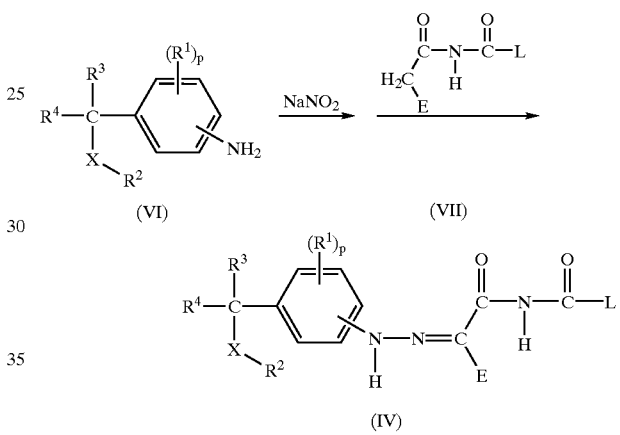

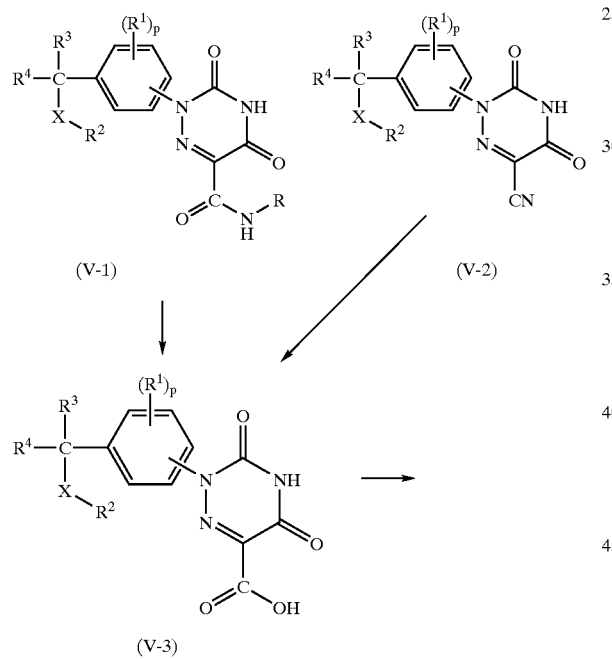

An interesting subgroup within the present invention are those compounds of formula (I) wherein —X—$R^2$ is an optionally substituted 2-thiazolyl moiety, said compounds being represented by formula (I-a). The optionally substituted 2-thiazolyl moiety can be incorporated in the compounds of formula (I-a) at different stages of the preparation process.

For instance, scheme 1 above depicts three possible ways to prepare compounds of formula (I-a).

Scheme 1

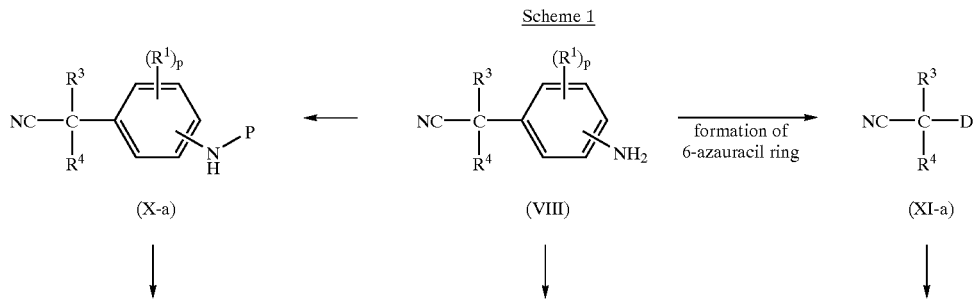

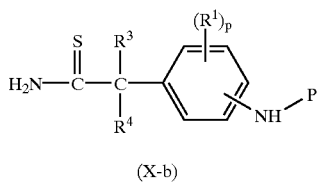 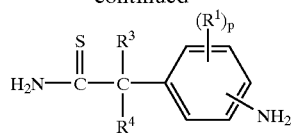 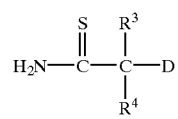

(X-b)   (IX-a)   (XI-b)

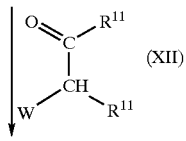 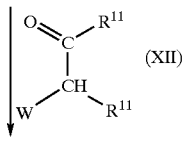

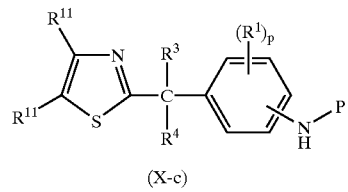 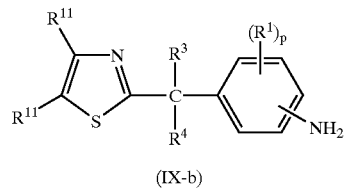 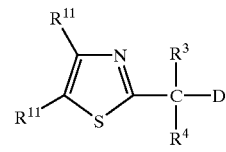

(X-c)   (IX-b)   (I-a)

| deprotection and formation of 6-azauracil ring | formation of 6-azauracil ring |

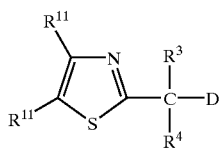 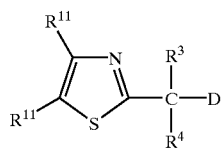

(I-a)   (I-a)

A first pathway involves the reaction of the cyano moiety in an intermediate of formula (VIII) to the corresponding thioamide using H$_2$S gas in a suitable solvent such as, for example, pyridine and in the presence of a base such as, for example, triethylamine, thus obtaining an intermediate of formula (IX-a). This thioamide can then be cyclized with an intermediate of formula (XII) wherein W is a suitable leaving group such as, for example, a halogen, e.g. bromo, in a suitable solvent such as, for example, ethanol. The amino moiety in the resulting 2-thiazolyl derivative of formula (IX-b) can then be further reacted as described hereinabove to form a 6-azauracil ring, thus obtaining a compound of formula (I-a).

A second pathway to form compounds of formula (I-a) involves first the protecting of the amino moiety in an intermediate of formula (VIII) by introducing a suitable protective group P such as, for example, an alkylcarbonyl group, using art-known protection techniques. In the example of P being a alkylcarbonyl group, the intermediates of formula (VII) can be reacted with the corresponding anhydride of formula alkyl-C(=O)—O—C(=O)-alkyl in an appropriate solvent such as, for example, toluene. The thus obtained intermediate of formula (X-a) can then be further reacted according to the first pathway described hereinabove. The final step, before formation of the 6-azauracil ring can be initiated after having deprotected the amino moiety using art-known deprotection techniques. In the example of P being a alkylcarbonyl group, the intermediates of formula (X-c) may be deprotected by reacting them in a suitable solvent such as, for example, ethanol, in the presence of an acid such as, for example, hydrochloric acid.

A third pathway involves first the formation of the 6-azauracil ring as described hereinabove but starting from an intermediate of formula (VIII), and subsequently reacting the thus formed intermediate of formula (XI-a) with H$_2$S and further reacting the thioamide of formula (XI-b) with an intermediate of formula (XII) as described in the first pathway, to finally form a compound of formula (I-a).

Another interesting subgroup within the present invention are those compounds of formula (I) wherein —X—R$^2$ is an optionally substituted 1,2,4-oxadiazol-3-yl moiety, said compounds being represented by formula (I-b-1). The optionally substituted 1,2,4-oxadiazol-3-yl moiety can be incorporated at the same stages of the reaction procedure as depicted for the 2-thiazolyl derivatives in scheme 1.

For instance, analogous to one of the three pathways shown in scheme 1, compounds of formula (I-b-1) can be prepared by reacting an intermediate of formula (VIII) as depicted in scheme 2.

Scheme 2

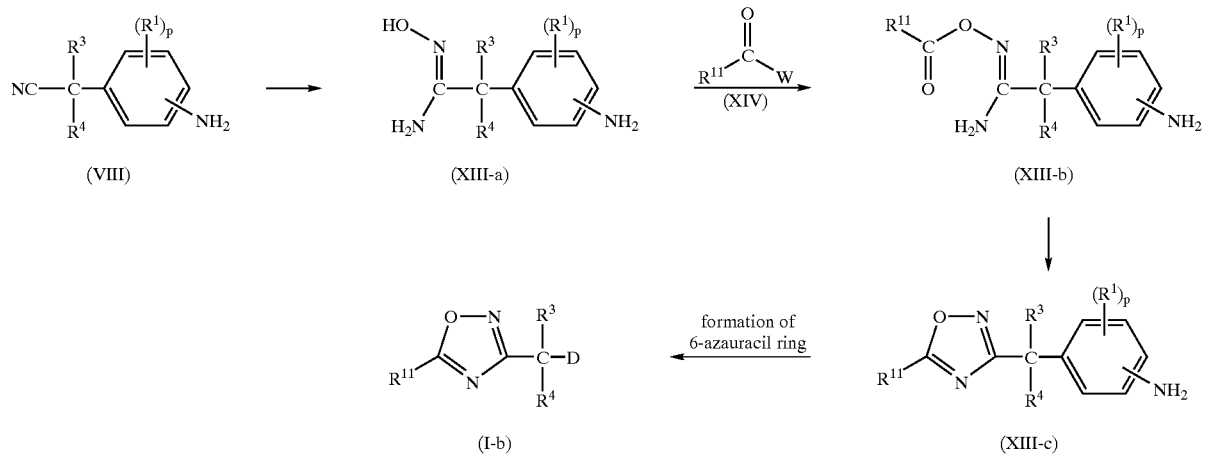

In said scheme 2, the cyano group of an intermediate of formula (VIII) is reacted with hydroxylamine or a functional derivative thereof in a suitable solvent such as, for example, methanol, and in the presence of a base such as, for example sodium methanolate. The thus formed intermediate of formula (XIII-a) is then reacted with an intermediate of formula (XIV) wherein W is a suitable leaving group such as, for example, a halogen, e.g. chloro, in an appropriate solvent such as, for example, dichloromethane, and in the presence of a base, such as, for example, N,N-(1-methylethyl) ethaneamine. The resulting intermediate of formula (XIII-b) is then cyclized to a 3-oxadiazolyl derivative of formula (XIII-c). The amino moiety in the intermediates of formula (XIII-c) can then be transformed to the 6-azauracil ring as described above.

Still another interesting subgroup within the present invention are those compounds of formula (I) wherein —X—R² is an optionally substituted 1,3,4-oxadiazol-2-yl moiety, said compounds being represented by formula (I-b-2).

For instance, compounds of formula (I-b-2) can be prepared as depicted in scheme 3.

Scheme 3

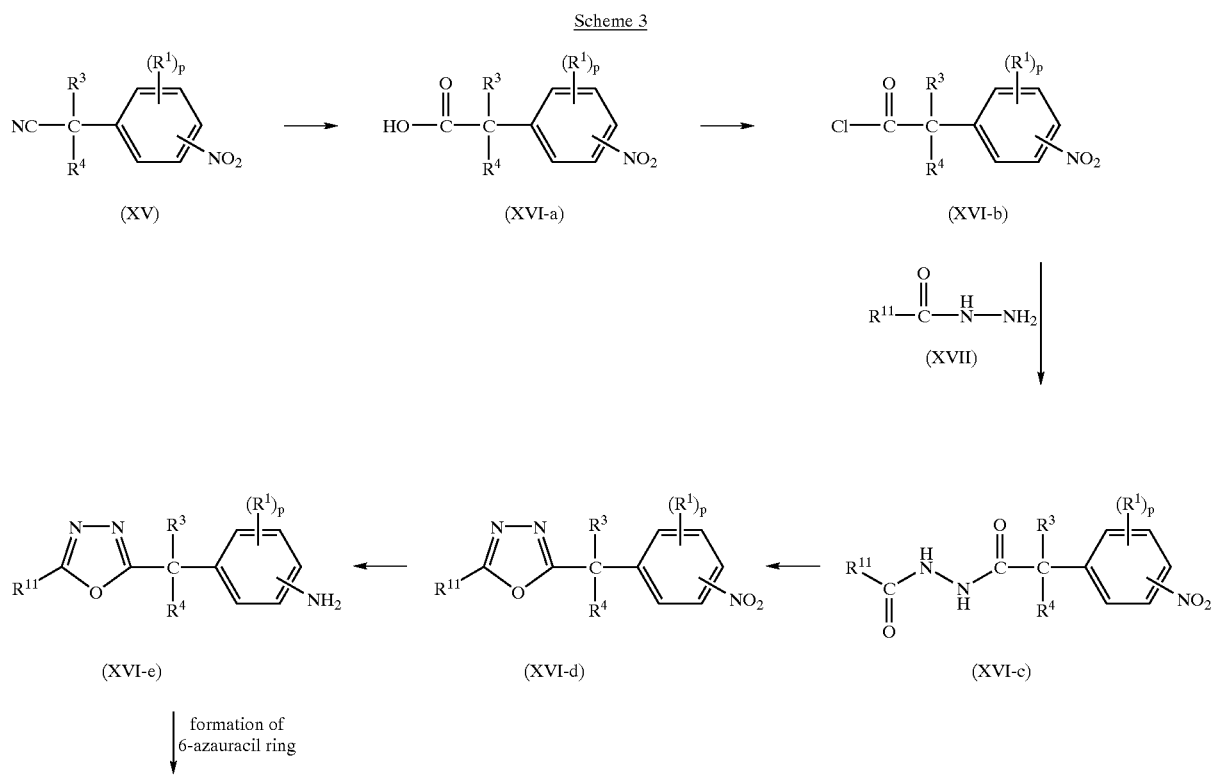

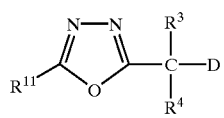

(I-b-2)

The nitrite moiety in an intermediate of formula (XV) is transformed into a carboxylic acid moiety using art-known techniques. For instance, the nitrite derivative may be refluxed in a mixture of sulfuric acid and acetic acid in water. The carboxylic acid derivative of formula (XVI-a) may be further be reacted with a chlorinating agent such as, for example, thionyl chloride, to form an acylchloride derivative of formula (XVI-b). Subsequently, The acyl chloride may be reacted with a hydrazine derivative of formula (XVII) in a suitable solvent such as, for example, dichloromethane, and in the presence of a base such as, for example N,N-(1-methylethyl)ethaneamine. The thus formed intermediate of formula (XVI-c) may be cyclized to a 1,2,4-oxadiazol-2-yl derivative of formula (XVI-d) in the presence of phophoryl chloride. As a final step before the formation of the 6-azauracil ring as described above, the nitro group in the intermediates of formula (XVI-e) is reduced to an amino group using art-known reduction techniques such as, for instance, reducing the nitro group with hydrogen in methanol and in the presence of a catalyst such as Raney Nickel.

Yet another interesting subgroup within the present invention are those compounds of formula (I) wherein —X—$R^2$ is —NH—$R^2$, said compounds being represented by formula (I-c-1). Scheme 4 depicts a suitable pathway to obtain compounds of formula (I-c-1).

Scheme 4

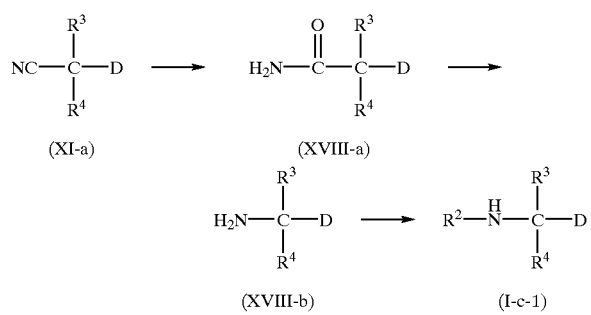

In said scheme 4, the cyano moiety of an intermediate of formula (XI-a) is hydrolized to the corresponding amide using art-known techniques such as, for instance, hydrolysis in the presence of acetic acid and sulfuric acid. The thus formed amide in the intermediates of formula (XVIII-a) can be transformed in an amine using (diacetoxyiodo)benzene or a functional derivative thereof in a suitable solvent such as, for example a mixture of water and acetonitrile. The amine derivative of formula (XVIII-b) can then be reacted with benzotriazol-1-yloxytris(dimethylamino) phosphonium hexafluoro-phosphate as described in Tetrahedron Letters No.14 (1975) p. 1219–1222 to obtain a compound, or with a functional derivative thereof such as, for instance, an isothiocyanate, in an appropriate solvent such as, for example, tetrahydrofuran.

Intermediates of formula (VIII) can be prepared as depicted in scheme 5.

Scheme 5

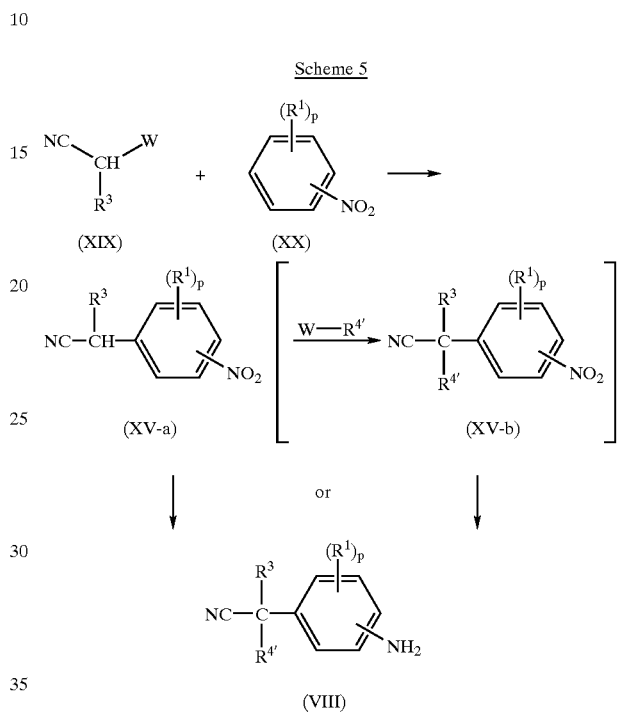

An intermediate of formula (XIX) and an intermediate of formula (XX) may be reacted in a suitable solvent such as, for example, dimethylsulfoxide, in the presence of a base such as, for example sodium hydroxide, to form an intermediate of formula (XV-a). The nitro moiety in the intermediates of formula (XV-a) may either be immediately reduced to an amino group using art-known reduction techniques such as, for example, reducing the nitro group with hydrogen in methanol and in the presnece of a catalyst such as Raney Nickel, or may first be reacted with an intermediate of formula $R^{4'}$-W wherein $R^{4'}$ is the same as $R^4$ but other than hydrogen and W is a suitable leaving group such as, for example, a halogen, e.g. iodo, in a suitable solvent such as, for example, N,N-dimethylformamide, and in the presence of a suitable base such as, for example, sodium hydride, before reducing the nitro moiety.

The compounds of formula (I) can also be converted into each other following art-known procedures of functional group transformation such as, for example, those mentioned in WO99/02505 and the ones exemplified in the experimental part hereinafter. In particular, compounds of formula (I) containing at least one —C(=O)—Z—$R^{14}$ moiety born by $R^2$, wherein Z is O or S and $R^{14}$ is other than hydrogen, can suitably be prepared by reacting the compound of formula (XXI) containing the corresponding moiety —C(=O)—Z—H with an appropriate reagent of formula (XXII) wherein $W^2$ is a suitable leaving group, as follows:

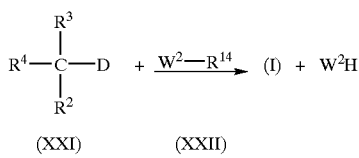

(XXI) (XXII)

For instance a first process of such preparation involves reacting the compound of formula (XXI) containing the corresponding moiety —C(=O)—Z—H with a halide, preferably a bromide having the formula Br—$R^{14}$, in a reaction-inert solvent such as defined above and in the presence of sodium hydrogenocarbonate. The said reaction is performed at a temperature below the boiling point of the solvent used and, for example, for a period of time between about 2 and 18 hours when dimethylformamide is used as the solvent. A second process of such preparation involves reacting the compound of formula (XXI) containing the corresponding moiety —C(=O)—Z—H with an alcohol having the formula $R^{14}$—OH, in a reaction-inert solvent such as defined above and in the presence of 1,1'-carbonylbis-1H-imidazole optionally admixed with 1,8-Diaza-7-bicyclo (5.4.0) undecene. When methylene chloride is used as the solvent, the reaction may be performed at room temperature for a period of time of several hours.

The present invention is also concerned with new compounds of formula:

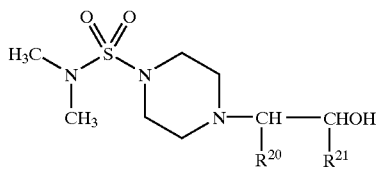

(XXIII)

wherein $R^{20}$ and $R^{21}$ are each independently selected from hydrogen or $C_{1-20}$ alkyl or $R^{20}$ and $R^{21}$ taken together with the carbon atom to which they are attached form a cycloalkyl radical. These new compounds are useful for preparing a compound of formula (I) when $Het^5$ represents a sulfonamido substituted piperazine. Such intermediate compounds of formula (XXIII) can be prepared by reacting N,N-dimethyl-1-piperazinesulfonamide with an alkylene oxide in a reaction-inert solvent such as methanol and/or methylene chloride. Suitable alkylene oxides for this purpose include for instance ethylene oxide, propylene oxide, 1–2 butylene oxide, cyclohexylene oxide and the like.

The present invention is also concerned with new compounds of formulae:

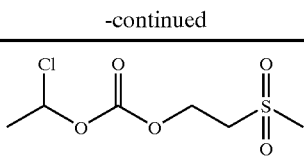

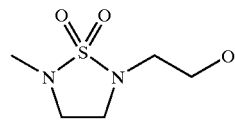

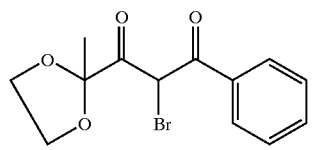

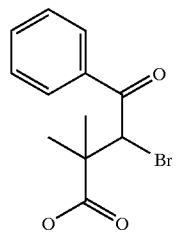

which are useful intermediates in the preparation of some of the compounds of formula (I).

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with 3-phenyl-2-(phenylsulfonyl)oxaziridine or with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g. counter-current distribution, liquid chromatography and the like.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

Some of the intermediates and starting materials as used in the reaction procedures mentioned hereinabove are known compounds and may be commercially available or may be prepared according to art-known procedures.

IL-5, also known as eosinophil differentiating factor (EDF) or eosinophil colony stimulating factor (Eo-CSF), is a major survival and differentiation factor for eosinophils and therefore thought to be a key player in eosinophil infiltration into tissues. There is ample evidence that eosinophil influx is an important pathogenic event in bronchial asthma and allergic diseases such as, cheilitis, irritable bowel disease, eczema, urticaria, vasculitis, vulvitis, winterfeet, atopic dermatitis, pollinosis, allergic rhinitis and allergic conjunctivitis; and other inflammatory diseases, such as eosinophilic syndrome, allergic angiitis, eosinophilic fasciitis, eosinophilic pneumonia, PIE syndrome, idiopathic eosinophilia, eosinophilic myalgia, Crohn's disease, ulcerative colitis and the like diseases.

The present compounds also inhibit the production of other chemokines such as monocyte chemotactic protein-1 and -3 (MCP-1 and MCP-3). MCP-1 is known to attract both T-cells, in which IL-5 production mainly occurs, and monocytes, which are known to act synergetically with eosinophils (Carr et al., 1994, Immunology, 91, 3652–3656). MCP-3 also plays a primary role in allergic inflammation as it is known to mobilize and activate basophil and eosinophil leukocytes (Baggiolini et al., 1994, Immunology Today, 15(3), 127–133).

The present compounds have no or little effect on the production of other chemokines such as IL-1, IL-2, Il-3, IL-4, IL-6, IL-10, γ-interferon (IFN-) and granulocyte-macrophage colony stimulating factor (GM-CSF) indicating that the present IL-5 inhibitors do not act as broad-spectrum immunosuppressives.

The selective chemokine inhibitory effect of the present compounds can be demonstrated by in vitro chemokine measurements in human blood. In vivo observations such as the inhibition of eosinophilia in mouse ear, the inhibition of blood eosinophilia in the Ascaris mouse model; the reduction of serum IL-5 protein production and splenic IL-5 mRNA expression induced by anti-CD3 antibody in mice and the inhibition of allergen- or Sephadex-induced pulmonary influx of eosinophils in guinea-pig are indicative for the usefulness of the present compounds in the treatment of eosinophil-dependent inflammatory diseases.

The present inhibitors of IL-5 production are particularly useful for administration via inhalation.

The intermediates of formula (XI-a) are interesting intermediates. Not only have they a particular usefulness as intermediates in the preparation of the compounds of formula (I), they also have valuable pharmacological activity.

In view of the above pharmacological properties, the compounds of formula (I) can be used as a medicine. In particular, the present compounds can be used in the manufacture of a medicament for treating eosinophil-dependent inflammatory diseases as mentioned hereinabove, more in particular bronchial asthma, atopic dertmatitis, allergic rhinitis and allergic conjunctivitis.

In view of the utility of the compounds of formula (I), there is provided a method of treating warm-blooded animals, including humans, suffering from eosinophil-dependent inflammatory diseases, in particular bronchial asthma, atopic dertmatitis, allergic rhinitis and allergic conjunctivitis. Said method comprises the systemic or topical administration of an effective amount of a Compound of formula (I), a N-oxide form, a pharmaceutically acceptable addition salt or a possible stereoisomeric form thereof, to warm-blooded animals, including humans.

The present invention also provides compositions for treating eosinophil-dependent inflammatory diseases comprising a therapeutically effective amount of a compound of formula (I) and a pharmaceutically acceptable carrier or diluent.

To prepare the pharmaceutical compositions of this invention, a therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as parenteral administration; or topical administration such as via inhalation, a nose spray or the like. Application of said compositions may be by aerosol, e.g. with a propellent such as nitrogen, carbon dioxide, a freon, or without a propellent such as a pump spray, drops, lotions, or a semisolid such as a thickened composition which can be applied by a swab. In particular, semisolid compositions such as salves, creams, gellies, ointments and the like will conveniently be used.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In order to enhance the solubility and/or the stability of the compounds of formula (I) in pharmaceutical compositions, it can be advantageous to employ α-, β- oρ γ-cyclodextrins or their derivatives. Also co-solvents such as alcohols may improve the solubility and/or the stability of the compounds of formula (I) in pharmaceutical compositions. In the preparation of aqueous compositions, addition salts of the subject compounds are obviously more suitable due to their increased water solubility.

Appropriate cyclodextrins are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyethyl, hydroxypropyl or hydroxybutyl; carboxy$C_{1-6}$alkyl, particularly carboxymethyl or carboxy-ethyl; $C_{1-6}$alkylcarbonyl, particularly acetyl; $C_{1-6}$alkyloxycarbonyl$C_{1-6}$alkyl or carboxy-$C_{1-6}$alkyloxy$C_{1-6}$alkyl, particularly carboxymethoxypropyl or carboxyethoxypropyl; $C_{1-6}$alkylcarbonyloxy$C_{1-6}$alkyl, particularly 2-acetyloxypropyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-γ-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

The average molar substitution (M.S.) is used as a measure of the average number of moles of alkoxy units per mole of anhydroglucose. The M.S. value can be determined by various analytical techniques, preferably, as measured by mass spectrometry, the M.S. ranges from 0.125 to 10.

The average substitution degree (D.S.) refers to the average number of substituted hydroxyls per anhydroglucose unit. The D.S. value can be determined by various analytical techniques, preferably, as measured by mass spectrometry, the D.S. ranges from 0.125 to 3.

Due to their high degree of selectivity as IL-5 inhibitors, the compounds of formula (I) as defined above, are also useful to mark or identify receptors. To this purpose, the compounds of the present invention need to be labelled, in particular by replacing, partially or completely, one or more atoms in the molecule by their radioactive isotopes. Examples of interesting labelled compounds are those compounds having at least one halo which is a radioactive isotope of iodine, bromine or fluorine; or those compounds having at least one $^{11}$C-atom or tritium atom.

One particular group consists of those compounds of formula (I) wherein $R^1$ is a radioactive halogen atom. In principle, any compound of formula (I) containing a halogen atom is prone for radiolabelling by replacing the halogen atom by a suitable isotope. Suitable halogen radioisotopes to this purpose are radioactive iodides, e.g. $^{122}$I, $^{123}$I, $^{125}$I, $^{131}$I; radioactive bromides, e.g. $^{75}$Br, $^{76}$Br, $^{77}$Br and $^{82}$Br, and radioactive fluorides, e.g. $^{18}$F. The introduction of a radioactive halogen atom can be performed by a suitable exchange reaction or by using any one of the procedures as described hereinabove to prepare halogen derivatives of formula (I).

Another interesting form of radiolabelling is by substituting a carbon atom by a $^{11}$C-atom or the substitution of a hydrogen atom by a tritium atom.

Hence, said radiolabelled compounds of formula (I) can be used in a process of specifically marking receptor sites in biological material. Said process comprises the steps of (a) radiolabelling a compound of formula (I), (b) administering this radiolabelled compound to biological material and subsequently (c) detecting the emissions from the radiolabelled compound.

The term biological material is meant to comprise every kind of material which has a biological origin. More in particular this term refers to tissue samples, plasma or body fluids but also to animals, specially warm-blooded animals, or parts of animals such as organs.

The radiolabelled compounds of formula (I) are also useful as agents for screening whether a test compound has the ability to occupy or bind to a particular receptor site. The degree to which a test compound will displace a compound of formula (I) from such a particular receptor site will show the test compound ability as either an agonist, an antagonist or a mixed agonist/antagonist of said receptor.

When used in in vivo assays, the radiolabelled compounds are administered in an appropriate composition to an animal and the location of said radiolabelled compounds is detected using imaging techniques, such as, for instance, Single Photon Emission Computerized Tomography (SPECT) or Positron Emission Tomography (PET) and the like. In this manner the distribution of the particular receptor sites throughout the body can be detected and organs containing said receptor sites can be visualized by the imaging techniques mentioned hereinabove. This process of imaging an organ by administering a radiolabelled compound of formula (I) and detecting the emissions from the radioactive compound also constitutes a part of the present invention.

In general, it is contemplated that a therapeutically effective daily amount would be from 0.01 mg/kg to 50 mg/kg body weight, in particular from 0.05 mg/kg to 10 mg/kg body weight. A method of treatment may also include administering the active ingredient on a regimen of between two or four intakes per day.

Experimental Part

In the examples hereinafter, "DMSO" stands for dimethylsulfoxide, "RT" stands for room temperature, "DMF" stand for N,N-dimethylformamide, "EtOAc" stands for ethylacetate, "DIPE" stands for diisopropylether and "THF" stands for tetrahydrofuran.

A. Preparation of the Intermediate Compounds

EXAMPLE A1 a) A mixture of 2-chloropropionitrile (0.2 mole) and 1,3-dichloro-5-nitrobenzene (0.2 mole) in DMSO (50 ml) was added dropwise at RT to a solution of NaOH (1 mole) in DMSO (150 ml) while the temperature was kept below 30° C. The mixture was stirred at RT for 1 hour, then poured out on ice and acidified with HCl. The precipitate was filtered off, washed with $H_2O$ and taken up in $CH_2Cl_2$. The organic solution was washed with $H_2O$, dried, filtered and the solvent was evaporated. The residue was purified by column chromatography over silica gel (eluent: $CH_2Cl_2$/cyclohexane 70/30). The pure fractions were collected and the solvent was evaporated, yielding 19.5 g (40%) of (±)-2,6-dichloro-α-methyl-4-nitrobenzeneacetonitrile (intermediate 1).

b) NaH 80% (0.0918 mole) was added portionwise at 0° C. under $N_2$ flow to a solution of intermediate (1) (0.0612 mole) in DMF (100 ml). The mixture was stirred at 0° C. under $N_2$ flow for 1 hour. $CH_3$I (0.0918 mole) was added dropwise at 0° C. The mixture was stirred at 50° C. for 12 hours, then poured out on ice and extracted with EtOAc. The organic layer was separated, washed with $H_2O$, dried, filtered and the solvent was evaporated, yielding 17.1 g of 2,6-dichloro-α,α-dimethyl-4-nitrobenzeneacetonitrile (intermediate 2).

c) A mixture of intermediate (2) (0.066 mole) in $CH_3OH$ (200 ml) was hydrogenated at RT under a 3 bar pressure for 1 hour with Raney Nickel (15 g) as a catalyst. After uptake of $H_2$, the catalyst was filtered through celite, washed with $CH_3OH$ and the filtrate was evaporated, yielding 17.1 g of 4-amino-2,6-dichloro-α,α-dimethylbenzeneacetonitrile (intermediate 3).

EXAMPLE A2 a) A solution of $NaNO_2$ (0.36 mole) in $H_2O$ (50 ml) was added to a solution of intermediate (3) (0.34 mole) in acetic acid (700 ml) and HCl (102 ml), stirred at 10° C. The reaction mixture was stirred for 80 minutes at 10° C. A powdered mixture of sodium acetate (1.02 mole) and diethyl (1,3-dioxo-1,3-propanediyl)biscarbamate (0.374 mole) was added and the reaction mixture was stirred for 40 minutes. The reaction mixture was poured out onto crushed ice. The precipitate was filtered off, washed with water, taken up into CH$_2$Cl$_2$, and the layers were separated. The organic layer was dried, filtered and the solvent evaporated, yielding 138.5 g (84%) of diethyl N,N'-[2-[[3,5-dichloro-4-(1-cyano-1-methylethyl)phenyl]hydrazono]-1,3-dioxo-1,3-propanediyl]dicarbamate (intermediate 4).

b) A solution of intermediate (4) (0.28 mole) and potassium acetate (0.28 mole) in acetic acid (1000 ml) was stirred and refluxed for 3 hours. The reaction mixture containing ethyl [[2-[3,5-dichloro-4-(1-cyano-1-methylethyl)phenyl]-2,3,4,5-tetrahydro-3,5-dioxo-1,2,4-triazin-6-yl]carbonyl]carbamate (intermediate 5) was used as such in the next step.

c) Intermediate (5) (crude reaction mixture) was treated with HCl 36% (0.84 mole). The reaction mixture was stirred and refluxed for 4 hours, then stirred at RT over the weekend. The reaction mixture was poured out onto crushed ice and this mixture was extracted with CH$_2$Cl$_2$. The separated organic layer was dried, filtered and the solvent evaporated, yielding 111.6 g of 2-[3,5-dichloro-4-(1-cyano-1-methylethyl)phenyl]-2,3,4,5-tetrahydro-3,5-dioxo-1,2,4-triazine-6-carboxylic acid (intermediate 6).

d) A suspension of intermediate (6) (0.28 mole) in mercaptoacetic acid (250 ml) was stirred for 4 hours at 100° C., then allowed to cool to RT and stirred overnight. The reaction mixture was poured out onto crushed ice and this mixture was extracted with CH$_2$Cl$_2$. The separated organic layer was dried, filtered and the solvent evaporated. Toluene was added and azeotroped on the rotary evaporator. The residue was purified by short column chromatography over silica gel (eluent: CH$_2$Cl$_2$/CH$_3$OH 98/2). The pure fractions were collected and the solvent was evaporated. The residue was stirred in DIPE, filtered off, washed with DIPE, then dried, yielding 36.8 g (41%) of 2,6-dichloro-4-(4,5-dihydro-3,5-dioxo-1,2,4-triazin-2(3H)-yl)-α,α-dimethylbenzeneacetonitrile. The filtrate was stirred in DIPE and the resulting precipitate was filtered off, washed with DIPE, and dried, yielding 2.5 g (3%) of 2,6-dichloro-4-(4,5-dihydro-3,5-dioxo-1,2,4-triazin-2(3H)-yl)-α,α-dimethylbenzeneacetonitrile (intermediate 7).

e) A solution of intermediate (7) (0.107 mole) and N,N-bis(1-methylethyl)ethanamine (0.315 mole) in pyridine (500 ml) was stirred and heated to 80° C. H$_2$S was allowed to bubble through this solution for 24 hours at 80° C. H$_2$S gas inlet was stopped and the reaction mixture was stirred over the weekend at RT. The solvent was evaporated. 500 ml of a 9:1 CH$_2$Cl$_2$/CH$_3$OH mixture was added, and the resulting mixture was then poured out into 2 N HCl (1000 ml) at 0° C. and stirred for 10 minutes. The precipitate was filtered off and dried, yielding 23.2 g (64%) of 2,6-dichloro-4-(4,5-dihydro-3,5-dioxo-1,2,4]-α,α-dimethylbenzeneethanethioamide (intermediate 8).

EXAMPLE A3

Under a nitogen atmosphere, a solution of intermediate (8) (0.0125 mole) and

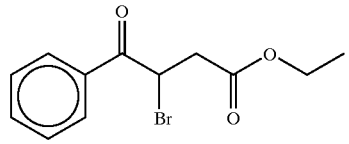

(0.0157 mole) in ethanol (60 ml) and DMF (30 ml; dried over molecular sieves) was stirred for 6.5 hours at 60° C., then overnight at RT. The solvent was evaporated. The residue was taken up into water (100 ml) and this mixture was extracted with CH$_2$Cl$_2$ (100 ml). The separated organic layer was dried (MgSO$_4$), filtered and the solvent evaporated, then co-evaporated with toluene. The residue (13 g) was purified by flash column chromatography over silica gel (eluent: CH$_2$Cl$_2$/CH$_3$OH 100/0, then 99/1, ending with 98/2). The desired fractions were collected and the solvent was evaporated. Toluene was added and azeotroped on the rotary evaporator. The residue (6.5 g) was crystallized from CH$_3$CN. The precipitate was filtered off, washed with CH$_3$CN and DIPE, then dried under vacuum at 50° C., yielding 3.17 g (46.5%) of ethyl-2-[1-[2,6-dichloro-4-(4,5-dihydro-3,5-dioxo-1,2,4-triazin-2(3H)-yl]phenyl]-1-methylethyl]-4-phenyl-5-thiazoleacetate (intermediate 9) having a melting point of 148° C.

EXAMPLE A4

A mixture of intermediate (9) (0.00183 mole) and NaOH 1N (0.0055 mole) in CH$_3$OH (25 ml) and THF (25 ml) was stirred overnight at RT. The reaction mixture was acidified with 1N HCl (8 ml) and the resulting product was taken up into EtOAc. The organic layer was washed with brine, dried, filtered and the solvent was evaporated. The residue was crystallized from CH$_3$CN. The precipitate was filtered off, washed with DIPE, and dried, yielding 0.8 g (79%) of 2-[1-[2,6-dichloro-4-(4,5-dihydro-3,5-dioxo-1,2,4-triazin-2(3H)yl)phenyl]-1-methylethyl]-4-phenyl-5-thiazoleacetic acid (intermediate 10).

EXAMPLE A5

First a solution of bromine (0.02 mole) in CH$_2$Cl$_2$ (20 ml) was added dropwise at 10° C. under a nitrogen flow to a mixture of a compound having the formula:

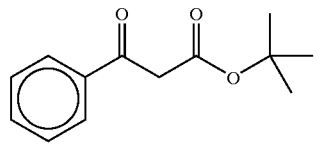

(0.0227 mole) in CH$_2$Cl$_2$ (50 ml). The mixture was stirred at 10° C. for 1 hour. H$_2$O and solid K$_2$CO$_3$ were added. The organic layer was separated, dried (MgSO$_4$), filtered and the solvent was evaporated. The reaction was carried out 4 times, using the same quantities and combining the residues, yielding 14 g (51%) of 1,1-dimethylethyl ∀-bromo-Ǝ-oxo-benzenepropanoate. A mixture of intermediate (8) (0.0119 mole), 1,1-dimethylethyl ∀-bromo-Ǝ-oxo-benzenepropanoate (0.0137 mole) and K$_2$CO$_3$ (0.0357 mole) in CH$_3$CN (55 ml) was stirred at room temperature for 3.5 hours. Ice and EtOAc were added. The mixture was acidified with HCl 3N. The organic layer was separated, dried (MgSO₄), filtered and the solvent was evaporated. The product was used without further purification, yielding 8 g of intermediate 11 having the formula

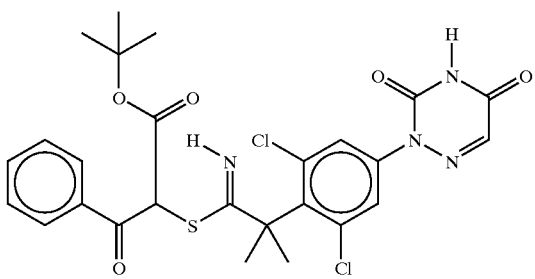

EXAMPLE A6

Intermediate (11) (0.0119 mole) and tert.-butanol (24 g) were stirred and refluxed for 2 hours. The mixture was brought to room temperature. The solvent was evaporated. The residue was taken up in CH₂Cl₂. The organic solution was washed with H₂O, dried (MgSO₄), filtered and the solvent was evaporated. The residue (7.8 g) was purified by column chromatography over silica gel (eluent: CH₂Cl₂/CH₃OH 99/1; 15–40 μm). Two fractions were collected and their solvents were evaporated, yielding 2.66 g (fraction 1) and 0.7 g (fraction 2) respectively. Fraction 2 was purified by column chromatography (eluent: CH₃OH/NH₄OAc 0.5% 80/20; column: HYPERSIL C18, 3 μm). The pure fractions were collected and the solvent was evaporated, yielding 0.45 g of intermediate 12 having a melting point of 130° C. and represented by the formula

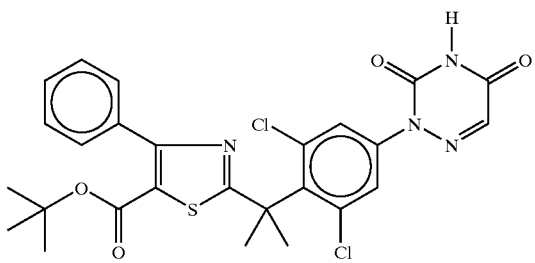

EXAMPLE A7

Intermediate 12 (0.00465 mole) was added portionwise at 0° C.–10° C. to trifluoroacetic acid (35 ml). The mixture was stirred at room temperature for 3 hours and poured out into H₂O. The precipitate was filtered off, washed with H₂O and taken up in CH₂Cl₂. The organic layer was separated, dried (MgSO₄), filtered and the solvent was evaporated. The residue (2.4 g) was purified by column chromatography over silica gel (eluent: CH₂Cl₂/CH₃OH/NH₄OH 97/3/0.2; 15–40 μm). The pure fractions were collected and the solvent was evaporated. The residue was crystallized from CH₃CN. The precipitate was filtered off and dried, yielding 1.16 g of intermediate 13 having a melting point of 232° C. and represented by the formula

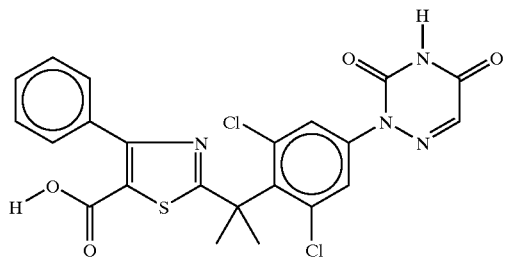

EXAMPLE A8

1,1'-carbonylbis-1H-imidazole (0.0159 mole) was added portionwise at RT under a nitrogen flow to a solution of intermediate (13) (0.00795 mole) in DMF (60 ml). The mixture was stirred at RT overnight. H₂S was bubbled through the mixture for 1 hour. The mixture was stirred at RT for 1 hour, poured out into a sarurated NaCl solution and extracted twice with CH₂Cl₂. The combined organic layer was dried (MgSO₄), filtered and the solvent was evaporated. The resulting intermediate 14, represented by the formula

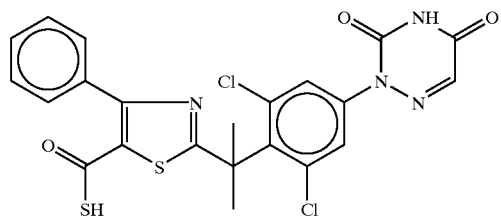

was used without further purification.

EXAMPLE A9

A mixture of intermediate (8) (0.0158 mole) and

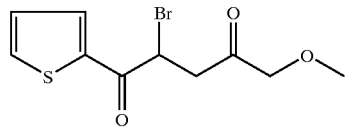

(0.0237 mole) in ethanol (60 ml) and DMF (40 ml) was stirred at 60° C. for 4 hours. The solvent was evaporated. EtOAc was added. The organic solution was washed 3 times with H₂O, dried (MgSO₄), filtered and the solvent was evaporated. The residue (11.2 g) was purified by column chromatography over silica gel (eluent: CH₂Cl₂/CH₃OH 98/2; 15–40 μm). The desired fractions were collected and the solvent was evaporated, yielding 4.2 g (47%) of a product, part of which (1.5 g) was crystallized from petroleum ether and DIPE. The precipitate was filtered off and dried, yielding 1.15 g of intermediate 15 having a melting point of 126° C. and represented by the formula

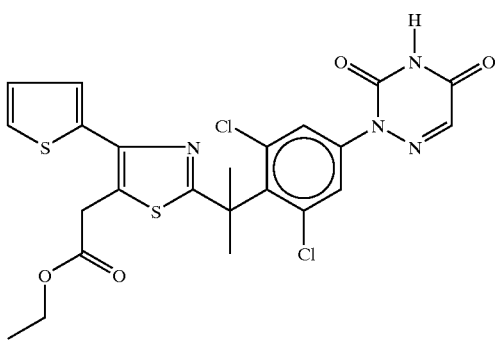

EXAMPLE A10

A mixture of intermediate (15) (0.0045 mole) and NaOH (0.0135 mole) in methanol (30 ml) and THF (30 ml) was stirred at room temperature for 12 hours, poured out on ice, acidified with HCl and extracted with EtOAc. The organic layer was separated, dried (MgSO$_4$), filtered and the solvent was evaporated. The residue (2.2 g) was purified by column chromatography over silica gel (eluent: CH$_2$Cl$_2$/CH$_3$OH/ NH$_4$OH 9515/0.1; 15–40 μm). The pure fractions were collected and the solvent was evaporated, yielding 1.5 g (64%) of a product, part of which (1 g) was crystallized from diethyl ether. The precipitate was filtered off and dried, yielding 0.5 g of intermediate 16 having a melting point of 192° C. and represented by the formula

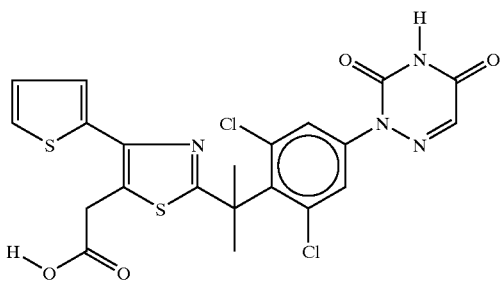

EXAMPLE A11 a) NaOCH$_3$ 30% (0.592 mole) was added to a solution of hydroxylamine hydrochloride (0.1085 mole) in CH$_3$OH (200 ml), stirred at RT. The mixture was stirred for 10 minutes. Intermediate (3) (0.0542 mole) was added portionwise and the resulting reaction mixture was stirred and refluxed overnight. The solvent was evaporated. The residue was partitioned between CH$_2$Cl$_2$ and water. The organic layer was separated, dried, filtered and the solvent was evaporated. The residue was stirred in DIPE, filtered off, washed with DIPE, and dried, yielding 3.7 g (26%) of 4-amino-2,6-dichloro-N'-hydroxy-α,α-dimethylbenzeneethanimidamide (intermediate 17).

b) A solution of intermediate (17) (0.0323 mole) and N,N-bis(methylethyl)ethanamine (0.0339 mole) in CH$_2$Cl$_2$ (190 ml) was stirred at 15° C. A solution of 2-methylbenzoyl chloride (0.0323 mole) in CH$_2$Cl$_2$ (10 ml) was added dropwise and the resulting reaction mixture was stirred for one hour. Water was added. The organic layer was separated, dried, filtered and the solvent was evaporated. Toluene was added and azeotroped on the rotary evaporator, yielding 13.0 g of [1-amino-2-(4-amino-2,6-dichlorophenyl)-2-methylpropylidenyl]amino 2-methylbenzoate (intermediate 18).

c) A solution of intermediate (18) (0.0323 mole) and paratoluenesulfonic acid (0.0323 mole) in DMSO (100 ml) was stirred for 30 minutes at 150° C. The reaction mixture was cooled. Water was added and this mixture was extracted with toluene. The separated organic layer was dried, filtered and the solvent evaporated. The residue was purified by short column chromatography over silica gel (eluent: CH$_2$Cl$_2$). The desired fractions were collected and the solvent was evaporated. The concentrate was co-evaporated with EtOAc, yielding 11.7 g of 3,5-dichloro-4-[1-[5-(2-methylphenyl)-1,2,4-oxadiazol-3-yl]-1-methylethyl]benzenamine (intermediate 19).

d) A solution of intermediate (19) (0.0302 mole) and concentrated HCl (0.0906 mole) in acetic acid (100 ml) was stirred at 0° C. A solution of NaNO$_2$ (0.032 mole) in water (10 ml) was added dropwise at 0° C. The reaction mixture was stirred for 1 hour at 0° C. A powdered mixture of sodium acetate (0.0906 mole) and diethyl(1,3-dioxo-1,3-propanediyl)biscarbamate (0.0332 mole) was added portionwise. The mixture was allowed to warm to RT and stirred for 1 hour. Water was added and this mixture was extracted with CH$_2$Cl$_2$. The separated organic layer was dried, filtered and the solvent evaporated, yielding diethyl N,N'-[2-[[3,5-dichloro-4-[1-[5-(2-methylphenyl)-1,2,4-oxadiazol-3-yl]-1-methylethyl]phenyl]hydrazono]-1,3-dioxo-1,3-propanediyl] dicarbamate (intermediate 20).

e) A solution of intermediate (20) (0.0302 mole) and sodium acetate (0.0302 mole) in acetic acid (200 ml) was stirred and refluxed for 3 hours. The reaction mixture was poured out into water and this mixture was extracted with CH$_2$Cl$_2$. The separated organic layer was dried, filtered and the solvent evaporated. Toluene was added and azeotroped on the rotary evaporator, yielding ethyl [[2-[3,5-dichloro-4-[1-[5-(2-methylphenyl)-1,2,4-oxadiazol-3-yl]-1-methylethyl]phenyl]-2,3,4,5-tetrahydro-3,5-dioxo-1,2,4-triazin-6-yl]carbonyl]carbamate (intermediate 21).

f) A mixture of intermediate (21) (0.0302 mole) in HCl 36% (10 ml) and acetic acid (200 ml) was stirred and refluxed overnight. The reaction mixture was poured out onto crushed ice and this mixture was extracted with CH$_2$Cl$_2$. The separated organic layer was dried, filtered and the solvent evaporated, yielding 16.3 g of 2-[3,5-dichloro-4-[1-[5-[2-methylphenyl)-1,2,4-oxadiazol-3-yl]-1-methylethyl]phenyl]-2,3,4,5-tetrahydro-3,5-dioxo-1,2,4-triazine-6-carboxylic acid (intermediate 22).

EXAMPLE A12

A mixture of intermediate (22) (0.0133 mole) in mercaptoacetic acid (7 ml) was stirred at 175° C. for 2 hours. The mixture was cooled, poured out into ice water, basified with K$_2$CO$_3$ and extracted with EtOAc. The organic layer was separated, washed with H$_2$O, dried, filtered and the solvent was evaporated. The residue was purified by column chromatography over silica gel (eluent: CH$_2$Cl$_2$/CH$_3$OH 99/1). The pure fractions were collected and the solvent was evaporated, yielding 2.2 g (36%) of intermediate 23 represented by the formula

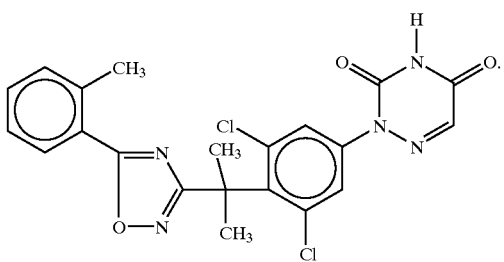

EXAMPLE A13

A mixture of intermediate (23) (0.0011 mole), 1-bromo-2,5-pyrrolinedione (0.0011 mole) and dibenzoyl peroxide (catalytic quantity) in $CCl_4$ (30 ml) was stirred and refluxed for 3 hours. The mixture was allowed to cool to RT. The mixture was filtered over a diatomaceous earth commercially available under the tradename Dicalite and the filtrate contained 2-[4-[1-[5-[2-(bromomethyl)phenyl]-1,2,4-oxadiazol-3-yl]-1-methylethyl]-3,5-dichlorophenyl]-1,2,4-triazine-3,5(2H,4H)-dione (intermediate 24).

EXAMPLE A14

A solution of intermediate (24) (0.017 mole) and KCN (0.034 mole) in ethanol (100 ml) and $H_2O$ (30 ml) was stirred for 8 hours at 60° C. The solvent was evaporated under reduced pressure. The residue was taken up into $CH_2Cl_2$, then washed with water, dried ($MgSO_4$), filtered and the solvent was evaporated, yielding 8.2 g of intermediate 25 represented by the formula

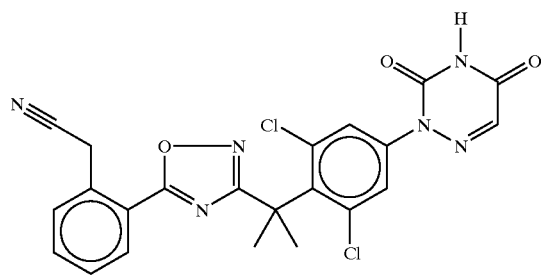

EXAMPLE A15

A solution of intermediate (25) (0.017 mole) in HOAc (50 ml), $H_2SO_4$ (50 ml) and $H_2O$ (50 ml) was stirred and refluxed for 2 hours. The reaction mixture was poured out into iced water and the resulting precipitate was filtered off, washed, then dissolved in $CH_2Cl_2$. The organic solution was dried, filtered and the solvent was evaporated. The residue was purified over silica gel on a glass filter (eluent: $CH_2Cl_2$/$CH_3OH$ 95/5). The desired fractions were collected and the solvent was evaporated. The residue was purified by high performance liquid chromatography over RP BDS Hyperprep C18 (100 Å, 8 μm; gradient elution with (0.5% $NH_4OAc$ in water/$CH_3CN$ 90/10)/$CH_3OH$/$CH_3CN$). The pure fractions were collected and the solvent was evaporated. The residue was stirred in hexane, filtered off and dried under vacuum at 60° C., yielding 0.084 g of intermediate 26 represented by the formula

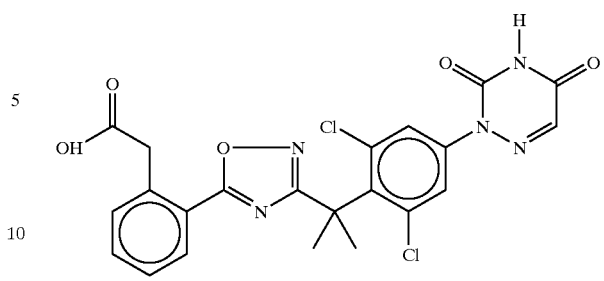

EXAMPLE A16

A solution of intermediate (26) (0.0014 mole) in $SOCl_2$ (15 ml) was stirred and refluxed for 1 hour. $SOCl_2$ was evaporated under reduced pressure. Toluene was added and azeotroped on the rotary evaporator, yielding 100% of intermediate 27 represented by the formula

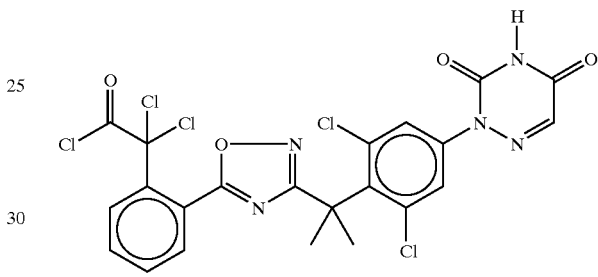

B. Preparation of the Final Compounds

EXAMPLE B1

A mixture of 3-bromodihydro-2(3H)-furanone (0.0081 mole) in DMF (16 ml) was added dropwise at room temperature to a mixture of intermediate (10)(0.00773 mole) and $NaHCO_3$ (0.0081 mole) in DMF (30 ml). The mixture was stirred at 70° C. for 5 hours and brought to room temperature. $H_2O$ and a saturated NaCl solution were added. The mixture was extracted with EtOAc. The organic layer was separated, dried ($MgSO_4$), filtered and the solvent was evaporated. The residue (5 g) was purified by column chromatography over silica gel (eluent: $CH_2Cl_2$/$CH_3OH$ 98/2; 15–40 μm). The pure fractions were collected and the solvent was evaporated. The residue was taken up in DIPE. The precipitate was filtered off and dried, yielding 1.24 g of compound 1 having a melting point of 72° C. and represented by the formula

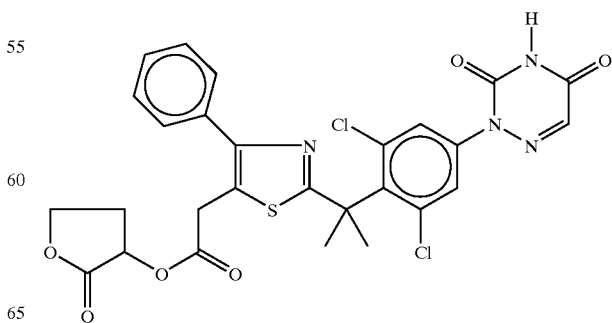

EXAMPLE B2

A solution of 1-bromopentadecane (0.0051 mole) in DMF (18 ml) was added dropwise at room temperature to a mixture of intermediate (10) (0.00483 mole) and NaHCO$_3$ (0.0051 mole) in DMF (10 ml). The mixture was stirred at 70° C. for 5 hours and at 45° C. overnight, then brought to room temperature. H$_2$O and NaCl were added. The mixture was extracted with EtOAc. The organic layer was separated, washed with a saturated NaCl solution, dried (MgSO$_4$), filtered and the solvent was evaporated. The residue (3.8 g) was purified by column chromatography over silica gel (eluent: CH$_2$Cl$_2$/CH$_3$OH 98/2; 15–40 μm). The pure fractions were collected and the solvent was evaporated, yielding 0.49 g of compound 2 having a melting point of 80° C. and represented by the formula (12 ml) was added dropwise. The mixture was brought to RT and stirred at RT for 30 minutes and then poured out into water and a saturated NaCl solution. A small amount of HCl 3N was added. The precipitate was filtered off and taken up in CH$_2$Cl$_2$. The organic layer was separated, dried (MgSO$_4$), filtered and the solvent was evaporated. The residue (5.1 g) was purified by column chromatography over silica gel (eluent: CH$_2$Cl$_2$/CH$_3$OH 98.5/1.5; 15–40 μm). The pure fractions were collected and the solvent was evaporated. The residue was crystallized from CH$_3$CN, diethyl ether and DIPE. The precipitate was filtered off and dried. The residue was recrystallized from CH$_3$CN, diethyl ether and DIPE. The precipitate was filtered off and dried, yielding 0.85 g of compound 4 having a melting point of 212° C. and represented by the formula

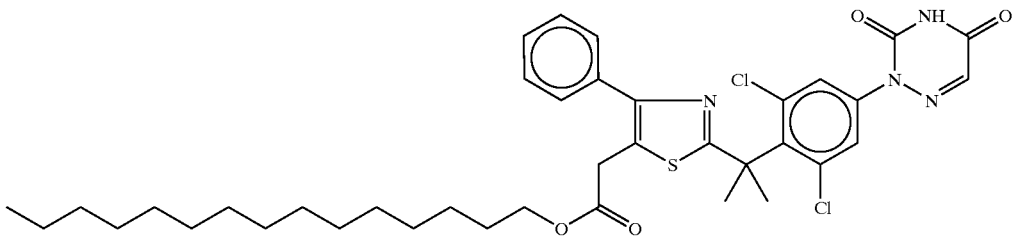

EXAMPLE B3

A solution of 3-bromodihydro-2(3H)-furanone (0.0073 mole) in DMF (12 ml) was added dropwise at RT to a mixture of intermediate (13) (0.00695 mole) and NaHCO$_3$ (0.0073 mole) in DMF (22 ml). The mixture was stirred at 70° C. for 2.5 hours, brought to RT and poured out into H$_2$O. The precipitate was filtered off and taken up in CH$_2$Cl$_2$. The organic layer was separated, washed with H$_2$O, dried (MgSO$_4$), filtered and the solvent was evaporated. The residue (5.4 g) was purified by column chromatography over silica gel (eluent: CH$_2$Cl$_2$/CH$_3$OH 98/2; 15–40 μm). The desired fractions were collected and the solvent was evaporated. The residue was crystallized from CH$_3$CN, diethyl ether and DIPE. The precipitate was filtered off and dried. Yielding: 1.3 g. This fraction was recrystallized from CH$_3$CN, 2-propanone and diethyl ether. The precipitate was filtered off and dried, yielding 0.89 g of compound 3 having a melting point of 208° C. and represented by the formula

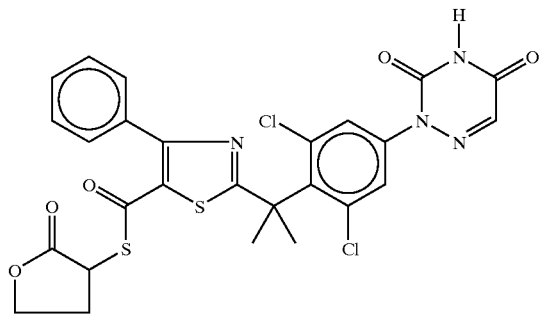

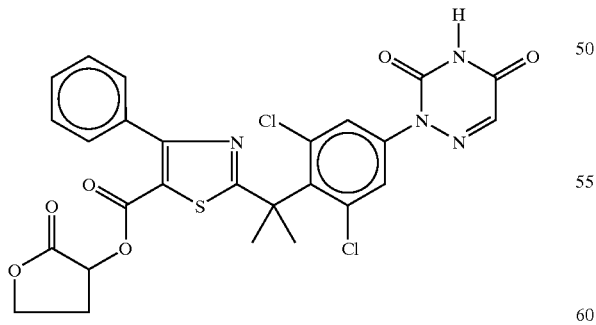

EXAMPLE B4

NaHCO$_3$ (0.00835 mole) was added dropwise at 5° C. under a nitrogen flow to a mixture of intermediate (14) (0.00795 mole) in DMF (22 ml). Then a solution of 3-bromodihydro-2(3H)-furanone (0.00835 mole) in DMF

EXAMPLE B5

A mixture of 3-bromodihydro-2(3H)-furanone (0.00172 mole) in DMF (5 ml) was added dropwise at RT to a mixture of intermediate (16) (0.00172 mole) and NaHCO$_3$ (0.00172 mole) in DMF (5 ml). The mixture was stirred at 70° C. for 5 hours, poured out into water and a saturated NaCl solution and extracted with EtOAc. The organic layer was separated, washed several times with water, dried (MgSO$_4$), filtered and the solvent was evaporated. The residue (1.2 g) was purified by column chromatography over silica gel (eluent: CH$_2$Cl$_2$/CH$_3$OH 98/2; 15–40 μm). The desired fractions were collected and the solvent was evaporated. The residue was purified again by column chromatography over silica gel (eluent: CH$_2$Cl$_2$/2-propanol 97/3; 15–40 μm). The desired fractions were collected and the solvent was evaporated, yielding 0.13 g of compound 5 having a melting point of 110° C. and represented by the formula

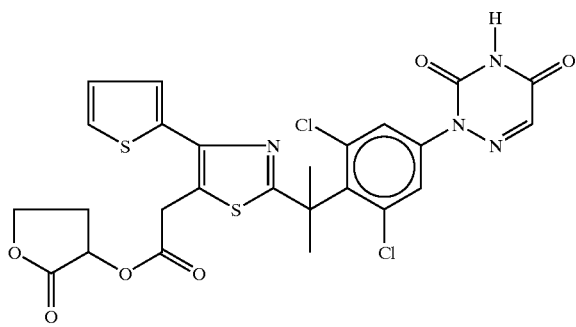

EXAMPLE B6

A solution of intermediate (27) (0.001 mole) in ethanol (15 ml) and dichloromethane (15 ml) was stirred and refluxed for one hour. The solvent was evaporated under reduced pressure. The residue was dissolved in $CH_2Cl_2$, washed with water, dried ($MgSO_4$), filtered and the solvent was evaporated. The residue was purified by means of high performance liquid chromatography over Hyperprep C18 (eluent: ((0.5% $NH_4OAc$ in $H_2O$)/$CH_3CN$ 90/10)/$CH_3CN$ (0 min) 80/20, (44 min) 20/80, (57–61 min) 0/100). The desired fractions were collected and the solvent was evaporated. The residue was stirred in hexane, filtered off, washed and dried under vacuum at 60° C., yielding 0.059 g of compound 6 having a melting point of 157° C. and represented by the formula

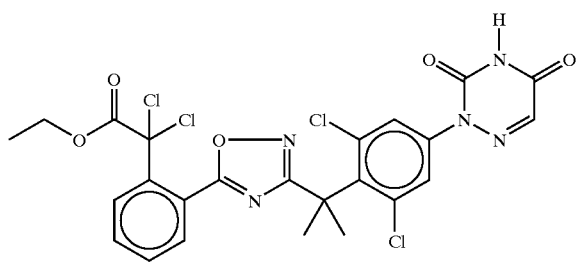

EXAMPLE B7

A mixture of intermediate (10) (0.00387 mole) and 1,1'-carbonylbis-1H-imidazole (0.0058 mole) in dichloromethane (40 ml) was stirred at RT for 90 minutes, then cyclohexylmethanol (0.0058 mole) was added. The mixture was stirred at RT overnight, diluted with $CH_2Cl_2$ and washed twice with an aqueous solution of NaCl. The organic layer was separated, dried ($MgSO_4$), filtered and the solvent was evaporated. The residue was purified by column chromatography over silica gel (eluent: $CH_2Cl_2$/EtOAc 50/50). The pure fractions were collected and the solvent was evaporated. The residue was crystallized from EtOAc. The precipitate was filtered off, washed with DIPE and dried at 50° C. overnight, yielding 1.43 g of compound 7 with a molecular weight of 613.5, a melting point of 180° C. and represented by the formula

IA

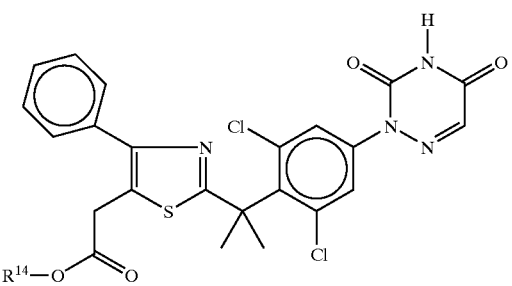

wherein $R^{14}$ is cyclohexylmethyl.

EXAMPLES B8 TO B53

The following table 1 lists compounds of formula (IA) which were prepared according to the procedure of example B7, while replacing cyclohexylmethanol by the relevant alcohol having the formula $R^{14}OH$. For the synthesis of compounds 8, 15–18, 21–23, 27, 32–34, 40–42 and 44, the amount of dichloromethane was increased up to 50 ml, and for compound 53 up to 60 ml. For the synthesis of compound 51, dichloromethane was replaced by 45 ml DMF. This table also indicates the melting point (when available) M.P. (expressed in ° C.) and the yield Y of obtention (expressed as a percentage) of the said compounds.

TABLE 1

| COMPOUND NO. | $R^{14}$ | M.P. (° C.) | Y (%) |
|---|---|---|---|
| 8 | ![phthalimido-CH2-CH2-] | | |
| 9 | Isopentyl | 148 | |
| 10 | 2-phenyl-ethyl | 130 | 38 |
| 11 | 3-phenyl-n-propyl | 114 | 41 |
| 12 | 2-(N,N'-diisopropylamino)-ethyl | 136 | |
| 13 | 2-cyano-ethyl | 179 | 62 |
| 14 | ![benzimidazol-2-yl-CH2-] | | 75 |

TABLE 1-continued

| COMPOUND NO. | R[14] | M.P. (° C.) | Y (%) |
|---|---|---|---|
| 15 | 3-cyclohexyl-n-propyl | 130 | |
| 16 | 4-phenyl-n-butyl | 128 | |
| 17 | Cyclopentylmethyl | | |
| 18 | 3-cyclopropyl-n-propyl | | |
| 19 | 1-(2-oxopyrrolidin-1-yl)ethyl group (N-CH₂-CH₂- attached to pyrrolidinone) | | 50 |
| 20 | 2-morpholinoethyl (morpholine-N-CH₂-CH₂-) | | |
| 21 | 5-phenyl-n-pentyl | 155 | |
| 22 | Cyclobutylmethyl | 150 | |
| 23 | 2-cyclohexylethyl | 150 | |
| 24 | benzyloxyethyl (PhCH₂-O-CH₂-) | | 56 |
| 25 | Cyclopentylmethyl | 160 | |
| 26 | 2-isopentenyl | 175 | |
| 27 | 1-Cyanoethyl | | |
| 28 | phenoxyethyl (PhO-CH₂-) | | |
| 29 | 4-Cyclohexyl-n-butyl | | |
| 30 | (2,3-dihydro-1,4-benzodioxin-2-yl)methyl | | 33 |
| 31 | 2,2,2-trifluoroethyl | | 67 |
| 32 | Phenylmethyl | | |
| 33 | Phenyl | | |
| 34 | 2-methoxyethyl | | |
| 35 | 3-ol-n-propyl | | |
| 36 | Acetamido | 246 | 29 |
| 37 | N,N'-diethylacetamido | 162 | 60 |
| 38 | Dimethylaminoethyl | | |
| 39 | Styrylmethyl | | |
| 40 | Cyclohexyl | 183 | 17 |
| 41 | Toluylacetyloxy | 151 | 71 |
| 42 | H₃C-O-C(=O)-C(CH₃)₂-CH₂- | 140 | 37 |
| 43 | N-methylpiperidinyl | | 28 |
| 44 | 4-methyl-γ-butyrolactonyl (4-methyl-tetrahydrofuran-2-one) | 160 | |

TABLE 1-continued

| COMPOUND NO. | R¹⁴ | M.P. (° C.) | Y (%) |
|---|---|---|---|
| 45 | (H₃C)₂N—SO₂—N(piperazine)N—CH₂—CH₂— | | 22 |
| 46 | (H₅C₂O)₂—P(=O)—CH₂— | 156 | 49 |
| 47 | H₂N—SO₂—N(4-methylpiperidine) | 191 | 37 |
| 48 | 2,2-diethoxyethyl | 156 | |
| 49 | 3,4,4-trimethyl-γ-butyrolactone | | 19 |
| 50 | Benzylaminoethyl | | |
| 51 | 3-methyl-5-methyl-γ-butyrolactone | | 40 |
| 52 | (H₃C)₂N—SO₂—N(piperazine)N—CH₂—CH₂— | | 22 |
| 53 | (CH₃)₃—C—O—C(=O)—N(4-methylpiperidine) | | 43 |

EXAMPLE B54

A mixture of 2-bromomethyl-1,4-benzodioxan (0.0044 mole) in DMF (2 ml was added to a mixture of intermediate (13)(0.0044 mole) and NaHCO₃ 0.0044 mole) in DMF (8 ml). The mixture was stirred at 70° C. for 6 hours, then 0.0022 mole of intermediate (13) was added. The mixture was stirred again at 70° C. overnight, then poured out into water, acidified with HCl (3N), extracted with EtOAc and washed with water. The organic layer was separated, dried, filtered and the solvent was evaporated. The residue (3.9 g) was purified by column chromatography over silica gel (eluent: CH₂Cl₂/CH₃OH 99/1; 15–40 μm). The pure fractions were collected and the solvent was evaporated. The residue (1.2 g) was crystallized from CH₃CN/DIPE. The precipitate was filtered off and dried, yielding 0.57 g of compound 54 having a molecular weight of 651.5, identified in table 2 below (wherein M.P. and Y have the same meanings as in table 1) and represented by the formula

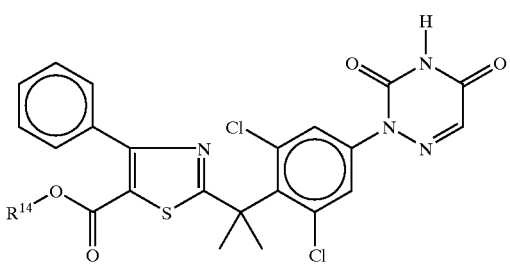

IB wherein R¹⁴ is

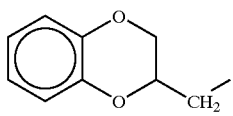

EXAMPLE B55

A mixture of bromo-1-phenyl-2-ethane (0.0065 mole), intermediate (13)(0.0050 mole) and $NaHCO_3$ (0.0050 mole) in DMF (10 ml) was stirred at 70° C. for 12 hours, then poured out on ice, acidified with HCl (3N) until pH 5, is extracted with EtOAc and washed several times with water. The organic layer was separated, dried ($MgSO_4$), filtered and the solvent was evaporated. The residue (3.2 g) was purified by column chromatography over silica gel (eluent: $CH_2Cl_2/CH_3OH$ 99/1; 70–200 μm). The pure fractions were collected and the solvent was evaporated. The residue (0.6 g) was crystallized from diethylether/DIPE. The precipitate was filtered off and dried, yielding 0.42 g of compound 55 of formula (IB), having a molecular weight of 607.5 and identified in table 2 below.

EXAMPLE B56

A mixture of phenylbromomethane (0.0065 mole), intermediate (13) (0.0050 mole) and $NaHCO_3$ (0.0050 mole) in DMF (10 ml) was stirred at 70° C. for 12 hours, then cooled and poured out on ice. The precipitate was filtered, washed with water and the solvent evaporated. The residue was taken up in HCl (diluted), then water. The organic layer was separated, dried ($MgSO_4$), filtered and the solvent was evaporated. The residue (3.0 g) was purified by column chromatography over silica gel (eluent: $CH_2Cl_2/CH_3OH$ 99.5/0.5; 70–200 μm). The pure fractions were collected and the solvent was evaporated. The residue (0.9 g) was crystallized from diethylether/DIPE. The precipitate was filtered off and dried, yielding 0.51 g of compound 56 of formula (IB), having a molecular weight of 593.5 and identified in table 2 below.

EXAMPLE B57

A mixture of tert-butyl bromoacetate (0.0060 mole), intermediate (13)(0.0050 mole) and $NaHCO_3$ (0.0050 mole) in DMF (10 ml) was stirred at 70° C. for 12 hours, then cooled and poured out into ice water. The precipitate was filtered, washed with $H_2O$, centrifugated off and taken up in EtOAc. The organic layer was separated, washed with water, dried ($MgSO_4$), filtered and the solvent was evaporated. The residue (3.0 g) was purified by column chromatography over silica gel (eluent: $CH_2Cl_2$; 70–200 μm). Two fractions were collected and their solvents were evaporated. The first fraction (0.9 g) was crystallized from DIPE. The precipitate was filtered off and dried, yielding 0.53 g of compound 57 of formula (IB), having a molecular weight of 617.5 and identified in table 2 below.

EXAMPLE B58

A mixture of cyclopropylbromomethane (0.0040 mole) in DMF (10 ml) was added dropwise at RT to a mixture of intermediate (13)(0.0040 mole) and $NaHCO_3$ (0.0040 mole) in DMF (10 ml). The mixture was stirred at 70° C. for 5 hours, poured out on ice, neutralized slowly with HCl (3N) and extracted with EtOAc. The organic layer was separated, washed several times, dried ($MgSO_4$), filtered and the solvent was evaporated. The residue (2.8 g) was purified by column chromatography over silica gel (eluent: $CH_2Cl_2$/EtOAc 92/8; 15–40 μm; $CH_3CN/NH_4Ac$ 1% 60/40 10 μm). The pure fractions were collected and the solvent was evaporated, yielding 0.34 g of compound 58 of formula (IB), having a molecular weight of 557.5 and identified in table 2 below.

EXAMPLE B59

A mixture of chloro-1 dimethylamino-2 ethane (0.0044 mole) and $NaHCO_3$ (0.0087 mole) in DMF (10 ml) was stirred at RT for 30 minutes. Intermediate (13)(0.0050 mole) was added portionwise. The mixture was stirred at 70° C. overnight, cooled, poured out onto water and neutralized with HCl 3N. The precipitate was filtered, washed with water and taken up in $CH_2Cl_2$. The organic layer was separated, dried ($MgSO_4$), filtered and the solvent was evaporated. The residue (2.4 g) was purified by column chromatography over silica gel (eluent: $CH_2Cl_2/CH_3OH$ 94/6; 15–40 μm). The pure fractions were collected and the solvent was evaporated, yielding 0.58 g of compound 59 of formula (IB), having a molecular weight of 574.5 and identified in table 2 below.

EXAMPLE B60

A mixture of 1-chloroethyl ethylcarbonate (0.0065 mole), intermediate (13)(0.0050 mole), $NaHCO_3$ (0.0050 mole) and potassium iodide (0.0050 mole) in DMF (10 ml) was stirred at 70° C. for 12 hours, then cooled and poured out into ice water. The precipitate was filtered off, washed with a diluted solution of HCl, washed with water, centrifugated and taken up in EtOAc. The organic layer was separated, dried ($MgSO_4$), filtered and the solvent was evaporated. The residue (3.3 g) was purified by column chromatography over silica gel (eluent: $CH_2Cl_2$; 70–200 μm). The desired fractions were collected and the solvent was evaporated. The residue (0.7 g) was crystallized from diethylether/DIPE. The precipitate was filtered off and dried, yielding 0.34 g of compound 60 of formula (IB), having a molecular weight of 619.5 and identified in table 2 below.

EXAMPLE B61

A mixture of ethyl bromoacetate (0.0040 mole) in DMF (2 ml) was stirred at RT. A solution of intermediate (13) (0.0040 mole) and $NaHCO_3$ (0.0040 mole) in DMF (8 ml) was added. The mixture was stirred at 70° C. for 2 hours, cooled, poured out into ice water and acidified with HCl 3N. The precipitate was filtered off, washed with water and taken up in EtOAc. The organic layer was separated, washed with water, dried ($MgSO_4$), filtered and the solvent was evaporated. The residue (2.2 g) was purified by column chromatography over silica gel (eluent: $CH_2Cl_2/CH_3OH$ 99/1; 15–40 μm). The pure fractions were collected and the solvent was evaporated. The residue (1.2 g) was crystallized from diethylether. The precipitate was filtered off and dried, yielding 0.98 g compound 61 of formula (IB), having a molecular weight of 589.5 and identified in table 2 below.

EXAMPLE B62

A mixture of bromo-1-phenyl-3-propane (0.0065 mole), intermediate (13)(0.0050 mole), $NaHCO_3$ (0.0050 mole) in DMF (10 ml) was stirred at 70° C. for 12 hours, then poured out into ice water and extracted with EtOAc. The organic layer was separated, washed with a diluted solution of HCl, washed with water, dried ($MgSO_4$), filtered and the solvent was evaporated. The residue (3.5 g) was purified by column chromatography over silica gel (eluent: $CH_2Cl_2$; 70–200 μm). The pure fractions were collected and the solvent was evaporated. The residue (1.2 g) was crystallized from diethylether/DIPE. The precipitate was filtered off and dried, yielding 0.85 g of compound 62 of formula (IB), having a molecular weight of 621.5 and identified in table 2 below.

EXAMPLE B63

A mixture of 2-(chloromethyl)benzimidazole (0.0044 mole) in DMF (5 ml) was added dropwise at RT to a mixture of intermediate (13)(0.0044 mole) and NaHCO$_3$ (0.0044 mole) in DMF (5 ml). The mixture was stirred at 70° C. for 15 hours, cooled and poured out on ice. The precipitate was filtered off, washed with water several times, centrifugated off and taken up in EtOAc. The organic layer was separated, washed with water, dried (MgSO$_4$), filtered and the solvent was evaporated. The residue (3.5 g) was purified by column chromatography over silica gel (eluent: CH$_2$Cl$_2$/CH$_3$OH 98/2; 15–40 µm). The pure fractions were collected and the solvent was evaporated. The residue (0.9 g) was crystallized from diethylether. The precipitate was filtered off and dried, yielding 0.4 g of compound 63 of formula (IB), having a molecular weight of 633.5 and identified in table 2 below.

EXAMPLE B64

A mixture of cyclobutyl bromomethane (0.0040 mole) in DMF (2 ml) was added at RT to a mixture of intermediate (13)(0.0040 mole) and NaHCO$_3$ (0.0040 mole) in DMF (8 ml). The mixture was stirred at 70° C. overnight, then cooled, poured out into ice water and extracted with EtOAc. The organic layer was separated, washed with water, dried (MgSO$_4$), filtered and the solvent was evaporated. The residue (2.1 g) was purified by column chromatography over silica gel (eluent: CH$_2$Cl$_2$/CH$_3$OH 99.25/0.75; 15–40 µm, CH$_3$CN/NH$_4$Ac 75/25; 10 µm). The pure fractions were collected and the solvent was evaporated. The residue (0.9 g) was crystallized from diethylether. The precipitate was filtered off and dried, yielding 0.44 g of compound 64 of formula (IB), having a molecular weight of 571.5 and identified in table 2 below.

EXAMPLE B65

A mixture of bromo-3-propanol-1 (0.0050 mole), intermediate (13)(0.0046 mole), NaHCO$_3$ (0.0046 mole) in DMF (10 ml) was stirred at 70° C. for 6 hours, then cooled and poured out into ice water. The precipitate was filtered, washed with a diluted solution of HCl and died. The residue was taken up in CH$_2$Cl$_2$. The organic layer was separated, washed with water, dried (MgSO$_4$), filtered and the solvent was evaporated. The residue (2.6 g) was purified by column chromatography over silica gel (eluent: CH$_2$Cl$_2$/CH$_3$OH 97.5/2.5; 15–40 µm). The desired fractions were collected and the solvent was evaporated. The residue (0.8 g) was crystallized from DIPE. The precipitate was filtered off and dried, yielding 0.55 g of compound 65 of formula (IB), having a molecular weight of 561.5 and identified in table 2 below.

EXAMPLE B66

A mixture of bromo-1 methyl-3 butene-2 (0.0040 mole) in DMF (2 ml) was added at RT to a solution of intermediate (13) (0.0040 mole) and NaHCO$_3$ (0.0040 mole) in DMF (8 ml). The mixture was stirred at 70° C. for 20 hours, cooled, poured out into ice water, acidified with HCl 3N and then extracted with EtOAc. The organic layer was separated, dried (MgSO$_4$), filtered and the solvent was evaporated. The residue (2.0 g) was purified by column chromatography over silica gel (eluent: CH$_2$Cl$_2$/CH$_3$OH 99.5/0.5; 70–200 µm). The desired fractions were collected and the solvent was evaporated. The residue (0.5 g) was purified again by column chromatography over silica gel (eluent: CH$_3$CN/ 0.5%NH$_4$Oac 70/30; 10 µm). The pure fractions were collected and the solvent was evaporated, yielding 0.25 g of compound 66 of formula (IB), having a molecular weight of 571.5 and identified in table 2 below.

EXAMPLE B67

A mixture of iodomethyl trimethylacetate (0.0119 mole), intermediate (13)(0.0040 mole) and NaHCO$_3$ (0.0050 mole) in DMF (20 ml) was stirred at 70° C. for 12 hours, then poured out on ice and acidified with HCl 3N. The precipitate was filtered off and dried. The residue was taken up in CH$_2$Cl$_2$. The organic layer was separated, dried (MgSO$_4$), filtered and the solvent was evaporated. The residue (2.3 g) was purified by column chromatography over silica gel (eluent: CH$_2$Cl$_2$/CH$_3$OH 98.5/1.5; 15–40 µm to CH$_3$COONH$_2$/CH$_3$CN 25/75; 10 µm). The pure fractions were collected and the solvent was evaporated, yielding 0.25 g of compound 67 of formula (IB), having a molecular weight of 617.5 and identified in table 2 below.

EXAMPLE B68

A mixture of N,N-diethyl bromoacetamide (0.0065 mole), intermediate (13) (0.0050 mole) and NaHCO$_3$ (0.0050 mole) in DMF (10 ml) was stirred at 70° C. for 12 hours, cooled and poured out on ice. The precipitate was filtered, washed with water, centrifugated off and taken up in EtOAc. The organic layer was separated, washed with a diluted solution of HCl, washed with water, dried (MgSO$_4$), filtered and the solvent was evaporated. The residue (3.1 g) was purified by column chromatography over silica gel (eluent: CH$_2$Cl$_2$/ CH$_3$OH 98.5/1.5; 15–40 µm). The pure fractions were collected and the solvent was evaporated. The residue (1.4 g) was crystallized from CH$_3$CN and diethylether. The precipitate was filtered off and dried, yielding 0.7 g of compound 68 of formula (IB), having a molecular weight of 616.5 and identified in table 2 below.

EXAMPLE B69

A mixture of 4-chloro-1,3-dioxolan-2-one (0.0031 mole), intermediate (13) (0.0024 mole), NaHCO$_3$ (0.0024 mole) and potassium iodide (0.0024 mole) in DMF (6 ml) was stirred at 70° C. for 5 hours, poured out into ice water and acidified with HCl 3N. The precipitate was filtered off, washed with water and taken up in CH$_2$Cl$_2$. The organic layer was separated, dried (MgSO$_4$), filtered and the solvent was evaporated. The residue (1.8 g) was purified by column chromatography over silica gel (eluent: CH$_2$Cl$_2$/CH$_3$OH 98/2; 15–40 µm). The pure fractions were collected and the solvent was evaporated, yielding 0.65 g of compound 69 of formula (IB), having a molecular weight of 589.5 and identified in table 2 below.

EXAMPLE B70

A mixture of 4-bromomethyl-5-methyl-1,3-dioxol-2-one (0.0034 mole), intermediate (13)(0.0026 mole), NaHCO$_3$ (0.0026 mole) in DMF (6 ml) was stirred at 70° C. for 12 hours, then poured out into ice water and acidified with HCl 3N. The precipitate was filtered, washed with water and taken up in CH$_2$Cl$_2$. The organic layer was separated, dried (MgSO$_4$), filtered and the solvent was evaporated. The residue (1.8 g) was purified by column chromatography over silica gel (eluent: CH$_2$Cl$_2$/CH$_3$OH 98/2; 15–40 µm) then over Kromasil (eluent: CH$_3$CN/CH$_3$OH 80/20; 3.5 µm). The pure fractions were collected and the solvent was evaporated, yielding 0.28 g of compound 70 of formula (IB), having a molecular weight of 615.5 and identified in table 2 below.

EXAMPLE B71

A mixture of 4-bromomethyl-5-methyl-1,3-dioxol-2-one (0.0046 mole), intermediate (14)(0.0035 mole), NaHCO$_3$ (0.0035 mole) in DMF (10 ml) was stirred at 70° C. for 5 hours, poured out into ice water and acidified with HCl 3N.

The precipitate was filtered, washed with water and taken up in CH₂Cl₂. The organic layer was separated, dried (MgSO₄), filtered and the solvent was evaporated. The residue (2.5 g) was purified by column chromatography over silica gel (eluent: CH₂Cl₂/CH₃OH 99/1; 15–40 μm) then over Kromasil (eluent: CH₃CN/AcNH₄ 65/35; 10 μm). The pure fractions were collected and the solvent was evaporated, yielding 0.36 g (33%) of compound 71, having a molecular weight of 631.5 and a melting point of 97° C. and represented by the formula:

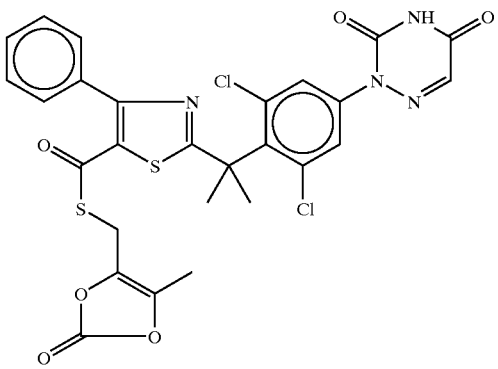

EXAMPLE B72

4-bromomethyl-5-methyl-1,3-dioxol-2-one (0.0081 mole) was dissolved in DMF (20 ml). This solution was added dropwise to intermediate (10)(0.0077 mole) and NaHCO₃ (0.0081 mole) in DMF (30 ml) under nitrogen atmosphere. The reaction mixture was stirred at 50° C. for 3 hours, poured out into water (+NaCl) and extracted three times with EtOAc. The organic layer was separated, dried (MgSO₄), filtered and the solvent was evaporated. The residue was purified by high performance liquid chromatography over silica gel (eluent: CH₂Cl₂/CH₃CN). The desired fractions were collected and the solvent was evaporated, yielding 0.86 g of an oily fraction which was stirred in hexane/EtOAc (1:1) until a white precipitate was formed. This precipitate was filtered off, washed with DIPE and dried overnight, yielding 0.58 g of compound 72, having a molecular weight of 629.5 and a melting point of 149° C. and represented by the formula:

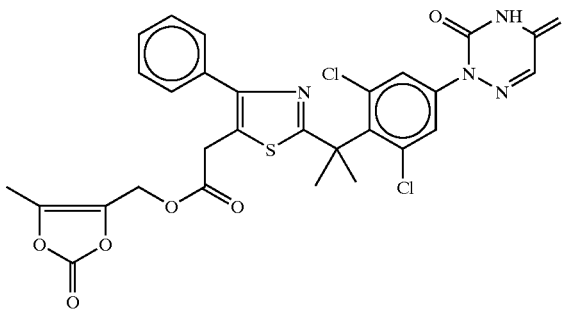

TABLE 2

| COMPOUND NO. | R¹⁴ | M.P. (° C.) | Y (%) |
|---|---|---|---|
| 54 | (1,4-benzodioxan-2-ylmethyl) | 182 | 53 |
| 55 | Phenyl-2 ethyl | 146 | 20 |
| 56 | Phenylmethyl | 167 | 30 |
| 57 | Tert-butyl acetyl | 165 | 17 |
| 58 | Cyclopropylmethyl | 100 | 13 |
| 59 | Dimethylaminoethyl | 204 | 22 |
| 60 | C₂H₅O—C(=O)—O—CH(CH₃)— | 163 | 11 |
| 61 | Ethylacetyl | 198 | |
| 62 | Phenyl-3 propyl | 165 | 27 |
| 63 | (1H-benzimidazol-2-ylmethyl) | 172 | 14 |
| 64 | Cyclobutylmethyl | 80 | 33 |
| 65 | Hydroxy-3 propyl | 85 | 31 |
| 66 | Methyl-3-butene-2-yl | 90 | 11 |
| 67 | Trimethylacetyl | 80 | 10 |
| 68 | Diethylacetamido | 157 | |
| 69 | (4-methyl-1,3-dioxolan-2-one-5-ylmethyl) | 90 | 36 |
| 70 | (4,5-dimethyl-1,3-dioxol-2-one-yl methyl) | 102 | 14 |

EXAMPLE B73

A mixture of intermediate (10) (0.00387 mole) and 1,1'-carbonylbis-1H-imidazole (0.0058 mole) in dichloromethane (40 ml) was stirred at RT for 90 minutes, then 3-aminodihydro-2(3H)furanone (0.0058 mole) was added. The mixture was stirred at RT overnight, diluted with CH₂Cl₂ and washed twice with an aqueous solution of NaCl. The organic layer was separated, dried (MgSO₄), filtered and the solvent was evaporated. The residue was filtered over silica gel (eluent: CH₂Cl₂/EtOAc 50/50). The product fractions were collected and the solvent was evaporated. The residue was crystallized from EtOAc. The residue was stirred in DIPE, filtered off, washed and dried at 50° C. under vacuum for two days, yielding 1.43 g (62%) of compound 73 having a molecular weight of 600.5 and represented by the formula

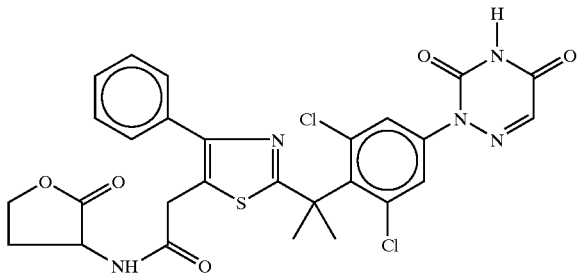

EXAMPLES B74 AND B75

A mixture of intermediate (10) (0.0156 mole) and 1,1'-carbonylbis-1H-imidazole (0.0232 mole) in DMF (160 ml) was stirred at RT for 3 hours, and then treated with an excess of hydrogen sulfide for 20 minutes at RT, then with nitrogen overnight. Half of this reaction mixture, containing 0.0078 mole of compound 74 represented by the formula

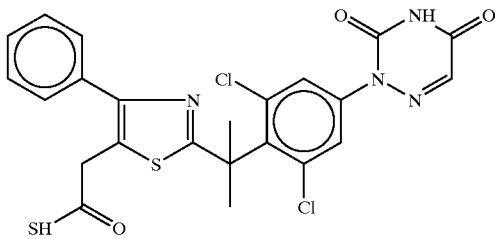

in 80 ml DMF, was treated with a solution of 4-bromomethyl-5-methyl-1,3-dioxol-2-one (0.013 mole) in DMF (20 ml). The reaction mixture was stirred for one hour, then poured out into water and extracted twice with EtOAc. The organic layer was separated, dried (MgSO$_4$), filtered and the solvent was evaporated. The residue was purified over silica gel on a glass filter (eluent: CH$_2$Cl$_2$/EtOAc 92.5/7.5). The pure fractions were collected and the solvent was evaporated. The residue was stirred in DIPE, filtered off, washed and dried under vacuum for one hour, yielding 2.68 g (54%) of compound 75 represented by the formula

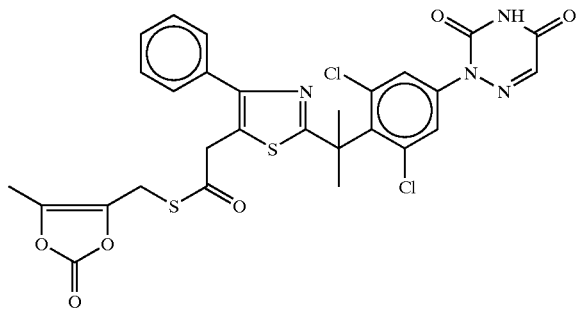

EXAMPLE B76

1,1'-carbonylbis-1H-imidazole (0.0017 mole) was added to a mixture of intermediate (13) (0.0014 mole) in DMF (6 ml). The mixture was stirred at 40° C. for one hour. A solution of N,N-dimethylethanolaminesulfonamide (0.0028 mole) and 1,8-diazabicyclo (5.4.0) undecene-7 (0.0014 mole) in DMF (3 ml) was added. The mixture was stirred at 40° C. for 3 hours, then brought to RT, poured out into water, acidified with HCl 3N, filtered and washed with water. The precipitate was filtered off and dried. The residue was taken up in diethyl ether. The organic layer was separated, dried (MgSO$_4$), filtered and the solvent was evaporated. The residue was crystallized from diethyl ether/CH$_3$CN/DIPE, yielding 0.77 g (65%) of compound 76 having a molecular weight of 653.5 g, a melting point of 150° C. and being represented by the formula

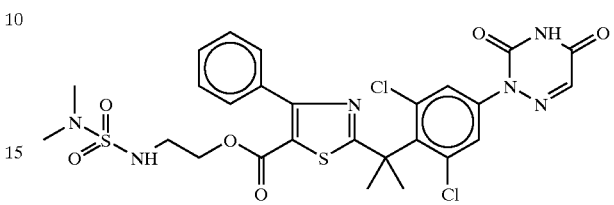

EXAMPLE B77

1,1'-carbonylbis-1H-imidazole (0.0013 mole) was added at RT to a mixture of intermediate (13) (0.0010 mole) in DMF (4 ml). The mixture was stirred at 40° C. for 45 minutes. A mixture of N-(2-hydroxyethyl)-1-piperidinesulfonamide (0.0019 mole) and 1,8-diazabicyclo (5.4.0) undecene-7 (0.0010 mole) in DMF (2 ml) was added fastly. The mixture was stirred at 40° C. for 90 minutes, then brought to RT, poured out into water and acidified with HCl 3N. The precipitate was filtered off and dried. The residue was taken up in CH$_2$Cl$_2$, then filtered and dried again and then purified by column chromatography over silica gel (eluent: CH$_2$Cl$_2$/CH$_3$OH 98.5/1.5; 15–40 μm). The pure fractions were collected and the solvent was evaporated. The residue (0.34 g) was taken up in DIPE. The precipitate was filtered off and dried, yielding 0.18 g (57%) of compound 77 having a molecular weight of 693.5 g, a melting point of 126° C. and being represented by the formula

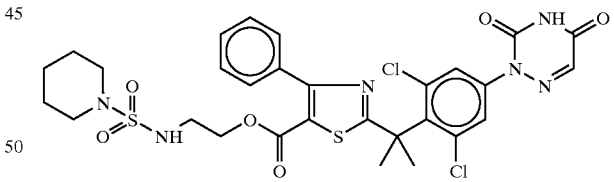

EXAMPLE B78

1,1'-carbonylbis-1H-imidazole (0.0030 mole) was added at RT to a mixture of intermediate (13) (0.0024 mole) in DMF (12 ml). The mixture was stirred at 40° C. for one hour. A solution of 2,2,2-trifluoroethanol (0.0048 mole) and 1,8-diazabicyclo (5.4.0) undecene-7 (0.0024 mole) in DMF (5 ml) was added. The mixture was stirred at 40° C. for 2 hours, poured out on ice/HCl 3N, filtered and washed with water.

The precipitate was taken up in CH₂Cl₂. The organic layer was separated, dried (MgSO₄), filtered and the solvent was evaporated. The residue was crystallized from diethyl ether, then filtered off and dried, yielding 0.51 g (31%) of compound 78 having a molecular weight of 583.5 g, a melting point of 180° C. and being represented by the formula

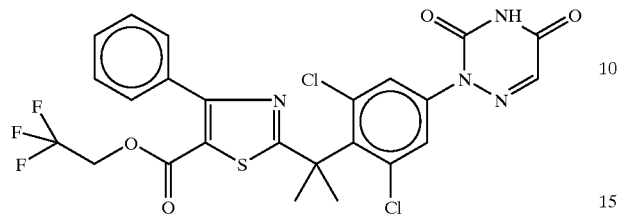

EXAMPLE B79

1,1'-carbonylbis-1H-imidazole (0.0050 mole) was added to a mixture of intermediate (13) (0.0040 mole) in DMF (15 ml). The mixture was stirred at 40° C. for one hour. A solution of N-(2-hydroxyethyl)-N'-piperazinesulfonamide (0.0104 mole) and 1,8-diazabicyclo (5.4.0) undecene-7 (0.0040 mole) in DMF (10 ml) was added. The mixture was stirred at 40° C. for 2 hours, then brought to RT, poured out on ice water and acidified with HCl 3N. The precipitate was filtered, washed with water and taken up in CH₂Cl₂/CH₃OH. The organic layer was separated, dried (MgSO₄), filtered and the solvent was evaporated. The residue (2.7 g) was purified by column chromatography over silica gel (eluent: CH₂Cl₂/CH₃OH 96/4; 15–40 μm). The pure fractions were collected and the solvent was evaporated, yielding 0.3 g (10%) of compound 79 having a molecular weight of 694.5 g, a melting point of 133° C. and being represented by the formula

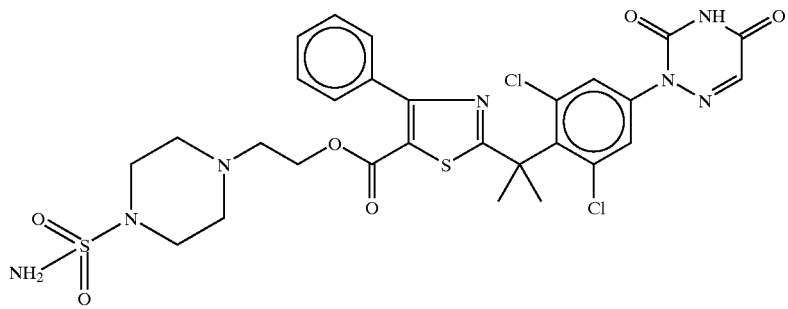

EXAMPLE B80

A mixture of intermediate (8) (0.0097 mole) and -bromo- -oxo-benzenepentanoic acid ethyl ester (0.0126 mole) in ethanol (150 ml) was stirred and refluxed overnight. The solvent was evaporated and the residue was taken up in methylene chloride. The organic layer was separated, washed with a 10% solution of K₂CO₃ then with water, dried (MgSO₄), filtered and the solvent was evaporated. The residue (5.7 g) was purified by column chromatography over silica gel (eluent: CH₂Cl₂/CH₃OH 98.5/1.5; 15–40 μm). The pure fractions were collected and the solvent was evaporated, yielding 3.2 g (59%) of compound 80 having a molecular weight of 559.5 g, a melting point of 155° C. and being represented by the formula

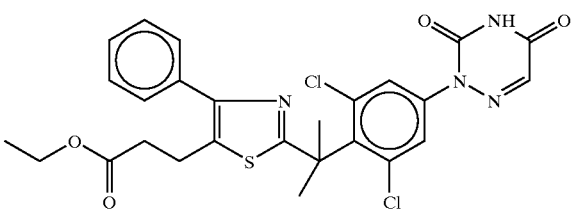

EXAMPLE 81

A mixture of compound 80 (0.0032 mole) and sodium hydroxide (0.0096 mole) in methanol (20 ml) and THF (20 ml) was stirred at RT for 12 hours, poured out on ice, acidified with HCl 1N and extracted with EtOAc. The organic layer was separated, dried (MgSO₄), filtered and the solvent was evaporated, yielding 1.7 g of a compound of the formula

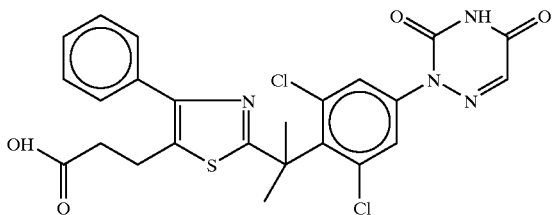

which, after crystallization from diethyl ether, shows a melting point of 186° C. A mixture of -bromo- - butyrolactone (0.0021 mole) in DMF (5 ml) was added dropwise at RT to a mixture of the compound obtained in the preceding step (0.0021 mole) and NaHCO₃ (0.0021 mole) in DMF (5 ml). The mixture was stirred at 70° C. for five hours, poured out on ice, neutralized slowly with HCl (3N) and extracted with EtOAc and washed with water. The organic layer was separated, washed several times with water, dried (MgSO₄), filtered and the solvent was evaporated. The residue (1.1 g) was purified by column chromatography over silica gel (eluent: CH₂Cl₂/CH₃OH 99/1; 1540 μm). The pure fractions were collected and the solvent was evaporated. The residue (1.2 g) was crystallized from diethylether and CH₃CN. The precipitate was filtered off and dried, yielding 0.25 g (19%) of compound 81 having a molecular weight of 615.5 g, a melting point of 190° C. and being represented by the formula

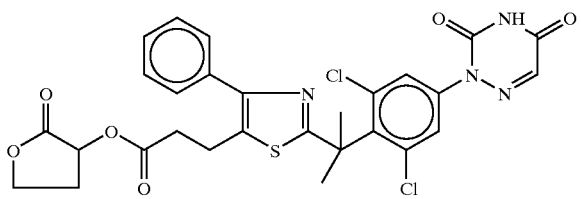

EXAMPLE B82

Intermediate (13) (0.0050 mole) was added to DMF (20 ml) under a nitrogen flow. 1,1'-carbonylbis-1H-imidazole (0.0062 mole) was added and the mixture was stirred at 40° C. for one hour. Then 2-(2-methoxyethoxy) ethanol (0.0099 mole) and 1,8-diazabicyclo (5.4.0) undecene-7 (0.005 mole) were added and the resulting mixture was stirred at 40° C. for 12 hours, cooled and then diluted with diethyl ether. The organic layer was separated, washed with HCl 3N then with water, dried (MgSO$_4$), filtered and the solvent was evaporated. The residue (2.5 g) was purified by column chromatography over silica gel (eluent: CH$_2$Cl$_2$/CH$_3$OH 98.5/1.5; 15–40 μm). The pure fractions were collected and the solvent was evaporated. The residue (1.5 g) was crystallized from DIPE. The precipitate was filtered off and dried, yielding 1.03 g (34%) of compound 82 having a molecular weight of 605.5 g, a melting point of 151° C. and being represented by the formula

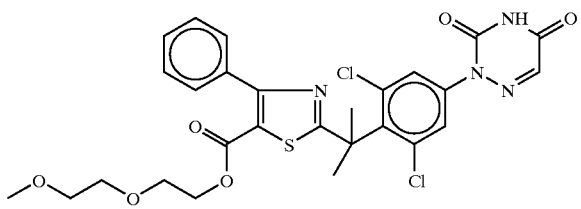

EXAMPLE B83

A mixture of N,N-dimethyl-1-piperazinesulfonamide (0.0423 mole) in methanol (100 ml) and methylene chloride (30 ml) was treated with an excess of gaseous ethylene oxide at 5° C. for 90 minutes. The reaction mixture was stirred at RT for 3 hours. The solvent was evaporated, then co-evaporated with toluene. The residue was stirred overnight in 7N NH$_3$/CH$_3$OH and the solvent was evaporated, then co-evaporated with toluene. The residue (10.3 g) was purified over silica gel on a glass filter (eluent: CH$_2$Cl$_2$/CH$_3$OH 92.5/7.5). The desired fractions were collected and the solvent was evaporated, then co-evaporated with toluene, yielding 6.9 g (69%) of a compound 83 represented by the formula

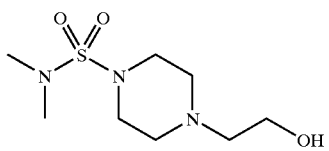

which after crystallization from diethyl ether, shows a melting point of 186° C.

EXAMPLE B84

Intermediate (13) (0.0036 mole) was added to DMF (15 ml) under a nitrogen flow. 1,1'-carbonylbis-1H-imidazole (0.0045 mole) was added and the mixture was stirred at 40° C. for one hour. Then a solution of compound 83 (0.0072 mole) and 1,8-diazabicyclo (5.4.0) undecene-7 (0.0036 mol) was added over two minutes and the resulting mixture was stirred at 40° C. for 5 hours, brought to RT, poured out into water, filtered and taken up in CH$_2$Cl$_2$. The organic layer was separated, washed with water, dried (MgSO$_4$), filtered and the solvent was evaporated. The residue (2.5 g) was purified by column chromatography over silica gel (eluent: CH$_2$Cl$_2$/CH$_3$OH 97/3; 15–40 μm). The pure fractions were collected and the solvent was evaporated. The residue (1.3 g) was crystallized from CH$_3$CN and diethyl ether. The precipitate was filtered off and dried, yielding 1.0 g of compound 84 having a molecular weight of 722.7 g, a melting point of 220° C. and being represented by the formula

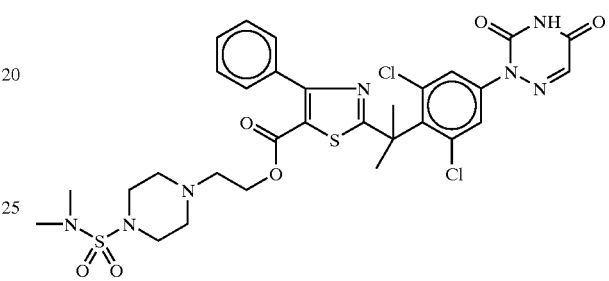

EXAMPLE B85

A mixture of bromoacetonitrile (0.0040 mole) in DMF (2 ml) was added at RT to a solution of intermediate (13) (0.0040 mole) and NaHCO$_3$ (0.0040 mole) in DMF (8 ml). The mixture was stirred at 70° C. overnight, cooled, poured out into ice water, acidified with HCl (3N) and then extracted with EtOAc. The organic layer was separated, washed with water, dried (MgSO$_4$), filtered and the solvent was evaporated. The residue (1.9 g) was purified by column chromatography over silica gel (eluent: CH$_2$Cl$_2$/CH$_3$OH 99.25/0.75; 15–40 μm). The fractions were collected and, after evaporation of their solvent, purified again by column chromatography over silica gel (eluent: CH$_2$Cl$_2$/CH$_3$OH 99.25/0.75; 15–40 μm). The pure fractions were collected and the solvent evaporated, yielding 0.26 g (12%) of compound 85 having a molecular weight of 542.5 g and being represented by the formula

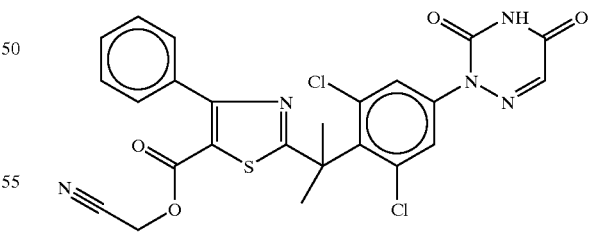

EXAMPLE B86

Intermediate (13) (0.0034 mole) was added under a nitrogen flow to DMF (25 ml). 1,1'-carbonylbis-1H-imidazole (0.0043 mole) was added and the mixture was stirred at 40° C. for one hour. (Hydroxymethyl) phosphonate diethyl ester (0.0068 mole) and 1,8-diazabicyclo (5.4.0) undecene-7 (0.0034 mole) were added and the mixture was stirred at 40° C. for 5 hours, then brought to room temperature, poured out into water and acidified with HCL 3N. The precipitate was filtered off and taken up in methylene chloride. The organic layer was separated, washed with water, dried (MgSO$_4$), filtered and the solvent was evaporated. The residue (3.0 g) was purified by column chromatography over silica gel (eluent: CH$_2$Cl$_2$/CH$_3$OH 98/2; 15–40 μm). The fractions were collected and the solvent was evaporated. The residue (1.4 g) was taken up in DIPE. The precipitate was filtered off and dried, yielding 1.3 g of compound 86 having a molecular weight of 653.5 g, a melting point of 88° C. and being represented by the formula

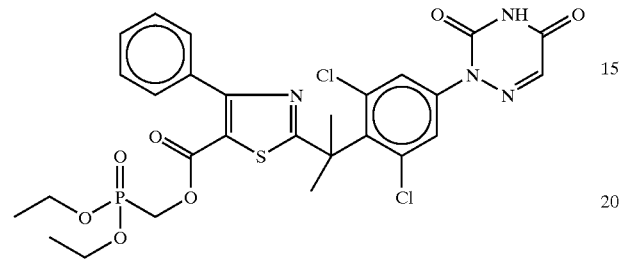

EXAMPLE B87

A mixture of bromo-3 propylene-1 (0.0040 mole) in DMF (2 ml) was added at RT to a solution of intermediate (13) (0.0040 mole) and NaHCO$_3$ (0.0040 mole) in DMF (8 ml). The mixture was stirred at 70° C. overnight, poured out into ice water and extracted with EtOAc. The organic layer was separated, washed with water, dried (MgSO$_4$), filtered and the solvent was evaporated. The residue (2.2 g) was purified by column chromatography over silica gel (eluent: CH$_2$Cl$_2$/CH$_3$OH 99.5/0.5; 35–70 μm). The fractions were collected and the solvent evaporated. The residue (0.8 g) was crystallized from acetonitrile. The precipitate was filtered off and dried, yielding 0.31 g (15%) of compound 87 having a molecular weight of 543.5 g, a melting point of 172° C. and being represented by the formula

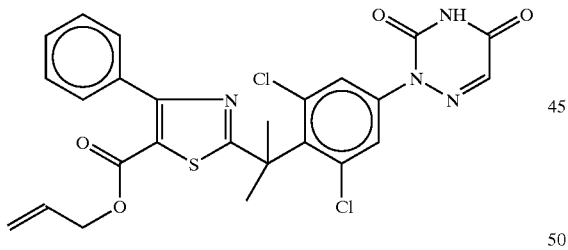

EXAMPLE B88

A mixture of bromoacetylene (0.0040 mole) in DMF (2 ml) was added at RT to a solution of intermediate (13) (0.0040 mol) and NaHCO$_3$ (0.0040 mole) in DMF (8 ml). The mixture was stirred at 70° C. overnight, poured out into ice water and extracted with EtOAc. The organic layer was separated, washed with water, dried (MgSO$_4$), filtered and the solvent was evaporated. The residue (2.5 g) was purified by column chromatography over silica gel (eluent: CH$_2$Cl$_2$; column: 70–200 μm). The desired fractions were collected and the solvent evaporated. The residue was purified again by column chromatography over silica gel (eluent: CH$_3$CN/NH$_4$Oac 68/32; column Kromasil C18 10 μm). The pure fractions were collected and the solvent was evaporated. The residue (0.6 g) was crystallized from diethyl ether. The precipitate was filtered off and dried, yielding 0.41 g of compound 88 having a molecular weight of 541.5 g, a melting point of 180° C. and being represented by the formula

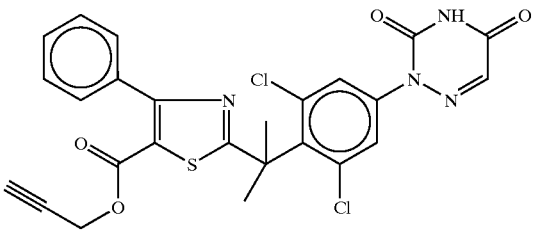

EXAMPLE B89

1,1'-carbonylbis-1H-imidazole (0.0048 mole) was added to a mixture of intermediate (13) (0.00397 mole) in methylene chloride (36 ml). The resulting mixture was stirred at room temperature for 24 hours, then HCl 1N was added. The organic layer was separated, dried (MgSO$_4$), filtered and the solvent was evaporated. The residue (1.95 g) was purified by flash column chromatography over silica gel (eluent: CH$_2$Cl$_2$/CH$_3$OH 99/1; 35–70 μm). The pure fractions were collected and the solvent was evaporated, yielding 1.16 g (53%) of a compound 89 having a molecular weight of 546.4 g, a melting point of 112° C. and being represented by the formula

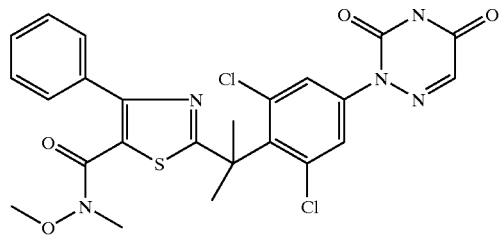

EXAMPLE B90

A mixture of intermediate (10) (0.02 mole) and 1,1'-carbonylbis-1H-imidazole (0.03 mole) in methylene chloride (250 ml) was stirred for 2 hours at room temperature. 2,2-dimethyl-1,3-Dioxane-4,6-dione (0.03 mole) was added and the resulting reaction mixture was stirred overnight at room temperature. A solid was formed. Water and a saturated aqueous NaCl solution were added. The product was extracted with CH$_2$Cl$_2$/THF (70/30). The organic layer was separated, dried, filtered and the solvent evaporated, yielding 12.9 g of a product, part of which (2.2 g) was purified over silica gel on a glass filter (eluent: CH$_2$Cl$_2$/CH$_3$OH 95/5). The fractions were collected and the solvent was evaporated. The residue was stirred in DIPE, filtered off and dried, yielding 0.7 g of a compound 90 having a molecular weight of 679.5 g and being represented by the formula

EXAMPLE B91

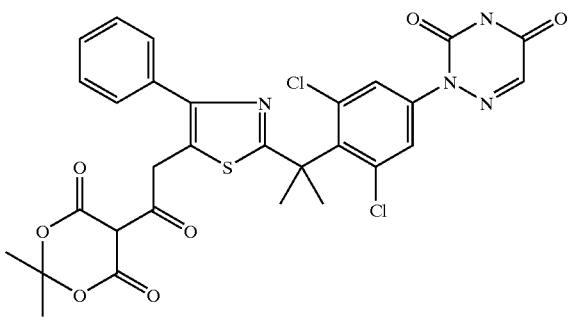

A mixture of compound 90 (0.013 mole) in acetic acid (50 ml) and water (100 ml) was stirred and refluxed (oil bath) for 2 hours with evolution of $CO_2$. The mixture was poured out into iced water, then extracted with $CH_2Cl_2$. The separated organic layer was dried, filtered and the solvent evaporated. The residue was purified over silica gel on a glass filter (eluent: $CH_2Cl_2/CH_3OH$ 97/3). The fractions were collected and the solvent was evaporated. The residue was crystallized from $CH_3CN$ (10 ml), filtered off, washed with DIPE and dried, yielding 3.4 g of a compound 91 having a molecular weight of 515.4 g and being represented by the formula

EXAMPLE B92

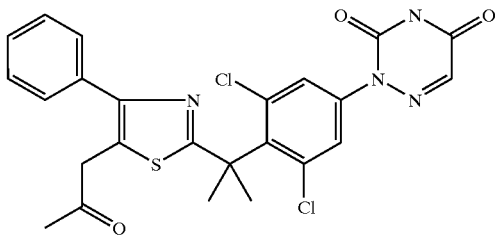

A mixture of intermediate (13) (0.002 mole) in DMF (10 ml) was stirred. 1,1'-carbonylbis-1H-imidazole (0.0025 mole) was added. The mixture was stirred at 40° C. for one hour. 2,2-dimethyl-1,3-Dioxolane-4-methanol (0.004 mole) then 2,3,4,6,7,8,9,10-octahydro-Pyrimido[1,2-a]azepine (0.002 mole) were added. The mixture was stirred at 40° C. for two hours, poured out on ice, acidified with HCl 3N and extracted with $CH_2Cl_2$. The organic layer was separated, washed several times with water, dried ($MgSO_4$), filtered and the solvent was evaporated. The residue (1.2 g) was purified by column chromatography over silica gel (eluent: $CH_2Cl_2/CH_3OH$ 97/3; 15–40 µm). The pure fractions were collected and the solvent was evaporated. The residue (1 g) was crystallized from diethyl ether/DIPE, then the precipitate was filtered off and dried, yielding 0.66 g (54%) of a compound 92 having a molecular weight of 617.5 g, a melting point of 163° C. and being represented by the formula

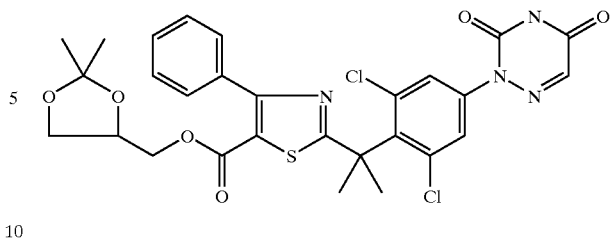

EXAMPLE B93

1-(chloromethoxy)-2-methoxy-Ethane (0.0116 mole) was added dropwise to a solution of intermediate (10) (0.0078 mole) and 1H-imidazole (0.0116 mole) in DMF (80 ml), stirred at room temperature. The reaction mixture was stirred for 16 hours at room temperature, then poured out into water and the aqueous layer was extracted with EtOAc. The separated organic layer was dried, filtered and the solvent evaporated, yielding 2.4 g of a fraction which was purified by column chromatography over silica gel (Merck Art. 11695; eluent: $CH_2Cl_2/CH_3CN$ from 85/15 to 80/20). The desired fractions were collected and the solvent was evaporated, then the product was crystallized from EtOAc/hexane 1/1 (20 ml), filtered off and dried, yielding 0.11 g of a compound 93 having a molecular weight of 605.5 g and being represented by the formula

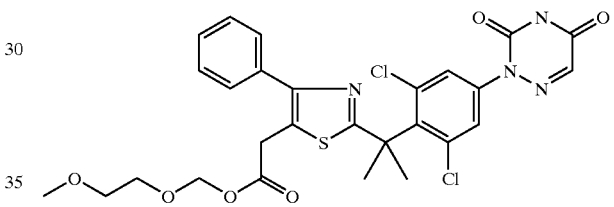

EXAMPLE B94

1-(chloromethoxy)-2-methoxy-Ethane (0.0116 mole) in DMF (10 ml) was added dropwise to compound B74 (0.00783 mole). The reaction mixture was stirred for 16 hours at room temperature, then poured out into water and this mixture was extracted with EtOAc. The separated organic layer was dried, filtered and the solvent evaporated under reduced pressure, yielding 4.7 g of a fraction which was purified by column chromatography over silica gel (eluent: $CH_2Cl_2/EtOAc$ 95/5, then LiChroprep; eluent: $CH_2Cl_2/EtOAc/CH_3CN$ 100/0/0, 0/100/0, 0/0/100), then crystallized from EtOAc/hexane 1/1 (30 ml), filtered off and dried, yield 0.47 g of a compound 94 having a molecular weight of 621.6 g and being represented by the formula

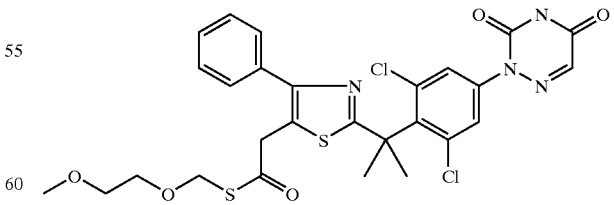

EXAMPLE B95

A mixture of intermediate (10) (0.0078 mole) and sodium hydrocarbonate (0.0086 mole) in DMF (80 ml) was stirred for two hours at room temperature. Sodium iodide (0.0086 mole) was added and a solution of 1-chloro-2-methylpropyl 1-methylethyl ester Carbonic acid (0.0086 mole) in THF (10 ml) was added dropwise. The reaction mixture was stirred overnight at 50° C., then allowed to cool to room temperature. The reaction mixture was poured out into iced water and this mixture was extracted with EtOAc. The separated organic layer was dried (MgSO₄), filtered and the solvent evaporated. The residue was purified by high-performance liquid chromatography over RP BDS Spherical (200 g Hyperprep C18 (100 Å, 8 μm; eluent: [(0.5% NH₄OAc in H₂O)/CH₃CN 90/10)]//CH₃CN (0 minute) 60/40, (24 minutes) 40/60, (up to 32 minutes) 0/100). The product fractions were collected and the solvent was evaporated. The residue was dried under vacuum at 50° C., yielding 0.25 g of a compound 95 having a molecular weight of 675.6 g and being represented by the formula

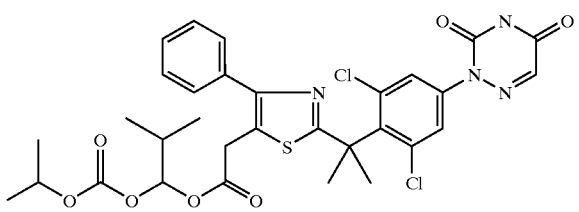

EXAMPLES B96 AND B97

A solution of the intermediate (8) (0.02 mole) and β-bromo-α methyl-γ-oxo-Benzenebutanoic acid (0.02 mol) in ethanol (20 ml) and DMF (20 ml) was stirred for four days at 70° C., then cooled and the solvent was evaporated under reduced pressure. The residue was purified by column chromatography over silica gel (eluent: CH₂Cl₂/EtOAc from 95/5 to 80/200). The desired fractions were collected and the solvent was evaporated, yielding 2.2 g of a fraction A and 8.0 g of a fraction B. The latter was purified by high-performance liquid chromatography over RP BDS Spherical (200 g Hyperprep C18 (100 Å, 8 μm; eluent: [(0.5% NH₄OAc in H₂O)/CH₃CN 90/10)]/CH₃CN (0 minutes) 70/30, (24 minutes) 30/70, (up to 32 minutes) 0/100). The pure fractions were collected, the solvent was evaporated and the resulting product was recrystallized from EtOAc, filtered off and dried, yielding 0.97 g of a compound 96 having a molecular weight of 559.5 g and being represented by the formula

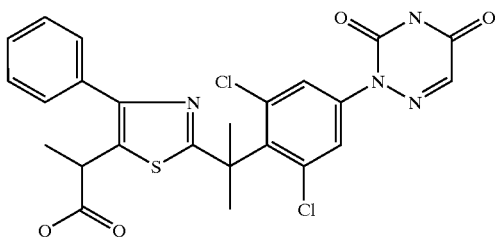

Fraction A was purified by high-performance liquid chromatography over RP BDS Spherical (200 g Hyperprep C18 (100 Å, 8 μm; eluent: [(0.5% NH₄OAc in H₂O)/CH₃CN 90/10)]/CH₃CN (0 min) 65/35,(24 minutes) 65/35, (up to 32 minutes) 0/100). The pure fractions were collected, the solvent was evaporated and the resulting product was recrystallized from EtOAc/hexane 1/1 (20 ml), filtered off and dried, yielding 0.33 g of a compound 97 having a molecular weight of 531.4 g and being represented by the formula

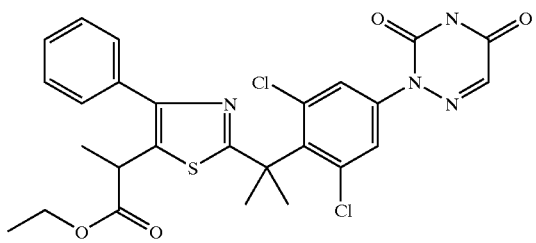

EXAMPLE B98

1,1'-carbonylbis-1H-imidazole (0.012 mole) was added at room temperature to a mixture of compound 97 (0.0088 mole) in DMF (70 ml). The mixture was stirred at room temperature for one hour. Ethanol (20 ml) was added at room temperature. The mixture was stirred for two hours, then the solvent was evaporated under reduced pressure. The residue was purified by column chromatography over silica gel (eluent: CH₂Cl₂/EtOH 99.5/0.5 to 95/5). The pure fractions were collected and the solvent was evaporated. The residue (3.3 g) was stirred in EtOAc/hexane 30/70. The precipitate was filtered off and dried, yielding 2.26 g (46%) of compound 96.

EXAMPLE B99

A solution of A (0.014 mole) in methylene chloride (8 ml) was added dropwise at 5° C. to a solution of methoxyethanol (0.0168 mole) and pyridine (0.0182 mole) in methylene chloride (8 ml) under a nitrogen flow. The mixture was stirred at 10° C. for two hours, then water and methylene chloride were added and the mixture was acidified with HCl 3N. The organic layer was separated, dried (MgSO₄), filtered and the solvent was evaporated, yielding 2.3 g (89%) of a compound 98 having a molecular weight of 182.6 g and being represented by the formula

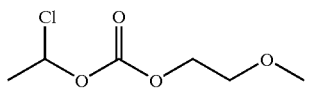

EXAMPLE B100

A solution of intermediate (13) (0.0073 mole), compound 98 (0.0109 mole), sodium hydrocarbonate (0.0073 mole) and potassium iodide (0.0073 mole) in DMF (25 ml) was stirred at 70° C. for 24 hours, then brought to room temperature, poured out into ice water and acidified with HCl 3N. The precipitate was filtered, washed with water and taken up in methylene chloride. The organic layer was separated, dried (MgSO₄), filtered and the solvent was evaporated. The residue (4.6 g) was purified by column chromatography over silica gel (eluent: CH₂Cl₂/CH₃OH 99/1; 15–40 μm). The pure fractions were collected and the solvent was evaporated, yielding 1.4 g (31%) of a compound 99 having a molecular weight of 649.5 g, a melting point of 88° C. and being represented by the formula

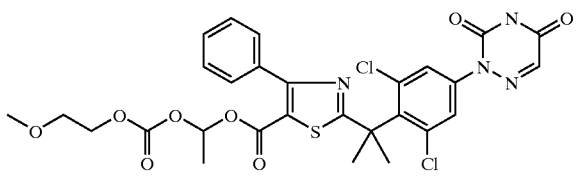

EXAMPLE B101

Sodium hydroxide 1M (0.175 ml) was added to compound 3 (0.00008716 mole) in THF (2 ml) and the reaction mixture was stirred for 30 minutes at room temperature. The resulting product was purified by reversed-phase high performance liquid chromatography. The fractions were collected and the solvent was evaporated. The aqueous concentrate was desalted on column and eluted with $CH_3CN$, then the product fractions were collected and the solvent was evaporated at room temperature, yielding 0.011 g (21%) of a compound 100 having a molecular weight of 649.4 g, and being represented by the formula

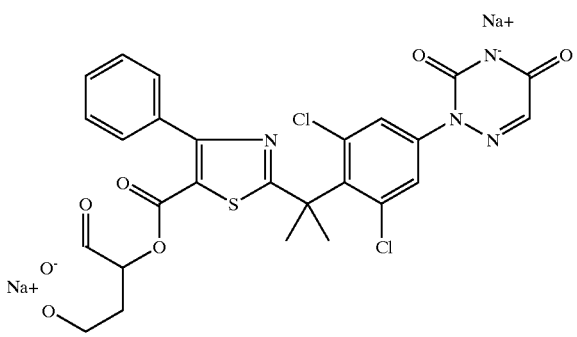

EXAMPLE B102

1,1'-carbonylbis-1H-imidazole (0.0116 mole) was added at room temperature to a stirring mixture of intermediate (10) (0.00773 mole) in methylene chloride (75 ml) under a nitrogen flow. The mixture was stirred for two hours. A solution of N-[(1,1-dimethylethoxy)carbonyl]-, methyl ester L-Serine. (0.0116 mole) in methylene chloride (5 ml) was added. The mixture was stirred overnight and then washed three times with water. The organic layer was separated, dried ($MgSO_4$), filtered and the solvent was evaporated. The residue (8.6 g) was purified by column chromatography over silica gel (eluent: $CH_2Cl_2$/THF 98/2). The desired fractions were collected and the solvent was evaporated. The residue (5.4 g) was purified again by column chromatography over silica gel (eluent: $CH_2Cl_2$/THF 98/2). The desired fractions were collected and the solvent was evaporated. Toluene was added. The solvent was evaporated. The residue was stirred in EtOAc/DIPE 1/1 (35 ml) overnight. The precipitate was stirred in EtOAc/DIPE 1/1, filtered off, washed with EtOAc/DIPE 1/1 and DIPE, and dried in vacuo at 50° C. The residue was recrystallized from $CH_3CN$ and DIPE. The precipitate was filtered off, washed with $CH_3CN$ and DIPE, and dried in vacuo at 50° C., yielding 1.72 g (31%) of a compound 101 having a molecular weight of 718.6 g and being represented by the formula

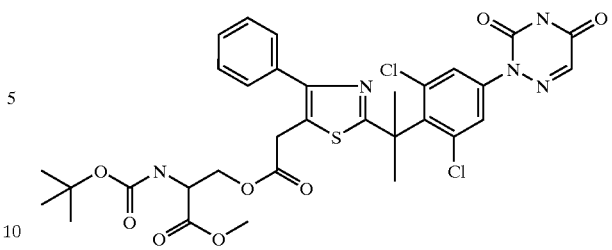

EXAMPLE B103

3-bromodihydro-2(3H)-furanone (0.0076 mole) was added dropwise at room temperature to a mixture of compound 96 (0.0038 mole) and 3-bromodihydro2(3H)-Furanone (0.008 mole) in $CH_3CN$ (80 ml). The mixture was stirred at 50° C. overnight, then poured out into water and separated into its layers. The aqueous layer was extracted with EtOAc. The combined organic layer was dried, filtered and the solvent was evaporated under reduced pressure. The residue (2.7 g) was purified by column chromatography over silica gel (eluent: $CH_2Cl_2$/EtOAc 99.5/0.5 to 95/5). The pure fractions were collected and the solvent was evaporated, yielding 0.6 g of a fraction which was purified again by column chromatography over silica gel (eluent: $CH_2Cl_2$/EtOAc 99.5/0.5 to 95/5). The pure fractions were collected and the solvent wasevaporated, yielding 0.1 g (4.3%) of a compound 102 having a molecular weight of 615.5 g and being represented by the formula

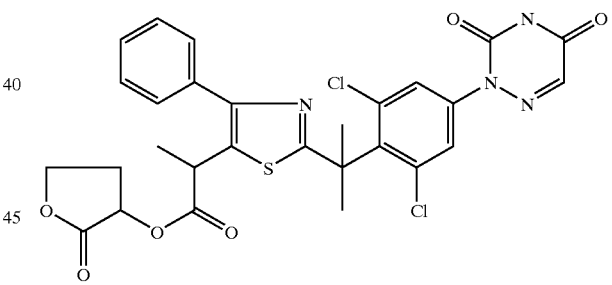

EXAMPLE B104

A solution of chloro(methylthio)-Methane (0.007 mole) in DMF (10 ml) was added dropwise to compound 74 (0.0043 mole) at room temperature. The reaction mixture was stirred overnight at room temperature, then poured out into water and extracted with EtOAc. The separated organic layer was dried, filtered and the solvent was evaporated under reduced pressure. The residue was purified by column chromatography over silica gel (eluent: $CH_2Cl_2$/EtOAc from 99.5/0.5 to 95/5). The desired fractions were collected and the solvent was evaporated, yielding 1.03 g of a compound 103 having a molecular weight of 593.6 g and being represented by the formula

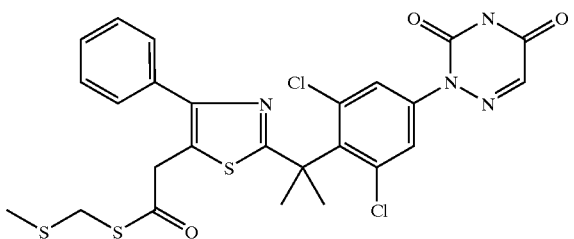

EXAMPLE B105

Chloro-3-benzoic acid (0.0042 mole) was added at room temperature to a mixture of compound 103 (0.0042 mole) in methylene chloride (120 ml). The mixture was stirred at room temperature overnight. The solvent was evaporated under reduced pressure. The residue was purified by column chromatography over silica gel (eluent: $CH_2Cl_2$/EtOAc 99.5/0.5 to 95/5). The pure fractions were collected and the solvent was evaporated. The residue was stirred in EtOAc/hexane 50/50 (20 ml). The precipitate was filtered off and dried, yielding 1.85 g (72%) of a compound 104 having a molecular weight of 609.6 g, a melting point of 154° C. and being represented by the formula

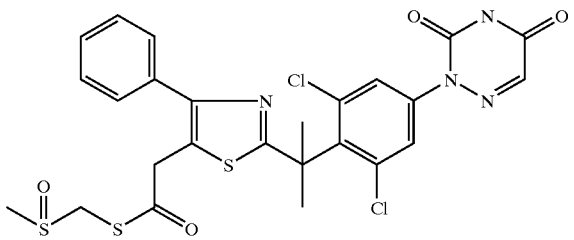

EXAMPLE B106

A mixture of intermediate 8 (6.75 g) in ethanol (80 ml) and DMF (20 ml) was stirred and cooled on an ice-bath at 5° C. (2-bromo-1-phenyl-1,3-Butanedione (5.4 g) in ethanol (20 ml) was added dropwise over 30 minutes at 5° C. The reaction mixture was stirred for 30 minutes at 5C, then for 18 hours at room temperature. The solvent was evaporated and the residue was purified by high performance liquid chromatography over silica gel (eluent: $CH_2Cl_2$/$CH_3OH$/THF 97/1/2), yielding 5 g of a first product fraction, the solvent of which was evaporated. This product fraction was stirred in DIPE, filtered off and dried, yielding 1.25 g of a compound 105 having a molecular weight of 501.4 g, a melting point of 212° C. and being represented by the formula

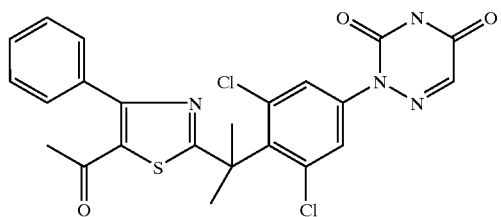

EXAMPLE B107

A mixture of bromine (0.0097 mole) in methylene chloride (8 ml) was added dropwise at a temperature between 10° C. and 20° C. to a solution of 2-(2-methyl 1,3-dioxolan-2-yl)-1-phenyl-Ethanone, (0.0097 mole) in methylene chloride (50 ml) under a nitrogen flow. The resulting mixture was stirred at 5° C. for 30 minutes. A satured $NaHCO_3$ solution was added. The organic layer was separated, dried ($MgSO_4$), filtered and the solvent was evaporated, yielding 2.7 g of a compound 106 having a molecular weight of 285.1 g and being represented by the formula

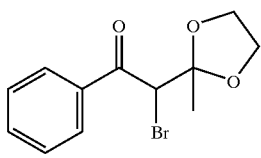

This product was used without further purification in the next example.

EXAMPLE B108

A mixture of intermediate 8 (0.0073 mole) and compound 106 (0.0095 mole) in ethanol (30 ml) and DMF (5 ml) was stirred at 80° C. for 4 hours. The solvent was evaporated. The mixture was taken up in AcOEt and washed three times with $H_2O$/NaCl. The organic layer was separated, dried ($MgSO_4$), filtered and the solvent was evaporated. The residue (5 g) was purified by column chromatography over silica gel (eluent: $CH_2Cl_2$/$CH_3OH$ 99/1; 15–40 μm). Two fractions were collected and the solvent was evaporated. The first fraction (0.4 g) was crystallized from diethyl ether, the precipitate was filtered off and dried, yielding 0.29 g of compound 105. The second fraction (0.44 g) was crystallized from diethyl ether, the precipitate was filtered off and dried, yielding 0.19 g of a compound 107 having a molecular weight of 501.4 g, a melting point of 174° C. and being represented by the formula

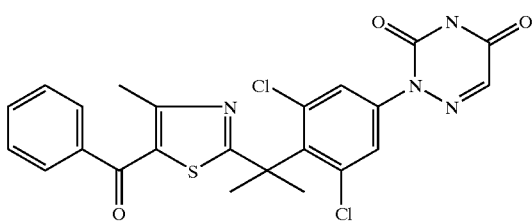

EXAMPLE B109

A mixture of intermediate (13) (0.00496 mole), iodomethyl butyrate (0.00992 mol) and sodium hydrocarbonate (0.00496 mole) in DMF (15 ml) was stirred at 70° C. for 48 hours, poured out on ice and acidified with HCl 3N until pH 4–5 was obtained. The precipitate was filtered, washed with water, taken up in methylene chloride and washed again with water. The organic layer was separated, dried ($MgSO_4$), filtered and the solvent was evaporated. The residue (3 g) was purified by column chromatography over silica gel (eluent: $CH_2Cl_2$/$CH_3OH$ 99.5/0.5; 15–40 μm). The pure fractions were collected and the solvent was evaporated. The residue (0.25 g) was crystallized from diethyl ether/DIPE. The precipitate was filtered off and dried, yielding 0.2 g (6.6%) of a compound 108 having a molecular weight of 603.5 g, a melting point of 146° C. and being represented by the formula

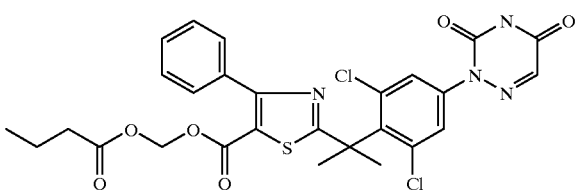

EXAMPLE B110

A mixture of 1-chloroethyl ester Carbonochloridic acid (0.014 mole) in methylene chloride (8 ml) was added at 5° C. to a solution of 2-(methylsulfonyl)-Ethanol (0.017 mole) and pyridine (0.018 mole) in methylene chloride (8 ml) under a nitrogen flow. The resulting mixture was stirred at 10° C. for two hours and $H_2O/CH_2Cl_2$ was added. The mixture was acidified with HCl 3N. The organic layer was separated, dried ($MgSO_4$), filtered and the solvent was evaporated, yielding 2.22 g (68%) of a compound 109 having a molecular weight of 230.7 g and being represented by the formula

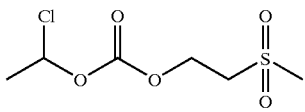

EXAMPLE B111

A solution of intermediate (13) (0.0054 mole), compound 109 (0.0082 mole), sodium hydrocarbonate (0.0054 mole) and potassium iodide (0.0054 mole) in DMF (20 ml) was stirred at 70° C. for 24 hours, brought to room temperature, poured out into ice water, acidified with HCl 3N and filtered. The precipitate was washed with water and taken up in methylene chloride. The organic layer was separated, dried ($MgSO_4$), filtered and the solvent was evaporated. The residue (3.5 g) was purified by column chromatography over silica gel (eluent: $CH_2Cl_2/CH_3OH$ 99/1; 15–40 μm). The pure fractions were collected and the solvent was evaporated, yielding 0.6 g (16%) of a compound 110 having a molecular weight of 697.6 g, a melting point of 104° C. and being represented by the formula

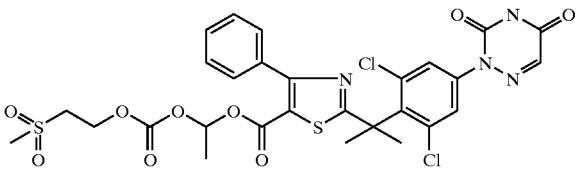

EXAMPLE B112

A mixture of intermediate (13) (0.003 mole) and 1,1'-carbonylbis-1H-imidazole (0.0039 mole) in DMF (10 ml) was stirred at 40° C. for one hour, then brought to room temperature. 4-(hydroxymethyl) 1,3-Dioxolane-2-thione (0.006 mole) was added. The mixture was stirred at room temperature for 60 hours, poured out into water and acidified with HCl 3N. The precipitate was filtered, washed with water, taken up in EtOAc and washed again twice with water. The organic layer was separated, dried ($MgSO_4$), filtered and the solvent was evaporated. The residue (2.08 g) was purified by column chromatography over silica gel (eluent: $CH_2Cl_2/CH_3OH$ 99/1; 15–40 μm). The pure fractions were collected and the solvent was evaporated. The residue was crystallized from diethyl ether, the precipitate was filtered off and dried, yielding 0.35 g of a compound 111 having a molecular weight of 619.5 g, a melting point of 130° C. and being represented by the formula

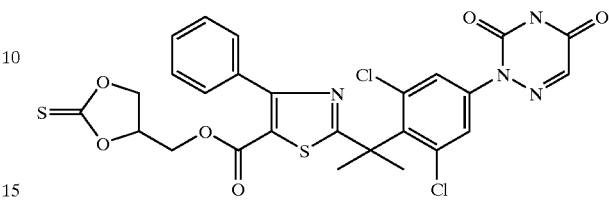

EXAMPLE B113

A mixture of intermediate (10) (0.0039 mole) and diethyl-, 1-chloroethyl ester Carbamic acid (0.0039 mole) in $CH_3CN$ (40 ml) was stirred at 60° C. Triethylamine (0.0039 mole) was added. The reaction mixture was stirred for 24 hours. The solvent was evaporated. The residue was purified by flash chromatography over silica gel (eluent: $CH_2Cl_2/CH_3OH$ 99.7/0.3). The desired fractions were collected and the solvent was evaporated till dryness. The residue was stirred in hexane, the precipitate was filtered off, washed and driedunder vacuum at 50° C., yielding 0.4 g of a compound 112 having a molecular weight of 660.6 g and being represented by the formula

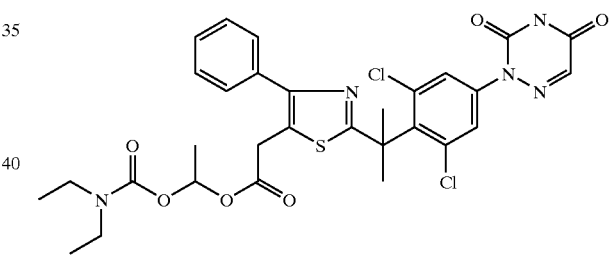

EXAMPLE B114

1,1'-carbonylbis-1H-imidazole (0.0084 mole) was added to a solution of intermediate (10) (0.0056 mole) in DMF (30 ml). The reaction mixture was stirred for one hour at room temperature. C (0.0112 mol) was added. Then (0.0056 mol) was added at room temperature and the resulting reaction mixture was stirred for two hours at room temperature. The reaction mixture was poured out into water and the aqueous layer was extracted with EtOAc. The organic layer was separated, dried, filtered and the solvent evaporated under reduced pressure. The residue was purified by column chromatography over silica gel (eluent: $CH_2Cl_2$/EtOAc 99.5/0.5 up to 96/4). The product fractions werecollected and the solvent was evaporated under reduced pressure. The residue was dried under vacuum, yielding 0.95 g of a fraction which was dried undervacuum at 70° C. for two days, yielding 0.78 g (21%) of a compound 113 having a molecular weight of 649.5 g and being represented by the formula

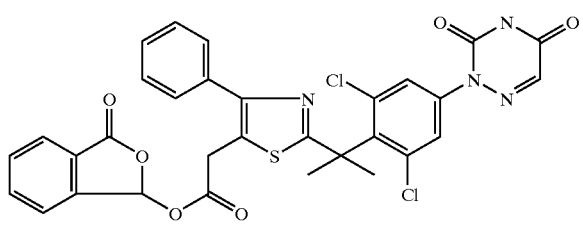

EXAMPLE B115

A mixture of published as EP98203148.6 (0.0085 mole) in THF (70 ml) was added dropwise at 0° C. to a suspension of lithium aluminum hydride (0.0085 mole) in THF (10 ml) under a nitrogen flow. The mixture was stirred at a temperature between 5° C. and 15° C. for three hours. Water and EtOAc were added. The mixture was acidified with HCl 3N. The organic layer was separated, dried (MgSO4), filtered and the solvent was evaporated. The residue (8.9 g) was purified by column chromatography over silica gel (eluent: $CH_2Cl_2/CH_3OH$ 98/2; 15–35 μm). The pure fractions were collected and the solvent was evaporated. The residue was crystallized from $CH_3CN$. The precipitate was filtered off and dried, yielding 0.44 g of a compound 114 having a molecular weight of 489.4 g and being represented by the formula

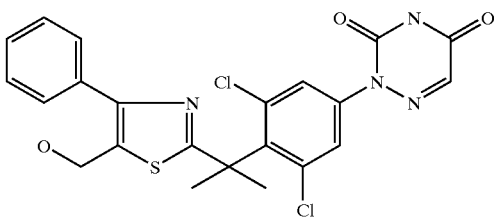

EXAMPLE B116

Thionyl chloride (0.0049 mole) was added at room temperature to a mixture of compound 114 (0.0033 mole) in methylene chloride (120 ml). The mixture was stirred at room temperature for two hours and washed with NaHCO3 (saturated). The organic layer was separated, dried (MgSO$_4$), filtered and the solvent was evaporated, yielding 1.7 g (100%) of a compound 115 having a molecular weight of 507.8 g and being represented by the formula

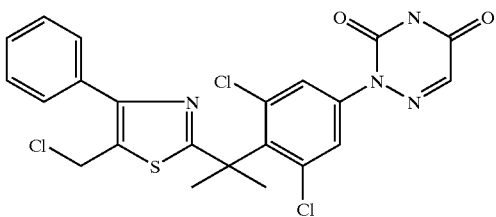

EXAMPLE B117

A mixture of compound 115 (0.0033 mole), dihydro-3-mercapto-2(3H)-Furanone (0.0065 mole) and potassium carbonate (0.0065 mole) in $CH_3CN$ (70 ml) and DMF (5 ml) was stirred at 90° C. for two hours, brought to room temperature, evaporated, taken up in water, acidified with HCl 3N, extracted with EtOAc and washed with water. The organic layer was separated, dried (MgSO$_4$), filtered and the solvent was evaporated. The residue was purified by column chromatography over silica gel (eluent: $CH_2Cl_2/CH_3OH$ 99/1; 15–40 μm). One fraction was collected and, after evaporation of the solvent, taken up in DIPE and filtered, yielding 0.43 g of a compound 116 having a molecular weight of 589.5 g, a melting point of 100° C. and being represented by the formula

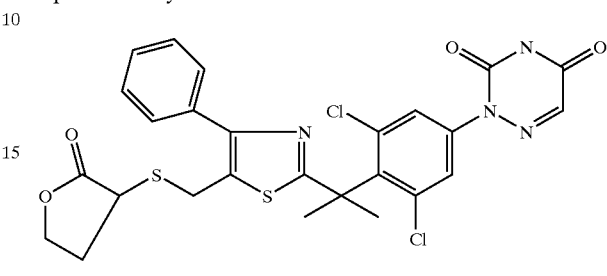

EXAMPLE B118

1,1'-carbonylbis-1H-imidazole (0.941 g) was added to a suspension of intermediate (10) (0.00387 mole) in methylene chloride (40 ml) and stirred at room temperature. The mixture was stirred for one hour at room temperature. Methyl-2-amino-2-propanol (0.0058 mole) was added and the reaction mixture was stirred overnight at room temperature. The reaction mixture was washed with water. The layers were separated. The organic layer was dried (MgSO$_4$), filtered and the solvent was evaporated under reduced pressure. The residue was purified by column chromatography over silica gel (eluent: $CH_2Cl_2$/EtOAc 99/1 to 95/5). The pure fractions were collected and the solvent was evaporated, resulting in a fraction which was stirred in EtOAc. The precipitate was filtered off and dried, yielding 0.5 g (22%) of a compound 117 having a molecular weight of 588.5 g and being represented by the formula

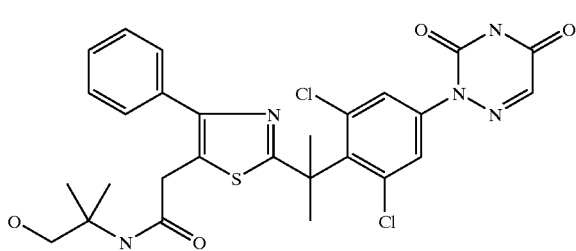

EXAMPLE B119

A mixture of intermediate (13) (0.003 mole) and 1,1'-carbonylbis-1H-imidazole (0.045 mole) in DMF (15 ml) was stirred at 40° C. for one hour. 1,4-cyclohexanediol (0.015 mole) was added then a solution of 1,8-diazabicyclo (5.4.0) undecene-7 (0.003 mole) in DMF (3 ml). The mixture was stirred at 40° C. for two hours, poured out into water, acidified with HCl 3N, extracted with EtOAc and washed with water. The organic layer was separated, dried (MgSO$_4$), filtered and the solvent was evaporated. The residue was purified by column chromatography over silica gel (eluent: $CH_2Cl_2/CH_3OH$ 96/4; 15–40 μm). The pure fractions were collected and the solvent was evaporated, yielding 0.86 g (47%) of a compound 118 having a molecular weight of 601.5 g and being represented by the formula

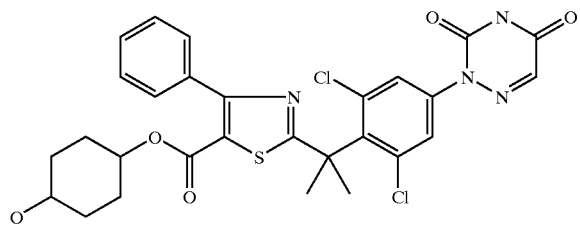

Further analysis shows that it consists of a mixture of 35% of an isomer with a melting point of 141° C. and 65% of another isomer with a melting point of 128° C.

EXAMPLE B120

A mixture of intermediate (13) (0.0018 mole) and 1,1'-carbonylbis-1H-imidazole (0.0023 mole) in DMF (8 ml) was stirred at 40° C. for one hour. A solution of 1,4-di (hydroxymethyl) cyclohexane (0.0089 mole) and 1,8-diazabicyclo (5.4.0) undecene-7 (0.0018 mole) in DMF (3 ml) was added. The mixture was stirred at 60° C. for two hours, brought to room temperature and water was added. The mixture was acidified with HCl 3N, filtered and the precipitate was washed with water, taken up in EtOAc and washed with water. The organic layer was separated, dried (MgSO$_4$), filtered and the solvent was evaporated. The residue was purified by column chromatography over silica gel (eluent: CH$_2$Cl$_2$/CH$_3$OH 98/2; 15–40 μm). The pure fractions were collected and the solvent evaporated, yielding a fraction which was crystallized from diethyl ether/CH3CN. The precipitate was filtered off and dried, yielding 0.282 g of a compound 119 having a molecular weight of 629.6 g and being represented by the formula

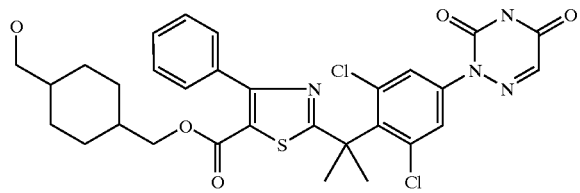

EXAMPLE B121

A mixture of intermediate (13) (0.0028 mole), tetrahydro-3-iodo-2H-Pyran-2-one (0.0056 mole) and sodium hydrocarbonate (0.0028 mole) in DMF (10 ml) was stirred at 70° C. for two hours, brought to room temperature, poured out into water and acidified. The precipitate was filtered, washed with water, taken up in EtOAc and washed with water. The organic layer was separated, dried (MgSO$_4$), filtered and the solvent was evaporated, yielding 2.44 g of a compound 120 having a molecular weight of 601.5 g and being represented by the formula

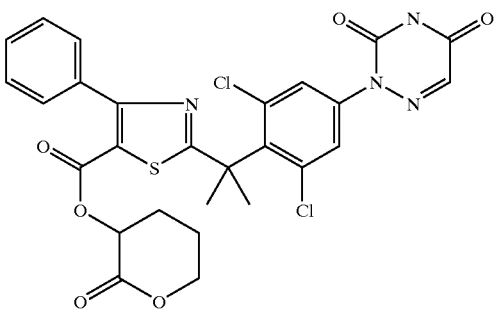

EXAMPLE B122

Compound 120 (0.0028 mole) was chromatographied over 300 g of silica (eluent: CH$_2$Cl$_2$/CH$_3$OH 99/1). One fraction was collected and, after evaporating the solvent, was purified by column chromatography over Kromasil (eluent: CH$_3$CN/AcNH$_4$ 65/35). One fraction was collected and, after evaporating the solvent, was taken up in pentane and filtered, yielding 0.061 g of a compound 121 having a molecular weight of 633.5 g, a melting point of 100° C. and being represented by the formula

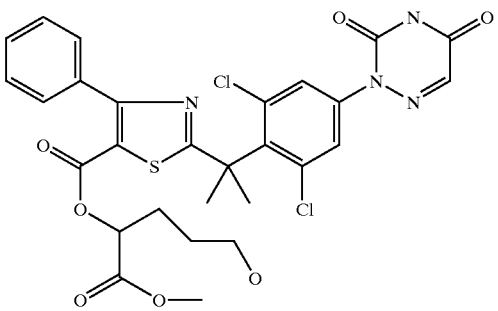

EXAMPLE B123

1,1'-carbonylbis-1H-imidazole (0.0116 mole) was added at room temperature under a nitrogen flow to a stirring mixture of intermediate (10) (0.00773 mole) in methylene chloride (75 ml). The mixture was stirred for three hours. A solution of (2-hydroxyethyl)(phenylmethyl-)1,1-dimethylethyl ester Carbamic acid, (0.0116 mole) in methylene chloride (5 ml) was added. The mixture was stirred overnight and then washed three times with water. The organic layer was separated, dried (MgSO$_4$), filtered and the solvent was evaporated. The residue was purified by column chromatography over silica gel (eluent: CH$_2$Cl$_2$/THF 98/2). The desired fractions were collected and the solvent was evaporated. Toluene was added, then the solvent was evaporated. The residue was purified again by high performance liquid chromatography over Hyperprep (eluent: (0.5% ammonium acetate aqueous solution/CH$_3$CN 90/10)/CH$_3$CN 40/60 and 3/97; column: C18 HS BDS 100 Å 8 μm). The desired fractions were collected and the solvent was evaporated. The residue was dissolved in CH$_2$Cl$_2$/EtOAc, filtered over a paper-frit and the filtrate was evaporated. The residue was stirred in hexane overnight. The precipitate was filtered off, washed with hexane and dried in vacuo at 50° C., yielding 3.2 g of a compound 122 having a molecular weight of 633.5 g and being represented by the formula

EXAMPLE B124

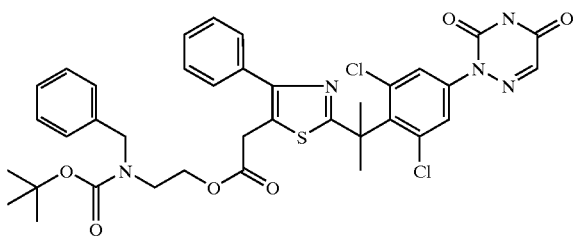

Trifluoroacetic acid (3 ml) was added to a solution of compound 101 (0.00122 mole) in methylene chloride (10 ml) and stirred at room temperature under a nitrogen flow for three hours. The solvent was evaporated, then toluene was added and the solvent was again evaporated. The residue was stirred in methylene chloride (15 ml). The mixture was treated with gaseous hydrogen chloride for 15 minutes. Some toluene was added, then all solvent was evaporated again. The resultant oil was stirred in 2-propanone, decanted, then after standing for two days under a nitrogen atmosphere, the mixture was stirred overnight in DIPE, filtered off, washed and dried under vacuum at 50° C., yielding 0.34 g of a compound 123 having a molecular weight of 655.0 g and being represented by the formula

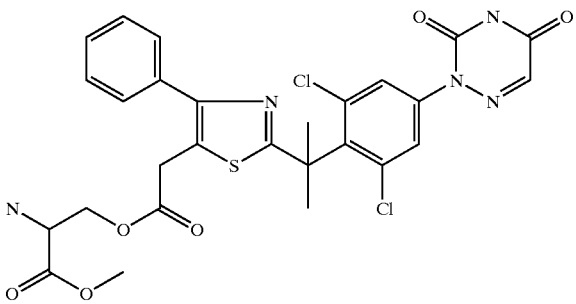

EXAMPLE B125

A mixture of intermediate (13) (0.0024 mole) and 1,1'-carbonylbis-1H-imidazole (0.0031 mole) in DMF (8 ml) was stirred at 40° C. for one hour. A mixture of dihydro-3-hydroxy-4,4-dimethyl-2(3H)-Furanone (0.0048 mole) and 1,8-diazabicyclo (5.4.0) undecene-7 (0.0024 mole) in DMF (1 ml) was added. The mixture was stirred at 40° C. for two hours, brought to room temperature, poured out into HCl 1N and filtered. The precipitate was washed with water, taken up in EtOAc and washed with water. The organic layer was separated, dried (MgSO₄), filtered and the solvent was evaporated. The residue was crystallized from diethyl ether/CH₃CN. The precipitate was filtered off and dried, yielding 0.78 g (53%) of the (R) isomer (having an optical rotation, measured in DMF, of +16.23°) of a compound 124 having a molecular weight of 615.5 g, a melting point of 248° C. and being represented by the formula

EXAMPLE B126

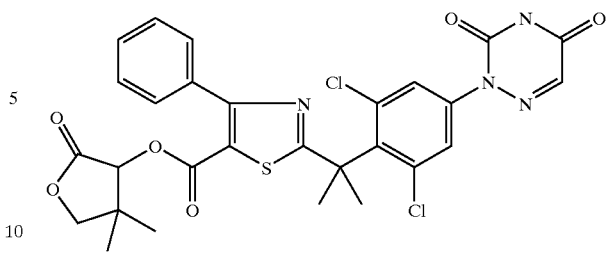

A mixture of intermediate (13) (0.0029 mole), chloromethyl cyclohexane carboxylate (0.0058 mole), sodium hydrocarbonate (0.0029 mole) and potassium iodide (0.0029 mole) in DMF (10 ml) was stirred at 70° C. for 12 hours, brought to room temperature and HCl 1N was added. The mixture was filtered, the insoluble was taken up in EtOAc and washed with water. The organic layer was separated, dried (MgSO₄), filtered and the solvent was evaporated. The residue was purified by column chromatography over silica gel (eluent: CH₂Cl₂/CH₃OH 99/1; 15–40 μm). One fraction was collected and, after evaporating the solvent, was crystallized from diethyl ether. The precipitate was filtered off and dried, yielding 0.5 g of a compound 125 having a molecular weight of 643.5 g, a melting point of 130° C. and being represented by the formula

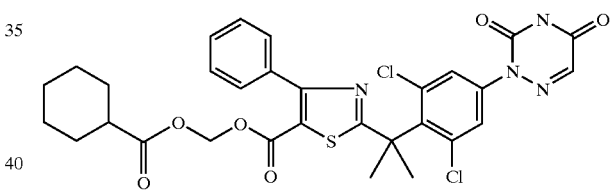

EXAMPLE B127

A mixture of intermediate (13) (0.00278 mole) and 1,1'-carbonylbis-1H-imidazole (0.0036 mole) in DMF (9 ml) was stirred at 40° C. for one hour. A solution of (−)-(D) dihydro-3-hydroxy-4,4-dimethyl-2(3H)Furanone (0.00556 mole) and 1,8-diazabicyclo (5.4.0) undecene-7 (0.00278 mole) in DMF (1 ml) was added. The mixture was stirred at 40° C. for two hours, then brought to room temperature. HCl 1N was added. The precipitate was filtered, washed with water, taken up in EtOAc and washed again with water. The organic layer was separated, dried (MgSO₄), filtered and the solvent was evaporated. The residue was purified by column chromatography over silica gel (eluent: CH₂Cl₂/CH₃OH 99/1; 35–70 μm). The pure fractions were collected and the solvent was evaporated. The residue was crystallized from diethyl ether/CH₃CN. The precipitate was filtered off and dried, yielding 1.15 g (68%) of the (S) isomer (having an optical rotation, measured in DMF, of −11.84°) of a compound 126 having a molecular weight of 615.5 g, a melting point of 244° C. and being represented by the formula

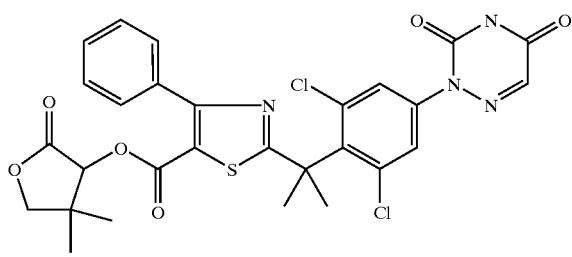

EXAMPLE B128

Compound 97 (0.027 mole) was separated by chiral column chromatography over Chiralpak AD (500 g) (eluent: hexane/ethanol +1% trifluoroacetic acid 70/30). Two fractions were collected and, after evaporating the solvent, gave two 0.7 g oils which were treated with a saturated aqueous sodium hydrocarbonate solution. This mixture was extracted with methylene chloride. and co-evaporated with EtOAc. The residue was stirred in DIPE, washed with DIPE, and dried overnight under vacuum at 50° C., yielding 0.5 g of a first enantiomer (having an optical rotation, measured in methanol, of −63.95°) and 0.5 g of a second enantiomer (having an optical rotation, measured in methanol, of +61.36°).

EXAMPLE B129

A mixture of 2-methyl-, 1,1-dioxide1,2,5-Thiadiazolidin (0.014 mole), bromo-2-ethanol (0.028 mole) and potassium carbonate (0.0167 mole) in $CH_3CN$ (15 ml) was stirred at 80° C. for 60 hours and bromo-2-ethanol (0.014 mole) was further added. The mixture was stirred and refluxed for 12 hours and bromo-2-ethanol (0.014 mole) was further added. The mixture was stirred and refluxed for 12 hours, brought to room temperature and filtered. The precipitate was washed with methylene chloride and the mixture was evaporated. The residue was purified by column chromatography over silica gel (eluent: $CH_2Cl_2/CH_3OH$; 98/2 35–70 μm). One fraction was collected and the solvent was evaporated, yielding 0.91 g of a compound 127 having a molecular weight of 180.2 g and being represented by the formula

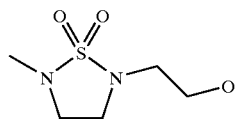

EXAMPLE B130

A mixture of intermediate (13) (0.0024 mole) and 1,1'-carbonylbis-1H-imidazole (0.0031 mole) in DMF (6 ml) was stirred at 40° C. for one hour. A solution of compound 127 (0.0029 mole) and 1,8-diazabicyclo (5.4.0) undecene-7 (0.0024 mole) in DMF (1 ml) was added. The mixture was stirred at 40° C. for four hours, brought to room temperature and ice water was added. The mixture was acidified with HCl 3N and filtered. The precipitate was washed with water, taken up in methylene chloride and washed with water. The organic layer was separated, dried ($MgSO_4$), filtered and the solvent was evaporated. The residue was purified by column chromatography over silica gel (eluent: $CH_2Cl_2/CH_3OH$ 99/1; 15–40 μm). One fraction was collected and, after evaporation of the solvent, was taken up in diethyl ether and filtered, yielding 0.43 g (26%) of a compound 128 having a molecular weight of 665.6 g, a melting point of 112° C. and being represented by the formula

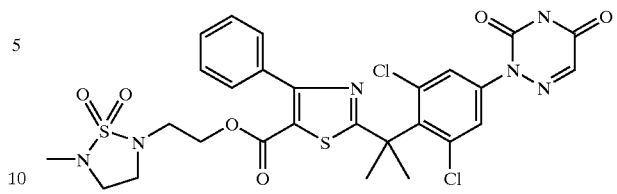

EXAMPLE B131

A solution of compound 105 (0.0030 mole) in THF (10 ml) was stirred at room temperature. A solution of B (0.0028 mol) in THF (10 ml) was added slowly and dropwise. The reaction mixture was stirred for two and a half hours at room temperature. The precipitate was filtered off, washed with THF and the filtrate was evaporated under reduced pressure. The residue was dissolved in methylene chloride, washed with water, dried ($MgSO_4$), filtered and the solvent was evaporated, yielding 1.7 g of a compound 129 having a molecular weight of 580.3 g and being represented by the formula

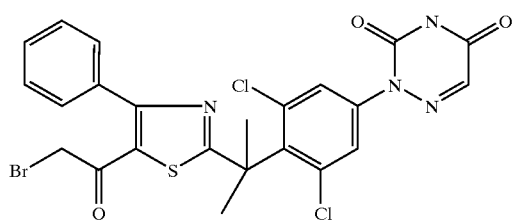

EXAMPLE B132

A mixture of compound 129 (0.003 mole), dihydro-3-mercapto-2(3H)-Furanone (0.006 mole) and potassium carbonate (0.006 mole) in $CH_3CN$ (20 ml) and DMF (3 ml) was stirred for 90 minutes at 90° C. The mixture was allowed to cool to room temperature. The reaction was quenched with water (25 ml) and extracted twice with EtOAc. The separated organic layer was dried ($MgSO_4$), filtered and the solvent evaporated. The residue was purified by flash column chromatography over silica gel (eluent: $CH_2Cl_2/CH_3OH$ 99.8/0.2). The desired fractions were collected and the solvent was evaporated. The residue was purified by high performance liquid chromatography over silica gel (eluent: $CH_2Cl_2/CH_3OH$ from 100/0 to 50/50). The product fractions were collected and the solvent was evaporated. The residue was stirred in DIPE, filtered off, washed and dried under vacuum at 50° C., yielding 0.35 g of a compound 130 having a molecular weight of 617.5 g and being represented by the formula

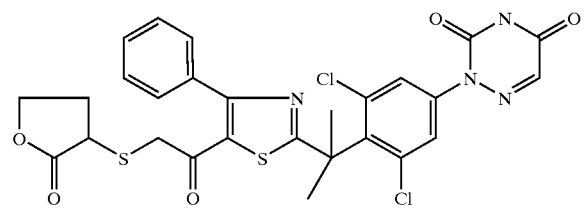

EXAMPLE B133

A mixture of intermediate (13) (0.004 mole) and 1,1'-carbonylbis-1H-imidazole (0.0052 mole) in DMF (13 ml)

was stirred at 40° C. for one hour. A solution of dihydro-3,4-dihydroxy-,(3R,4R)-2(3H)-furanone (0.008 mole) and 1,8-diazabicyclo (5.4.0) undecene-7 (0.004 mole) in DMF (2 ml) was added. The mixture was stirred at 40° C. for five hours then at room temperature overnight and HCl 0.5N was added. The mixture was filtered and the precipitate was washed with water, taken up in EtOAc and washed with water. The organic layer was separated, dried (MgSO$_4$), filtered and the solvent was evaporated. The residue was purified by column chromatography over silica gel (eluent: CH$_2$Cl$_2$/CH$_3$OH 97/3; 15–40 μm). Two fractions were collected and the solvent was evaporated. The first fraction (0.25 g) was taken up in DIPE and filtered, yielding 0.2 g of a compound 131 having a molecular weight of 603.4 g, a melting point of 144° C., an optical rotation (measured in methanol) of −44.95° and being represented by the formula

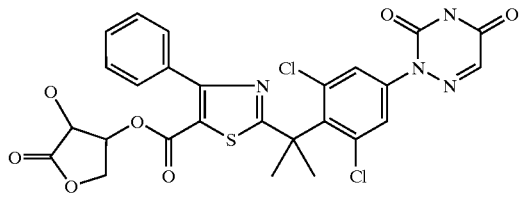

The second fraction consists of 0.3 g of a compound 132 having a molecular weight of 635.5 g, a melting point of 110° C., an optical rotation (measured in methanol) of −14.8° and being represented by the formula

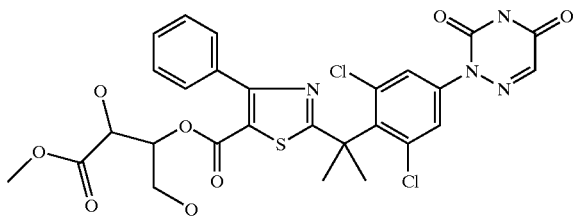

EXAMPLE B134

1,1'-carbonylbis-1H-imidazole (0.0027 mole) was added to a solution of intermediate (13) (0.0021 mole) in DMF (10 ml). The mixture was stirred at 40° C. for one hour and 1-(hydromethyl)-,γ-lactone Cyclohexaneglycolic acid (0.0032 mole) then 1,8-diazabicyclo (5.4.0) undecene-7 (0.0021 mole) were added. The mixture was stirred at 40° C. for 12 hours, poured out into ice water and acidified with HCl 3N. The precipitate was filtered and washed with water. The mixture was dried, taken up in methylene chloride and washed with water. The organic layer was separated, dried (MgSO$_4$), filtered and the solvent was evaporated. The residue was purified by column chromatography over silica gel (eluent:CH2Cl2/CH3OH 99/1; 15–40 μm). The pure fractions were collected and the solvent was evaporated, giving 0.6 g of a fraction which was crystallized from CH$_3$CN/diethyl ether. The precipitate was filtered off and dried, yielding 0.31 g (22%) of a compound 133 having a molecular weight of 655.6 g and being represented by the formula.

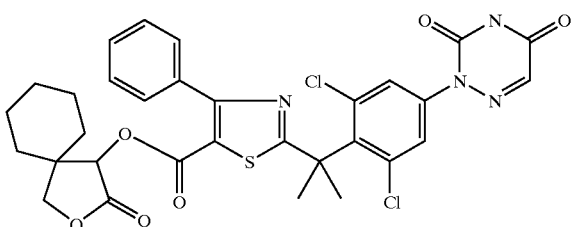

EXAMPLE B135

Hexadecanoic acid chloride (0.002 mole) was added slowly at 0° C. to a solution of compound 65 (0.002 mole) and triethylamine (0.003 mole) in methylene chloride (20 ml). The mixture was stirred at room temperature for five hours and poured out into water. The organic layer was separated, dried (MgSO$_4$), filtered and the solvent was evaporated. The residue (1.9 g) was purified by column chromatography over silica gel (eluent: CH$_2$Cl$_2$/CH$_3$OH 99.5/0.5;15–40 μm). Two fractions were collected and after evaporation of the solvent, were crystallized from DIPE. The precipitate was filtered off and dried, yielding 0.27 g (17%) of a compound 134 having a molecular weight of 799.9 g and being represented by the formula

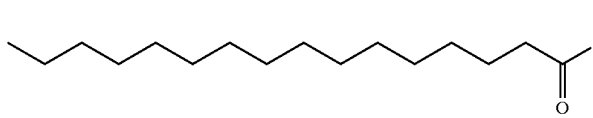

EXAMPLE B136

A mixture of intermediate (13) (0.006 mole) and 1,1'-carbonylbis-1H-imidazole (0.0077 mole) in DMF (25 ml) was stirred at 40° C. for one hour. A solution of dihydro-3-hydroxy-4,4-dimethyl-2(3H)-Furanone (0.012 mole) and 1,8-diazabicyclo (5.4.0) undecene-7 (0.006 mole) in DMF (5 ml) was added. The mixture was stirred at 40° C. for three hours, then brought to room temperature, poured out into HCl 1N, filtered, taken up in EtOAc and washed with water. The organic layer was separated, dried (MgSO$_4$), filtered and the solvent was evaporated. The residue (8.9 g) was purified by column chromatography over silica gel (eluent: CH$_2$Cl$_2$/CH$_3$OH 99/1;15–35 μm). The pure fractions were collected and the solvent was evaporated. The residue was crystallized from diethyl ether/CH₃CN. The precipitate was filtered off and dried, yielding 2.3 g of a compound 135 having a molecular weight of 615.5 g and being represented by the formula

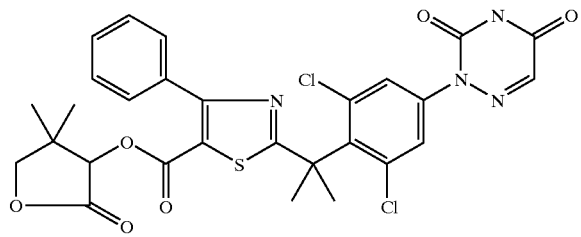

EXAMPLE B137

Sodium hydroxide 1M (0.000328 mole) was added to compound 135 (0.000164 mole) in THF (4 ml) and the reaction mixture was stirred overnight at room temperature. The resulting product was purified by high performance liquid chromatography over Hyperprep RP-C18 BDS (eluent: 0.5% ammonium acetate aqueous solution/CH₃CN 90/10/ CH₃CN 90/10). The product fractions were collected and the organic solvent was evaporated. The aqueous concentrate was desalted on column and eluted with CH₃CN. The product fractions were collected and the solvent was evaporated at room temperature, yielding 0.045 g (41%) of a compound 136 having a molecular weight of 677.5 g and being represented by the formula

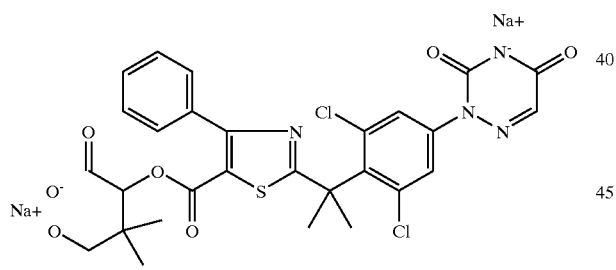

EXAMPLE B138

Bromine (two drops) was added at room temperature to a solution of α,α-dimethyl-γ-oxo-Benzenebutanoic acid (0.01 mole) in methylene chloride (10 ml) and acetic acid (2 ml). A hydrogen bromide/acetic acid mixture (1 drop) was added. Bromine (0.0105 mole) was further added at room temperature to the mixture, which was stirred at room temperature for one hour. Nitrogen was bubbled through the mixture for one hour. The solvent was evaporated under reduced pressure. The residue was co-evaporated with toluene, yielding 2.7 g (95%) of a compound 137 having a molecular weight of 285.1 g and being represented by the formula

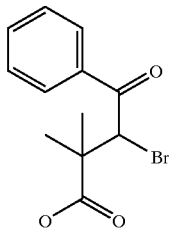

EXAMPLE B139

A mixture of intermediate (8) (0.05 mole) and compound 137 (0.05 mole) in ethanol (150 ml) and DMF (50 ml) was stirred for 72 hours at 70° C., yielding a fraction which was poured out into water and then separated into its layers. The aqueous layer was extracted with EtOAc. The combined organic layer was washed with water, dried, filtered and the solvent was evaporated under reduced pressure. The residue was crystallized from CH₃CN. The precipitate was filtered off and dried, giving a product which was crystallized again from CH₃CN. The precipitate was filtered off and dried, yielding 8.73 g of a compound 138 having a molecular weight of 545.5 g and being represented by the formula

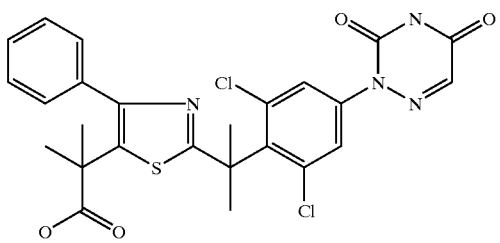

EXAMPLE B140

1,1'-carbonylbis-1H-imidazole (0.0042 mole) was added to a solution of intermediate (13) (0.0034 mole) in DMF (10 ml). The mixture was stirred at 40° C. for one hour. 1,3-dihydroxy cyclohexane (0.02 mole) then 1,8-diazabicyclo (5.4.0) undecene-7 (0.0034 mole) were added. The mixture was stirred at 40° C. for six hours, poured out into ice water and acidified with HCl 3N. The precipitate was filtered, washed with water, dried, taken up in methylene chloride and washed with water. The organic layer was separated, dried (MgSO₄), filtered and the solvent was evaporated. The residue was purified by column chromatography over silica gel (eluent: CH₂Cl₂/CH₃OH 98/2;15–40 μm). The pure fractions were collected and the solvent was evaporated, yielding 0.14 g (2.5%) of the cis-isomer of a compound 139 having a molecular weight of 1086.9 g and a melting point of 180° C. and being represented by the formula

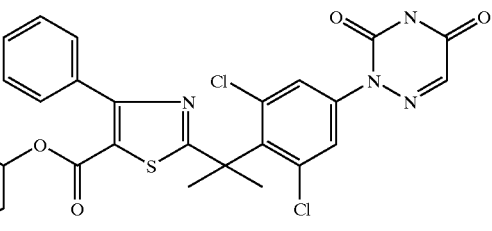

and 1.4 g of a fraction which was then crystallized from 2-propanone/diethyl ether. The precipitate was filtered off and dried, yielding 1 g (49%) of a compound 140 having a molecular weight of 601.5 g and a melting point of 175° C. and being represented by the formula

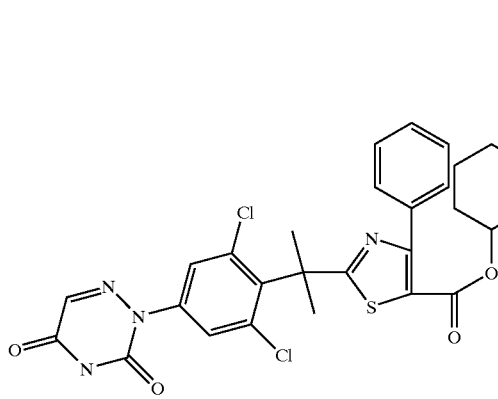

EXAMPLE B141

A mixture of intermediate (13) (0.0037 mole), α-cyclopentyl-, 1-chloroethyl ester Benzeneacetic acid (0.00733 mole), sodium hydrocarbonate (0.0037 mole) and potassium iodide (0.0037 mole) in DMF (10 ml) was stirred at 70° C. for 2 days, brought to room temperature. HCl 1N was added. The precipitate was taken up in EtOAc and washed with water. The organic layer was separated, dried (MgSO$_4$), filtered, and the solvent was evaporated. The residue was purified by column chromatography over silica gel (eluent: CH$_2$Cl$_2$/CH$_3$OH; 99/1;15–40 μm). The pure fractions were collected and the solvent was evaporated. The residue was purified by high-performance liquid chromatography over Kromacil C-18 (eluent: 5% ammonium acetate aqueous solution/CH$_3$CN 20/80). The pure fractions were collected and the solvent was evaporated, yielding 0.69 g (25%) of a compound 141 having a molecular weight of 733.7 g and a melting point of 110° C. and being represented by the formula

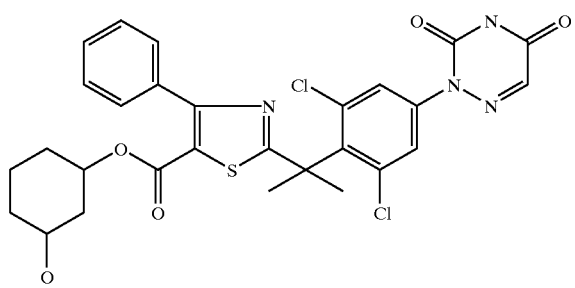

EXAMPLE B142

A mixture of N,N,N-trimethyl-(tribromide) Benzenaminium (0.005 mole) in THF (25 ml) was stirred at room temperature. Phenyl trimethylammonium bromide (0.005 mole) was added portionwise at room temperature for one hour. Water was added, then the mixture was extracted with methylene chloride. The organic layer was separated, dried, filtered and the solvent was evaporated, yielding 1.55 g (100%) of a compound 142 having a molecular weight of 313.1 g and being represented by the formula

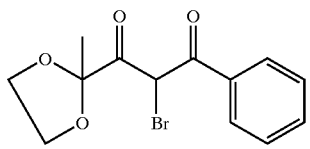

EXAMPLE B143

A mixture of intermediate (8) (0.0045 mole) and compound 142 (0.005 mole) in ethanol (20 ml) and DMF (10 ml) was stirred at 60° C. for two hours. The solvent was evaporated. The residue was purified by flash column chromatography over silica gel (eluent: CH$_2$Cl$_2$/CH$_3$OH 99.7/0.3). The pure fractions were collected and the solvent was evaporated, giving a fraction which was stirred in ethanol (10 ml). The resulting precipitate was filtered off, washed with DIPE and dried, yielding 0.4 g of a compound 143 having a molecular weight of 573.5 g and being represented by the formula

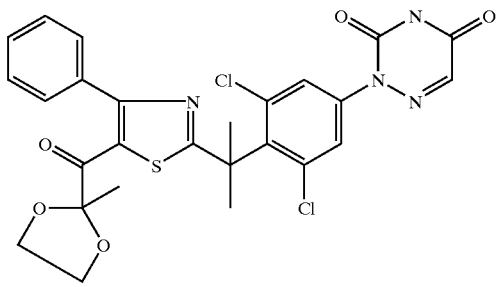

EXAMPLE B144

A mixture of compound 143 (0.0094 mole) in methanol (50 ml) was stirred at room temperature. Sodium borohydride (0.01 mole) was added portionwise over 30 minutes. The mixture was stirred for 90 minutes. More sodium borohydride (0.014 mole) was added portionwise over 30 minutes and the resulting mixture was further stirred for 90 minutes. The resulting precipitate was filtered off, washed with methanol and DIPE and dried, yielding 4.5 g of a compound 144 having a molecular weight of 575.5 g and being represented by the formula

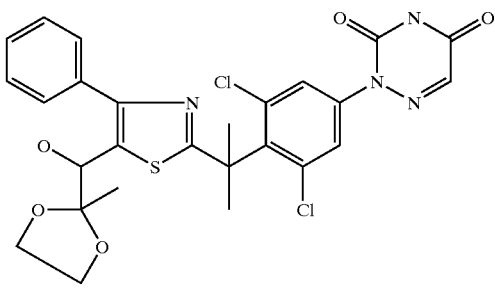

EXAMPLE B145 a) A solution of β-oxo-3-hydroxypropyl benzenepropanoic acid ester (0.097 mol; 26.0 g with 83% purity) in chloroform (250 ml) was stirred vigorously at room temperature under nitrogen atmosphere. N-bromosuccinimide (0.1 mol) was added portionwise over 2 hours. The reaction mixture was stirred for one hour at room temperature. More N-bromosuccinimide (2.5 g) was added and the reaction mixture was stirred for 1.5 hours at room temperature. An aqueous $NaHCO_3$ solution (16.8 g $NaHCO_3$ in 200 ml of water) was added and stirring was continued for 5 minutes. The layers were separated. The organic layer was dried, filtered and the solvent evaporated, then co-evaporated with toluene, yielding 35.9 g of

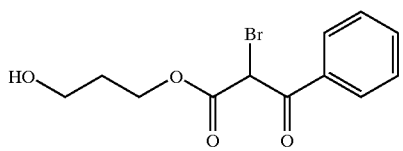

(intermediate 28)

b) A mixture of intermediate (8) (0.00457 mol), intermediate (28) (0.00503 mol) and DMF (0.00457 mol) in 1,3-propanediol (10 ml) was stirred at 70° C. for 6 hours, then cooled and poured out into ice water. The precipitate was filtered, washed with HCl diluted/$H_2O$ and dried. The residue was taken up in $CH_2Cl_2$. The organic layer was separated, washed with $H_2O$, dried, filtered and the solvent was evaporated. The residue was purified by column chromatography over silica gel (eluent: $CH_2Cl_2/CH_3OH$ 97.5/2.5; 15–40 μm). The pure fractions were collected and the solvent was evaporated. The residue was crystallized from DIPE. The precipitate was filtered off and dried, yielding 0.55 g of 3-hydroxypropyl 2-[1-[2,6-dichloro-4-(4,5-dihydro-3,5-dioxo-1,2,4-triazin-2(3H)-yl)phenyl]-1-methylethyl]-4-phenyl-5-thiazolecarboxylate (compound 145).

EXAMPLE B146 a) A mixture of intermediate (8) (0.0119 mol), (±)-1,1-dimethylethyl α-bromo-beta-oxo-benzenepropanoate (0.0137 mol) and $K_2CO_3$ (0.0357 mol) in acetonitrile (55 ml) was stirred at room temperature for 3.5 hours. Ice and ethyl acetate were added. The mixture was acidified with HCl 3N. The organic layer was separated, dried, filtered and the solvent was evaporated. The product was used without further purification, yielding 8 g of

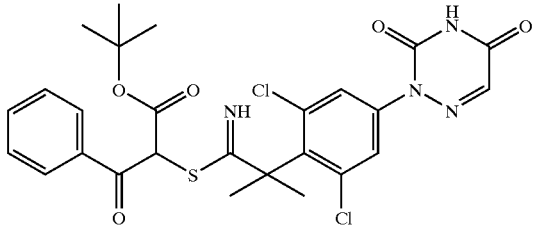

(intermediate 29).

b) Intermediate (29) (0.0119 mol) and tert-butanol (24 g) were stirred and refluxed for 2 hours. The mixture was brought to room temperature. The solvent was evaporated. The residue was taken up in dichloromethane. The organic solution was washed with water, dried, filtered and the solvent was evaporated. The residue was purified by column chromatography over silica gel (eluent: $CH_2Cl_2/CH_3OH$ 99/1). The pure fractions were collected and the solvent was evaporated, yielding 0.45 g of,

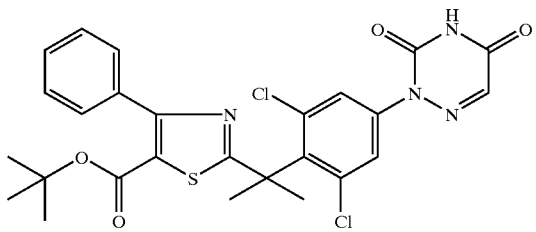

(intermediate 30, mp. 130° C.).

c) A mixture of intermediate (30) (0.0518 mol) in trifluoroacetic acid (200 ml) was stirred at room temperature for 4 hours and poured out on ice. The precipitate was filtered, washed with water and dried. The residue was taken up in dichloromethane. The organic layer was separated, washed with water, dried, filtered and the solvent was evaporated. The residue was purified by column chromatography over silica gel (eluent: $CH_2Cl_2/CH_3OH$/acetic acid; 97/3/0.1). The pure fractions were collected and the solvent was evaporated. The residue was crystallized from acetonitrile. The precipitate was filtered off and dried, yielding 27.1 g of

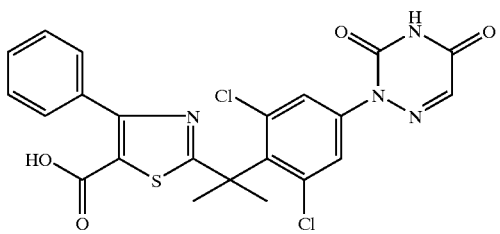

(intermediate 31, mp. >250° C.).

d) A solution of 1-chlorosulfonylpyrrolidine (0.0088 mol) in dichloromethane (5 ml) was added dropwise at room temperature to a mixture of 1,1-dimethylethyl 1-piperazinecarboxylate (0.0088 mol) and triethylamine (0.0177 mol) in dichloromethane (15 ml). The mixture was stirred at room temperature for 12 hours and HCl 0.5N was added. The mixture was separated and extracted with dichloromethane. The dichloromethane layer were brought together, dried, filtered and the solvent was evaporated, yielding 2.8 g of

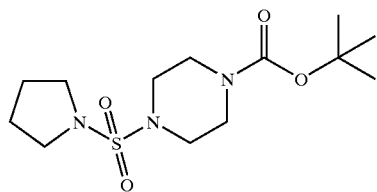

(intermediate 32).

e) A mixture of intermediate (32) (0.088 mol) and a mixture of HCl (5N) in isopropanol (0.0263 mol) in isopropanol (30 ml) was stirred and refluxed for 5 hours, evaporated, taken up in DIPE, filtered and dried, yielding 2 g of

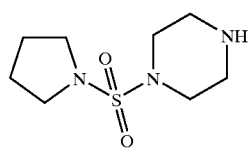

Hydrochloride (1:1)

(intermediate 33).

f) A mixture of intermediate (33) (0.0078 mol), 1-bromo-2-ethanol (0.0313 mol) and $Na_2CO_3$ (0.047 mol) in ethanol (45 ml) was stirred at 80° C. for 18 hours, brought to room temperature and water was added. The mixture was extracted twice with dichloromethane. The organic layer was separated, dried, filtered and the solvent was evaporated, yielding 2 g of

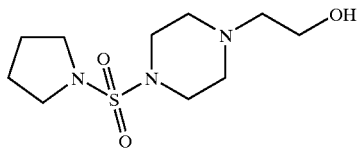

(intermediate 34).

g) Intermediate (31) (0.003 mol) and 1,1'-carbonylbis-1H-imidazole (CDI) (0.0037 mol) were stirred at 40° C. for 1 hour and a solution of intermediate (34) (0.0051 mol) and 1,8-diaza-7-bicyclo[5.4.0]undecene (DBU) (0.003 mol) in DMF (15 ml) was added. The mixture was stirred at 40° C. for 6 hours, brought to room temperature, poured out into ice water, acidified with HCl 3N and filtered. The precipitate was washed with water, taken up in dichloromethane and washed with water. The organic layer was separated, dried, filtered and dried. The residue was purified by column chromatography over silica gel (eluent: $CH_2Cl_2/CH_3OH$ 98/2), yielding 0.775 g of,

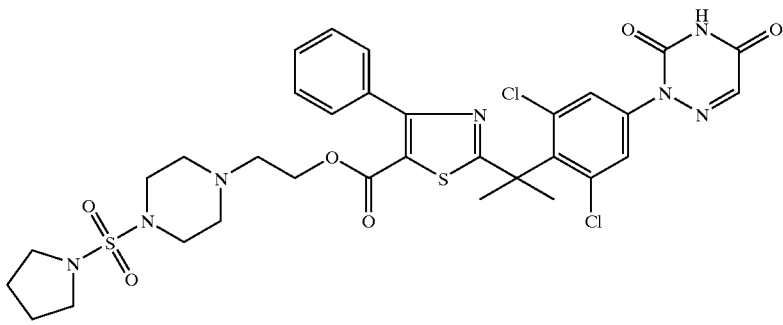

(compound 146, mp. 196° C.).

EXAMPLE B147 a) Bromine (2 drops) was added at room temperature to a solution of 3-benzoyl-2,2-dimethyl-propionic acid (0.01 mol) in dichloromethane (10 ml) and acetic acid (2 ml). A mixture of HBr in acetic acid (1 drop) was added. Bromine (0.0105 mol) was added further at room temperature to the mixture. The mixture was stirred at room temperature for 1 hour. Nitrogen gas was bubbled through the mixture for 1 hour. The solvent was evaporated under reduced pressure. The residue was co-evaporated with toluene, yielding 2.7 g of

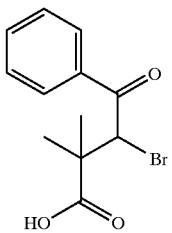

(intermediate 35).
b) A mixture of intermediate (8) (0.05 mol) and intermediate (35) (0.05 mol) in ethanol (150 ml) and DMF (50 ml) was stirred for 72 hours at 70° C. The reaction product was poured out into water and then separated into its layers. The aqueous layer was extracted with ethyl acetate. The combined organic layer was washed with water, dried, filtered and the solvent was evaporated under reduced pressure. The residue was crystallized from acetonitrile. The precipitate was filtered off and dried, yielding

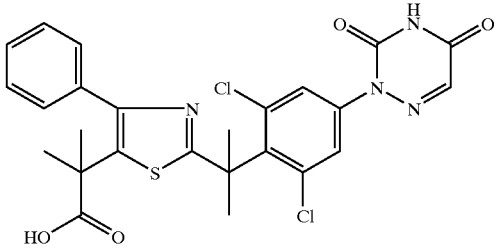

(intermediate 36).
c) A mixture of intermediate (36) (0.00275 mol) and 1,1'-carbonylbis-1H-imidazole (0.00416 mol) in dichloromethane (30 ml) was stirred at room temperature for 2 hours. Butyric acid (0.00416 mol) was added at room temperature. The mixture was stirred at room temperature overnight. The solvent was evaporated under reduced pressure. The residue was purified by column chromatography over silica gel (eluent: $CH_2Cl_2$/THF 100/0 to 80/20). The pure fractions were collected and the solvent was evaporated. The residue was stirred in ethyl acetate/hexane 30/70). The precipitate was filtered off and dried, yielding 0.8 g of

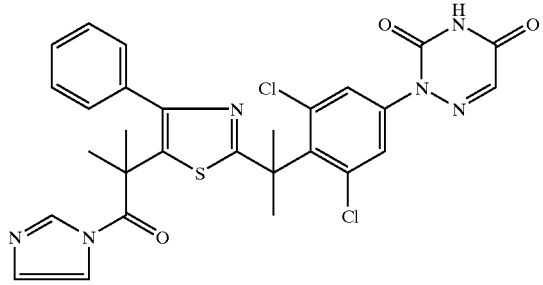

(intermediate 37).
d) Intermediate (37) (0.00173 mol) and dihydro-3-hydroxy-4,4-dimethyl-2(3H)-furanone (0.04 mol) were stirred at 100° C. for 2.5 hours. The mixture was poured out into water and then extracted with ethyl acetate. The organic layer was separated, dried, filtered and the solvent was evaporated. The residue was purified over silica gel on a glass filter (eluent: $CH_2Cl_2$/THF 100/0 to 98/2). The pure fractions were collected and the solvent was evaporated. The residue was stirred in ethyl acetate/hexane (1/1). The precipitate was filtered off and dried at 50° C. overnight, yielding 0.38 g of

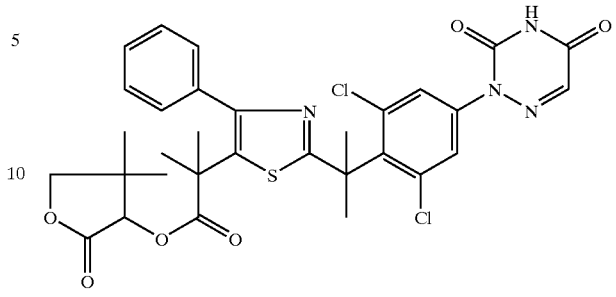

(compound 147).

What is claimed is:
1. A compound having the formula:

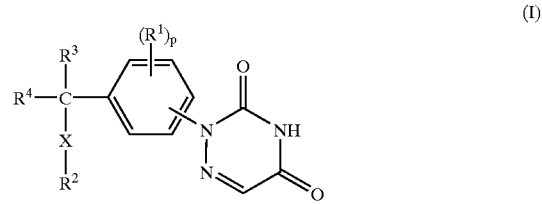

(I)

the N-oxide, the pharmaceutically acceptable addition salt and the stereochemically isomeric form thereof, wherein:
p represents an integer being 0, 1, 2, 3 or 4;
X represents O, S, $NR^5$ or a direct bond or —X—$R^2$ taken together may represent cyano;
Y represents O, S, $NR^5$, or $S(O)_2$;
each $R^1$ independently represents C(=O)·Z—$R^{14}$, $C_{1-6}$alkyl, halo, polyhalo$C_{1-6}$alkyl, hydroxy, mercapto, $C_{1-6}$alkyloxy, $C_{1-6}$alkylthio, $C_{1-6}$alkylcarbonyloxy, aryl, cyano, nitro, $Het^3$, $R^6$, $NR^7R^8$ or $C_{1-4}$alkyl substituted with C(=O)—Z—$R^{14}$, $Het^3$, $R^6$ or $NR^7R^8$;
$R^2$ represents $Het^1$, $C_{3-7}$cycloalkyl optionally substituted with C(=O)—Z—$R^{14}$, $C_{1-6}$alkyl or $C_{1-6}$alkyl substituted with one or two substituents selected from the group consisting of: C(=O)·Z—$R^{14}$, hydroxy, mercapto, cyano, amino, mono- or di($C_{1-4}$alkyl)amino, $C_{1-6}$alkyloxy optionally substituted with C(=O)—Z—$R^{14}$, $C_{1-6}$alkylthio optionally substituted with C(=O)—Z—$R^{14}$, $C_{1-6}$alkylsulfonyloxy, $C_{3-7}$cyoloalkyl optionally substituted with C(=O)—Z—$R^{14}$, aryl, aryloxy, arylthio, $Het^1$, $Het^1$oxy and $Het^1$thio; and if X is O, S or $NR^5$, then $R^2$ may also represent aminothiocarbonyl, $C_{1-4}$alkylcarbonyl optionally substituted with C(=O)—Z—$R^{14}$, $C_{1-4}$alkylthiocarbonyl optionally substituted with C(=O)—Z—$R^{14}$, arylcarbonyl, arylthiocarbonyl, $Het^1$carbonyl or $Het^1$thiocarbonyl;
$R^3$ represents hydrogen, $C_{1-6}$alkyl or $C_{3-7}$cycloalkyl;
$R^4$ represents hydrogen, $C_{1-6}$alkyl or $C_{3-7}$cycloalkyl; or
$R^3$ and $R^4$ taken together form a $C_{2-6}$alkanediyl;
$R^5$ represents hydrogen or $C_{1-4}$alkyl;
each $R^6$ independently represents $C_{1-6}$alkylsulfonyl, aminosulfonyl, piperidinylsulfonyl, mono- or di($C_{1-4}$alkyl)aminosulfonyl, mono- or di(benzyl)aminosulfonyl, polyhalo$C_{1-6}$alkylsulfonyl, $C_{1-6}$alkylsulfinyl, phenyl$C_{1-4}$alkylsulfonyl, piperazinylsulfonyl, aminopiperidinylsulfonyl, piperidinylaminosulfonyl, N—C$_{1-4}$alkyl-N-piperidinylaminosulfonyl, Y—R$^{14}$, mono- or di-(C$_{1-4}$alkyl)aminoC$_{1-4}$alkylsulfonyl, Het$^6$sulfonyl or C$_{3-7}$cycloalkylsulfonyl;

each R$^7$ and each R$^8$ are independently selected from the group consisting of: hydrogen, C$_{1-4}$alkyl, hydroxyC$_{1-4}$alkyl, mercapto-C$_{1-4}$alkyl, dihydroxyC$_{1-4}$alkyl, aryl, arylC$_{1-4}$alkyl, C$_{1-4}$alkyloxyC$_{1-4}$alkyl, C$_{1-4}$alkylcarbonyl, C$_{1-4}$alkyl-thiocarbonyl, arylcarbonyl, aryithiocarbonyl, Het$^3$thiocarbonyl, Het$^3$carbonyl, mono- or di(C$_{1-4}$alkyl)aminoC$_{1-4}$alkyl, arylaminocarbonyl, arylaminothiocarbonyl, Het$^3$aminocarbonyl, Het$^3$aminothiocarbonyl, C$_{3-7}$cycloalkyl, pyridinylC$_{1-4}$alkyl, C$_{1-4}$alkanediyl-C(=O)—Z—R$^{14}$, —C(=O)—Z—R$^{14}$, —Y—C$_{1-4}$alkanediyl-C(=O)—Z—R$^{14}$, Het$^3$, Het$^4$ and R$^6$; or R$^7$ and R$^8$ taken together with the nitrogen atom to which they are attached form a radical of formula

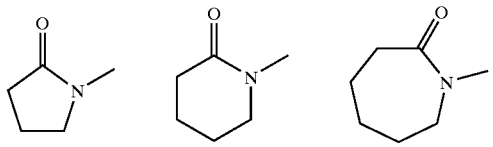

R$^9$ and R$^{10}$ are each independently selected from the group consisting of: hydrogen, C$_{1-4}$alkyl, hydroxyC$_{1-4}$alkyl, mercapto-C$_{1-4}$alkyl, dihydroxyC$_{1-4}$alkyl, phenyl, phenylC$_{1-4}$alkyl, C$_{1-4}$alkyloxyC$_{1-4}$alkyl, C$_{1-4}$alkylcarbonyl, arylcarbonyl, Het$^3$carbonyl, Het$^3$thiocarbonyl, mono- or di(C$_{1-4}$alkyl)aminoC$_{1-4}$alkyl, arylaminocarbonyl, arylaminothiocarbonyl, Het$^3$aminocarbonyl, Het$^3$aminothiocarbonyl, C$_{3-7}$cycloalkyl, pyridinylC$_{1-4}$alkyl, C$_{1-4}$alkanediyl-C(=O)—Z—R$^{14}$, —C(=O)—Z—R$^{14}$, —Y—C$_{1-4}$alkanediyl-C(=O)—Z—R$^{14}$, Het$^3$, Het$^4$ and R$^6$; or R$^9$ and R$^{10}$ taken together with the nitrogen atom to which they are attached form a radical of formula

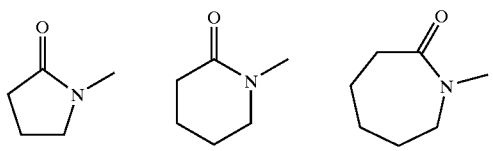

each R$^{11}$ independently being selected from the group consisting of: hydroxy, mercapto, cyano, nitro, halo, trihalomethyl, C$_{1-4}$alkyloxy optionally substituted with C(=O)—Z—R$^{14}$, C$_{1-6}$alkylthio optionally substituted with C(=O)—Z—R$^{14}$, formyl, trihaloC$_{1-4}$alkylsulfonyloxy, R$^6$, NR$^7$R$^8$, C(=O)NR$^{15}$R$^{16}$, —C(=O)—Z—R$^{14}$, —Y—C$_{1-4}$alkanediyl-C(=O)—Z—R$^{14}$, aryl, aryloxy, arylcarbonyl, arylthiocarbonyl, C$_{3-7}$cycloalkyl optionally substituted with C(=O)—Z—R$^{14}$, C$_{3-7}$cycloalkyloxy optionally substituted with C(=O)—Z—R$^{14}$, C$_{3-7}$cycloalkylthio optionally substituted with C(=O)—Z—R$^{14}$, phthalimide-2-yl, Het$^3$, Het$^4$, C(=O)Het$^3$, C(=O)C$_{1-4}$alkyl optionally be substituted with one or more substituents independently selected from hydroxy, mercapto, halo and phenyl;

R$^{12}$ and R$^{13}$ are each independently selected from the group consisting of:

hydrogen, C$_{1-4}$alkyl, hydroxyC$_{1-4}$alkyl, mercapto-C$_{1-4}$alkyl, dihydroxyC$_{1-4}$alkyl, phenyl, phenyl-C$_{1-4}$alkyl, C$_{1-4}$alkyloxyC$_{1-4}$alkyl, C$_{1-4}$alkylcarbonyl, C$_{1-4}$alkylthiocarbonyl, arylcarbonyl, mono- or di(C$_{1-4}$alkyl)aminoC$_{1-4}$alkyl, arylaminocarbonyl, arylaminothiocarbonyl, C$_{3-7}$cycloalkyl, pyridinylC$_{1-4}$alkyl, C$_{1-4}$alkanediyl-C(=O)—Z—R$^{14}$, —C(=O)—Z—R$^{14}$, —Y—C$_{1-4}$alkanediyl-C(=O)—Z—R$^{14}$ and R$^6$;

or R$^{12}$ and R$^{13}$ taken together with the nitrogen atom to which they are attached form a radical of formula

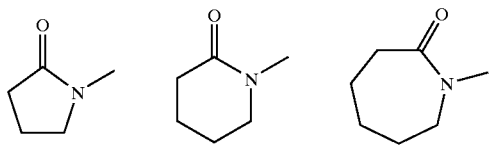

each R$^{14}$ independently represents hydrogen; C$_{1-20}$acyl or C$_{1-20}$alkylC$_{1-20}$acyl (having a straight or branched, saturated or unsaturated hydrocarbon chain having 1 to 20 carbon atoms) optionally substituted with one or more substituents selected from the group consisting of: hydroxy, mercapto, hydroxyC$_{1-4}$alkyl, mercaptoC$_{1-4}$alkyl, NR$^{17}$R$^{18}$, aryl, mono- or di-(C$_{1-4}$alkyl)amino, cyano and Het$^5$; C$_{1-20}$alkyl optionally substituted with one or more substituents selected from the group consisting of: hydroxy, halo, mercapto, C$_{1-4}$alkyloxyC$_{1-4}$ alkyloxy, mercaptoC$_{1-4}$alkyl, NR$^{17}$R$^{18}$, aryl, mono- or di-(C$_{1-4}$alkyl)amino, cyano, Het$^5$, C$_{1-4}$alkyloxycarbonyl, arylC$_{1-4}$alkyloxycarbonyl, arylC$_{1-4}$alkyloxy, arylC$_{1-4}$alkylthiocarbonyl, arylC$_{1-4}$ alkylthio, Het$^5$C$_{1-4}$alkyloxy, arylC$_{1-4}$alkylthio, C$_{3-7}$ cycloalkyl and Het$^5$C$_{1-4}$alkylthio; C$_{3-20}$alkenyl optionally substituted with phenyl; C$_{3-20}$alkynyl; C$_{3-7}$ cycloalkyl optionally substituted with one or more substituents selected from the group consisting of: hydroxy, mercapto, halo, mercaptoC$_{1-4}$alkyl and hydroxyC$_{1-4}$alkyl; Het$^5$ or phenyl or R$^{14}$ represents a radical having any of the following formulae:

(a)

(b)

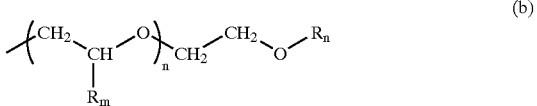

(c)

(d)

(e)

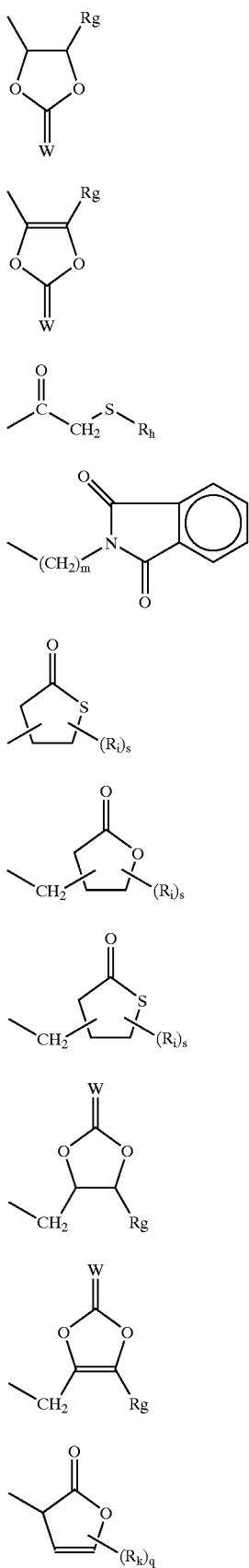

(h)

(i)

(j)

(k)

(l)

(m)

(n)

(o)

(p)

(q)

(r)

(s)

(t)

wherein m is 1 to 4, n is 0 to 5, q is 0 to 2, r is 0 to 2 and s is 0 to 4;

$R^b$ is selected from the group consisting of: hydrogen, $C_{1-6}$alkyl, phenyl, $C_{3-7}$cycloalkyl, $C_{1-4}$ alkyloxy$C_{1-6}$ alkyl and $C_{1-4}$ alkyl-Y—$C_{1-4}$alkyl;

$R^a$, $R^c$, $R^d$, $R^e$ and $R^f$ are each independently selected from the group consisting of: hydrogen, $C_{1-6}$alkyl, phenyl and $C_{3-7}$cycloalkyl, or $R^e$ and $R^f$ taken together may form —$CH_2$—$CH_2$—, —$CH_2CH_2$—$CH_2$— or —$CH_2$—$CH_2$—$CH_2$—$CH_2$—;

$R_g$, $R_h$ and $R_k$ are each independently hydrogen or $C_{1-4}$ alkyl;

$R_l$ is selected from the group consisting of: hydroxy, $C_{3-7}$cycloalkyl and $C_{1-4}$alkyl, or two $R_l$ taken together may form —$CH_2$—$CH_2$, —$CH_2$—$CH_2$—$CH_2$— or —$CH_2$—$CH_2$—$CH_2$—$CH_2$— (thus building a spiro radical);

$R_j$ is selected from the group consisting of: —O—$R_b$; $C_{1-6}$alkyl optionally substituted with phenyl or $C_{3-7}$cycloalkyl; phenyl; $C_{3-7}$cycloalkyl optionally substituted with $C_{1-4}$ alkyloxy and mono- or di($C_{1-4}$alkyl) amino;

$R_m$ is hydrogen or $C_{1-4}$ alkyloxy;

$R_n$ is hydrogen, $C_{1-4}$alkyl, $C_{3-7}$cycloalkyl, phenyl or phenyl$C_{1-4}$alkyl; and W represents O or S;

each Z independently represents O, S, NH, —$CH_2$O— or —$CH_2$S— whereby —$CH_2$— is attached to the carbonyl group; or —Z—$R^{14}$ taken together form a radical of formula (f)

(g)

$R^{15}$ and $R^{16}$ are each independently selected from the group consisting of: hydrogen; $C_{1-4}$alkyl optionally substituted with one or more substituents independently selected from hydroxy, mercapto, aryl, mono- or di($C_{1-4}$alkyl) amino and pyridinyl; $C_{1-4}$alkyloxy; aryl; —C(=O)—Z—$R^{14}$; arylcarbonyl; arylthiocarbonyl; arylaminocarbonyl, arylaminothiocarbonyl; aminocarbonylmethylene; mono- or di($C_{1-4}$alkyl) aminocarbonylmethylene; Het$^3$aminocarbonyl; Het$^3$aminothiocarbonyl pyridinyl$C_{1-4}$alkyl; Het$^3$ and $R^6$; or $R^{15}$ and $R^{16}$ taken together with the nitrogen atom to which they are attached form a radical of formula

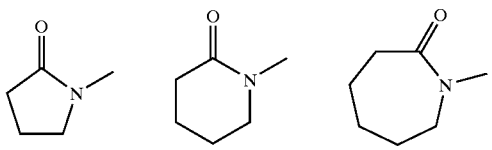

$R^{17}$ and $R^{18}$ are each independently selected from the group consisting of: hydrogen, $C_{1-6}$alkyl optionally substituted with one or more substituents independently selected from hydroxy, mercapto, aryl, mono- or di($C_{1-4}$alkyl) amino, $C_{1-4}$ alkyloxy and pyridinyl; $C_{1-4}$alkyloxycarbonyl; aryl; $C_{1-4}$alkylcarbonyl; $C_{1-4}$alkylthiocarbonyl; arylcarbonyl; arylthiocarbonyl; arylaminocarbonyl; arylaminothiocarbonyl; $C_{3-7}$cycloalkyl; $C_{1-4}$alkane-diyl-C(=O)—Z—$C_{1-6}$ alkyl; —C(=O)—Z—$C_{1-6}$alkyl; —Y—$C_{1-4}$ alkanediyl-C(=O)—Z—$C_{1-6}$alkyl and $R^6$;

aryl represents phenyl optionally substituted with one, two or three substituents each independently selected from the group consisting of: nitro, azido, cyano, halo, hydroxy, mercapto, $C_{1-4}$alkyl, $C_{3-7}$cycloalkyl, $C_{1-4}$alkyloxy, $C_{1-4}$alkylthio, formyl, polyhalo$C_{1-4}$alkyl, $NR^9R^{10}$, C(=O)$NR^9R^{10}$, C(=O)—Z—$R^{14}$, $R^6$, —O—$R^6$, phenyl, $Het^3$, C(=O)$Het^3$ and $C_{1-4}$alkyl substituted with one or more substituents each independently selected from the group consisting of: halo, hydroxy, mercapto, $C_{1-4}$alkyloxy, $C_{1-4}$alkylthio, C(=O)—Z—$R^{14}$, —Y—$C_{1-4}$alkanediyl-C(=O)—Z—$R^{14}$, $Het^3$ or $NR^9R^{10}$;

$Het^1$ represents a three-membered, four-membered, five-membered or six-membered aromatic or non-aromatic, monocyclic or polycyclic heterocycle comprising one or more heteroatoms or a fused polycyclic ring system including such heterocycle;

wherein said heterocycle may optionally be substituted with one, or where possible, two or three substituents each independently selected from the group consist of: $Het^2$, $R^{11}$ and $C_{1-4}$alkyl optionally substituted with one or, where possible, two or three substituents each independently selected from $Het^2$ or $R^{11}$;

$Het^2$ represents a three-membered, four-membered, five-membered or six-membered aromatic or non-aromatic, monocyclic or polycyclic heterocycle comprising one or more heteroatoms, or a fused polycyclic ring system including such heterocycle;

wherein said heterocycle may optionally be substituted with one, or where possible, two or three substituents each independently selected from the group consist of: $Het^4$, $R^{11}$ and $C_{1-4}$alkyl optionally substituted with one or, where possible, two or three substituents each independently selected from $Het^4$ or $R^{11}$;

$Het^3$ represents a three-membered, four-membered, five-membered or six-membered aromatic or non-aromatic monocyclic heterocycle comprising one or more heteroatoms, wherein said monocyclic heterocycle may optionally be substituted with, where possible, one, two, three or four substituents each independently selected from the group consist of: hydroxy, $C_{1-4}$alkyl, $C_{1-4}$alkyloxy, $C_{1-4}$alkylcarbonyl, piperidinyl, $NR^{12}R^{13}$, C(=O)—Z—$R^{14}$, $R^6$ and $C_{1-4}$alkyl substituted with one or two substituents independently selected from the group consist of: hydroxy, carbonyl $C_{1-4}$alkyloxy, phenyl, C(=O)—Z—$R^{14}$, —Y—$C_{1-4}$alkanediyl-C(=O)—Z—$R^{14}$, $R^6$ and $NR^{12}R^{13}$;

$Het^4$ represents a three-membered, four-membered, five-membered or six-membered aromatic or non-aromatic monocyclic heterocycle comprising one or more heteroatoms $Het^5$ represents a three-membered, four-membered, five-membered or six-membered aromatic or non-aromatic, monocyclic or polycyclic heterocycle comprising one or more heteroatoms, or a fused polycyclic ring system including such heterocycle;

wherein said heterocycle each independently may be substituted with, where possible, one, two, three or four substituents each independently selected from the group consisting of: hydroxy, mercapto, carbonyl, $C_{1-4}$alkyl, $C_{1-4}$alkyloxy, $C_{1-4}$alkylthio, $C_{1-4}$alkylcarbonyl, piperidinyl, $NR^{17}R^{18}$, C(=O)—Z—$C_{1-6}$alkyl, $R^6$, sulfonamido and $C_{1-4}$alkyl substituted with one or two substituents independently selected from hydroxy, $C_{1-4}$alkyloxy, mercapto, $C_{1-4}$alkylthio, phenyl, C(=O)—Z—$C_{1-6}$alkyl, —Y—$C_{1-4}$alkanediyl-C(=O)—Z—$C_{1-6}$alkyl, $R^6$ and $NR^{17}R^{18}$;

$Het^6$ represents a three-membered, four-membered five-membered or six-membered aromatic or non-aromatic monocyclic heterocycle comprising one or more heteroatoms, wherein said heterocycle may optionally be substituted with one, or where possible, two or three substituents each independently selected from $Het^2$, $R^{11}$ or $C_{1-4}$alkyl optionally substituted with one or more substituents independently selected from $Het^2$ and $R^{11}$;

provided however that $R^2$ is other than $C_{1-6}$ alkyloxycarbonyl$C_{1-6}$alkyl or aminocarbonyl; and $R^7$, $R^8$, $R^9$ and $R^{10}$ are other than aminocarbonyl, $C_{1-4}$alkylcarbonyloxy-$C_{1-4}$alkylcarbonyl, hydroxy$C_{1-4}$alkylcarbonyl, $C_{1-4}$alkyloxycarbonylcarbonyl, C(=O)—O—$R^{19}$, $C_{1-4}$alkanediylC(=O)—O—$R^{19}$ or —Y—$C_{1-4}$alkanediylC(=O)—O—$R^{19}$; and $R^{12}$ and $R^{13}$ are other than $C_{1-4}$alkylcarbonyloxy-$C_{1-4}$alkylcarbonyl, hydroxy$C_{1-4}$alkylcarbonyl or $C_{1-4}$alkylcarbonylcarbonyl; and $R^{11}$ is other than C(=O)—O—$R^{19}$, Y—$C_{1-4}$alkanediyl —C(=O)—$OR^{19}$, C(=O)$NH_2$, C(=O)$NHC_{1-4}$alkyl or C(=O)$NHC_{3-7}$cycloalkyl; and $R^{15}$ and $R^{16}$ are other than aminocarbonyl, $C_{1-4}$alkylcarbonyloxy-$C_{1-4}$alkylcarbonyl, hydroxy $C_{1-4}$alkylcarbonyl or $C_{1-4}$alkyloxycarbonylcarbonyl; and aryl is other than phenyl substituted with C(=O)—O—$R^{19}$, C(=O)$NH_2$, C(=O)$NHC_{1-4}$alkyl, C(=O)$NHC_{3-7}$cycloalkyl and/or with $C_{1-4}$alkyl substituted with C(=O)—O—$R^{19}$ or Y—$C_{1-4}$alkanediyl —C(=O)—O—$R^{14}$; and $Het^3$ is other than a monocyclic heterocycle substituted with C(=O)·O—$R^{19}$ and/or with $C_{1-4}$alkyl substituted with C(=O)—O—$R^{19}$ and/or Y—$C_{1-4}$alkanediyl C(=O)—O—$R^{19}$; and in each of the above proviso's $R^{19}$ is defined as hydrogen, $C_{1-4}$alkyl, $C_{3-7}$cycloalkyl, aminocarbonylmethylene or mono- or di($C_{1-4}$alkyl) aminocarbonylmethylene; and the compound of formula (I) contains at least one —C(=O)—Z—$R^{14}$ moiety.

2. A compound according to claim 1 having the formula

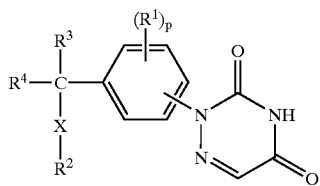

(I')

a N-oxide, a pharmaceutically acceptable addition salt or a stereochemically isomeric form thereof, wherein:

p represents an integer being 0, 1, 2, 3 or 4;

X represents O, S, $NR^5$ or a direct bond or $—X—R^2$ taken together may represent cyano;

Y represents O, S, $NR^5$, or $S(O)_2$;

each $R^1$ independently represents $C(=O)·Z—R^{14}$, $C_{1-6}$alkyl, halo, polyhalo$C_{1-6}$alkyl, hydroxy, mercapto, $C_{1-6}$alkyloxy, $C_{1-6}$alkylthio, $C_{1-6}$alkylcarbonyloxy, aryl, cyano, nitro, $Het^3$, $R^6$, $NR^7R^8$ or $C_{1-4}$alkyl substituted with $C(=O)·—Z—R^{14}$, $Het^3$, $R^6$ or $NR^7R^8$;

$R^2$ represents $Het^1$, $C_{3-7}$cycloalkyl optionally substituted with $C(=O)—Z—R^{14}$, $C_{1-6}$alkyl or $C_{1-6}$alkyl substituted with one or two substituents selected from the group consisting of: $C(=O)·Z—R^{14}$, hydroxy, cyano, amino, mono- or di($C_{1-4}$alkyl)amino, $C_{1-6}$alkyloxy optionally substituted with $C(=O)—Z—R^{14}$, $C_{1-6}$alkylsulfonyloxy, $C_{3-7}$cycloalkyl optionally substituted with $C(=O)—Z—R^{14}$, aryl, aryloxy, arylthio, $Het^1$, $Het^1$oxy and $Het^1$thio; and if X is O, S or $NR^5$, then $R^2$ may also represent aminothiocarbonyl, $C_{1-4}$alkylcarbonyl optionally substituted with $C(=O)—Z—R^{14}$, $C_{1-4}$alkylthiocarbonyl optionally substituted with $C(=O)—Z—R^{14}$, arylcarbonyl, arylthiocarbonyl, $Het^1$carbonyl or $Het^1$thiocarbonyl;

$R^3$ represents hydrogen, $C_{1-6}$alkyl or $C_{3-7}$cycloalkyl;

$R^4$ represents hydrogen, $C_{1-6}$alkyl or $C_{3-7}$cycloalkyl; or $R^3$ and $R^4$ taken together form a $C_{2-6}$alkanediyl;

$R^5$ represents hydrogen or $C_{1-4}$alkyl;

each $R^6$ independently represents $C_{1-6}$alkylsulfonyl, aminosulfonyl, mono- or di($C_{1-4}$alkyl)aminosulfonyl, mono- or di(benzyl)aminosulfonyl, polyhalo$C_{1-6}$alkylsulfonyl, $C_{1-6}$alkylsulfinyl, phenyl$C_{1-4}$alkylsulfonyl, piperazinylsulfonyl, aminopiperidinylsulfonyl, piperidinylaminosulfonyl, N—$C_{1-4}$alkyl-N-piperidinylaminosulfonyl or mono- or di($C_{1-4}$alkyl)amino$C_{1-4}$alkylsulfonyl;

each $R^7$ and each $R^8$ are independently selected from the group consisting of: hydrogen, $C_{1-4}$alkyl, hydroxy$C_{1-4}$alkyl, dihydroxy$C_{1-4}$alkyl, aryl, aryl$C_{1-4}$alkyl, $C_{1-4}$alkyloxy$C_{1-4}$alkyl, $C_{1-4}$alkylcarbonyl, arylcarbonyl, $Het^3$carbonyl, mono- or di($C_{1-4}$alkyl)amino$C_{1-4}$alkyl, arylaminocarbonyl, arylaminothiocarbonyl, $Het^3$aminocarbonyl, $Het^3$aminothiocarbonyl, $C_{3-7}$cycloalkyl, pyridinyl$C_{1-4}$alkyl, $C_{1-4}$alkanediyl-$C(=O)—Z—R^{14}$, $—C(=O)—Z—R^{14}$, $—Y—C_{1-4}$alkanediyl-$C(=O)—Z—R^{14}$, $Het^3$, $Het^4$ and $R^6$;

$R^9$ and $R^{10}$ are each independently selected from the group consisting of: hydrogen, $C_{1-4}$alkyl, hydroxy$C_{1-4}$alkyl, dihydroxy$C_{1-4}$alkyl, phenyl, phenyl$C_{1-4}$alkyl, $C_{1-4}$alkyloxy$C_{1-4}$alkyl, $C_{1-4}$alkylcarbonyl, phenylcarbonyl, $Het^3$carbonyl, mono- or di($C_{1-4}$alkyl)amino$C_{1-4}$alkyl, phenylaminocarbonyl, phenylaminothiocarbonyl, $Het^3$aminocarbonyl, $Het^3$aminothiocarbonyl, $C_{3-7}$cycloalkyl, pyridinyl$C_{1-4}$alkyl, $C_{1-4}$alkanediyl-$C(=O)—Z—R^{14}$, $—C(=O)—Z—R^{14}$, $—Y—C_{1-4}$alkanediyl-$C(=O)—Z—R^{14}$, $Het^3$, $Het^4$ and $R^6$;

each $R^{11}$ independently being selected from the group consisting of: hydroxy, mercapto, cyano, nitro, halo, trihalomethyl, $C_{1-4}$alkyloxy optionally substituted with $C(=O)—Z—R^{14}$, formyl, trihalo$C_{1-4}$alkylsulfonyloxy, $R^6$, $NR^7R^8$, $C(=O)NR^{15}R^{16}$, $—C(=O)—Z—R^{14}$, $—Y—C_{1-4}$alkanediyl-$C(=O)—Z—R^{14}$, aryl, aryloxy, arylcarbonyl, $C_{3-7}$cycloalkyl optionally substituted with $C(=O)—Z—R^{14}$, $C_{3-7}$cycloalkyloxy optionally substituted with $C(=O)—Z—R^{14}$, phthalimide-2-yl, $Het^3$, $Het^4$ and $C(=O)Het^3$;

$R^{12}$ and $R^{13}$ are each independently selected from the group consisting of: hydrogen, $C_{1-4}$alkyl, hydroxy$C_{1-4}$alkyl, dihydroxy$C_{1-4}$alkyl, phenyl, phenyl$C_{1-4}$alkyl, $C_{1-4}$alkyloxy$C_{1-4}$alkyl, $C_{1-4}$alkylcarbonyl, phenylcarbonyl, mono- or di($C_{1-4}$alkyl)amino$C_{1-4}$alkyl, phenylaminocarbonyl, phenylaminothiocarbonyl, $C_{3-7}$cycloalkyl, pyridinyl$C_{1-4}$alkyl, $C_{1-4}$ alkanediyl-$C(=O)—Z—R^{14}$, $—C(=O)—Z—R^{14}$, $—Y—C_{1-4}$alkanediyl-$C(=O)—Z—R^{14}$ and $R^6$;

each $R^{14}$ independently represents $C_{1-4}$ alkyl substituted with one or more substituents selected from the group consisting of: phenyl, di-$C_{1-4}$alkylamino, cyano, $Het^1$ and $C_{3-7}$ cycloalkyl, hydrogen, $C_{1-20}$acyl (having a straight or branched, saturated or unsaturated hydrocarbon chain having 1 to 20 carbon atoms), $C_{1-20}$alkyl, $C_{3-7}$cycloalkyl, polyhalo$C_{1-20}$alkyl or a radical of formula

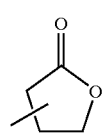

(a)

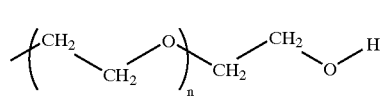

(b)

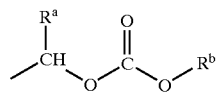

(c)

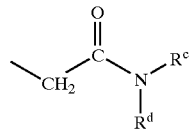

(d)

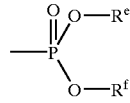

(e)

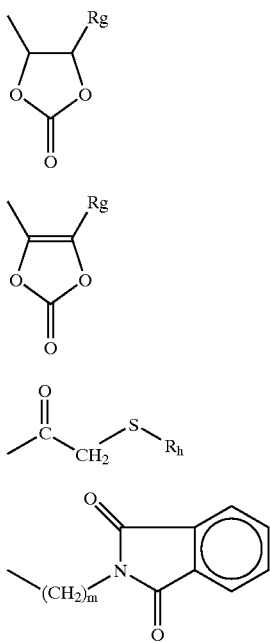

(h)

(i)

(j)

(k)

wherein n is 0 to 5 and m is 1 to 4;

$R^a$, $R^b$, $R^c$, $R^d$, $R^e$ and $R^f$ are each independently hydrogen, $C_{1-6}$alkyl or $C_{3-7}$cycloalkyl; or $R^e$ and $R^f$ taken together may form —$CH_2$—$CH_2$—, —$CH_2$—$CH_2$—$CH_2$— or —$CH_2$—$CH_2$—$CH_2$—$CH_2$—;

$R_g$ and $R_h$ are each independently $C_{1-4}$alkyl;

each Z independently represents O, S, NH, —$CH_2O$— or —$CH_2$—S— whereby —$CH_2$— is attached to the carbonyl group;

—Z—$R^{14}$ taken together form a radical of formula (f)

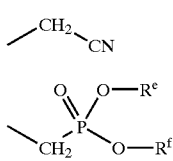

(g)

$R^{15}$ and $R^{16}$ are each independently selected from dihydroxy$C_{1-4}$alkyl, aryl, aryl$C_{1-4}$alkyl, $C_{1-4}$alkyloxy$C_{1-4}$alkyl, —C(=O)—Z—$R^{14}$, arylcarbonyl, mono- or di($C_{1-4}$alkyl)amino$C_{1-4}$alkyl, arylaminocarbonyl, arylaminothiocarbonyl, $Het^3$aminocarbonyl, $Het^3$aminothiocarbonyl, pyridinyl$C_{1-4}$alkyl, $Het^3$, $Het^4$ or $R^6$;

aminocarbonylmethylene or mono- or di($C_{1-4}$alkyl) aminocarbonylmethylene;

aryl represents phenyl optionally substituted with one, two or three substituents each independently selected from the group consisting of: nitro, azido, cyano, halo, hydroxy, $C_{1-4}$alkyl, $C_{3-7}$cycloalkyl, $C_{1-4}$alkyloxy, formyl, polyhalo$C_{1-4}$alkyl, $NR^9R^{10}$, C(=O)$NR^9R^{10}$, C(=O)—Z—$R^{14}$, $R^6$, —O—$R^6$, phenyl, $Het^3$, C(=O)$Het^3$ and $C_{1-4}$alkyl substituted with one or more substituents each independently selected from halo, hydroxy, $C_{1-4}$alkyloxy, C(=O)—Z—$R^{14}$, —Y—$C_{1-4}$alkanediyl-C(=O)—Z—$R^{14}$, $Het^3$ or $NR^9R^{10}$;

$Het^1$ represents heterocycle selected from the group consisting of: pyrrolyl, pyrrolinyl, imidazolyl, imidazolinyl, pyrazolyl, pyrazolinyl, triazolyl, tetrazolyl, furanyl, tetrahydrofuranyl, thienyl, thiolanyl, dioxolanyl, oxazolyl, oxazolinyl, isoxazolyl, thiazolyl, thiazolinyl, isothiazolyl, thiadiazolyl, oxadiazolyl, pyridinyl, pyrimidinyl, pyrazinyl, pyranyl, pyridazinyl, pyrrolidinyl, piperidinyl, piperazinyl, morpholinyl, thiomorpholinyl, dioxanyl, dithianyl, trithianyl, triazinyl, benzothienyl, isobenzothienyl, benzofuranyl, isobenzofuranyl, benzothiazolyl, benzoxazolyl, indolyl, isoindolyl, indolinyl, purinyl, 1H-pyrazolo[3,4-d]pyrimidinyl, benzimidazolyl, quinolyl, isoquinolyl, cinnolinyl, phtalazinyl, quinazolinyl, quinoxalinyl, thiazolopyridinyl, oxazolopyridinyl and imidazo[2,1-b]thiazolyl; wherein said heterocycle may optionally be substituted with one, or where possible, two or three substituents each independently selected from $Het^2$, $R^{11}$ or $C_{1-4}$alkyl optionally substituted with one or two substituents independently selected from $Het^2$ or $R^{11}$;

$Het^2$ represents a heterocycle selected from pyrrolyl, pyrrolinyl, imidazolyl, imidazolinyl, pyrazolyl, pyrazolinyl, triazolyl, tetrazolyl, furanyl, tetrahydrofuranyl, thienyl, thiolanyl, dioxolanyl, oxazolyl, oxazolinyl, isoxazolyl, thiazolyl, thiazolinyl, isothiazolyl, thiadiazolyl, oxadiazolyl, pyridinyl, pyrimidinyl, pyrazinyl, pyranyl, pyridazinyl, dioxanyl, dithianyl, trithianyl, triazinyl, benzothienyl, isobenzothienyl, benzofuranyl, isobenzofuranyl, benzothiazolyl, benzoxazolyl, indolyl, isoindolyl, indolinyl, purinyl, 1H-pyrazolo[3,4-d]pyrimidinyl, benzimidazolyl, quinolyl, isoquinolyl, cinnolinyl, phtalazinyl, quinazolinyl, quinoxalinyl, thiazolopyridinyl, oxazolopyridinyl or imidazo[2,1-b] thiazolyl; wherein said heterocycle may optionally be substituted with one, or where possible, two or three substituents each independently selected from $Het^4$, $R^{11}$ or $C_{1-4}$alkyl optionally substituted with one or two substituents independently selected from $Het^4$ or $R^{11}$;

$Het^3$ represents a monocyclic heterocycle selected from pyrrolidinyl, piperidinyl, piperazinyl, morpholinyl, thiomorpholinyl or tetrahydropyranyl; wherein said monocyclic heterocycle may optionally be substituted with, where possible, one, two, three or four substituents each independently selected from the group consisting of: hydroxy, $C_{1-4}$alkyl, $C_{1-4}$alkyloxy, $C_{1-4}$alkylcarbonyl, piperidinyl, $NR^{12}R^{13}$, C(=O)—Z—$R^{14}$, $R^6$ and $C_{1-4}$alkyl substituted with one or two substituents independently selected from hydroxy, $C_{1-4}$alkyloxy, phenyl, C(=O)—Z—$R^{14}$, —Y—$C_{1-4}$alkanediyl-C(=O)—Z—$R^{14}$, $R^6$ or $NR^{12}R^{13}$;

$Het^4$ represents a monocyclic heterocycle selected from pyrrolyl, imidazolyl, pyrazolyl, triazolyl, tetrazolyl, furanyl, thienyl, oxazolyl, isoxazolyl, thiazolyl, isothiazolyl, thiadiazolyl, oxadiazolyl, pyridinyl, pyrimidinyl, pyrazinyl, pyranyl, pyridazinyl and triazinyl; provided however that $R^2$ is other than $C_{1-6}$alkyloxycarbonyl$C_{1-6}$alkyl, aminocarbonyl; and $R^7$, $R^8$, $R^9$ and $R^{10}$ are other than aminocarbonyl, $C_{1-4}$alkylcarbonyloxy-$C_{1-4}$alkylcarbonyl, hydroxy $C_{1-4}$alkylcarbonyl, $C_{1-4}$alkyloxycarbonylcarbonyl C(=O)—O—$R^{14}$, $C_{1-4}$alkanediylC(=O)—O—$R^{14}$ and —Y—$C_{1-4}$alkanediylC(=O)—O—$R^{14}$; and $R^{12}$ and $R^{13}$ are other than $C_{1-4}$alkylcarbonyloxy-$C_{1-4}$alkylcarbonyl, hydroxy $C_{1-4}$alkylcarbonyl, $C_{1-4}$alkylcarbonylcarbonyl; and $R^{11}$ is other than $C(=O)-O-R^{14}$, $Y-C_{1-4}$alkanediyl $-C(=O)-OR^{14}$, $C(=O)NH_2$, $C(=O)NHC_{1-4}$alkyl or $C(=O)NHC_{3-7}$cycloalkyl; and $R^{14}$ is other than hydrogen, $C_{1-4}$alkyl, $C_{3-7}$cycloalkyl, aminocarbonylmethylene, mono- or di($C_{1-4}$alkyl) aminocarbonylmethylene in the event Z is 0; and $R^{15}$ and $R^{16}$ are other than aminocarbonyl, $C_{1-4}$alkylcarbonyloxy-$C_{1-4}$alkylcarbonyl, hydroxy $C_{1-4}$alkylcarbonyl or $C_{1-4}$alkyloxycarbonylcarbonyl; and Aryl is other than phenyl substituted with $C(=O)-O-R^{14}C(=O)NH_2$, $C(=O)NHC_{1-4}$alkyl, $C(=O)NHC_{3-7}$cycloalkyl and/or with $C_{1-4}$alkyl substituted with $C(=O)-O-R^{14}$ or $Y-C_{1-4}$alkanediyl $-C(=O)-O-R^{14}$; and $Het^3$ is other than a monocyclic heterocycle substituted with $C(=O)\cdot O-R^{14}$ and/or with $C_{1-4}$alkyl substituted with $C(=O)-O-R^{14}$ and/or $Y-C_{1-4}$alkanediyl $-(=O)-O-R^{14}$; and the compound of formula (I) contains at least one $-C(=O)-Z-R^{14}$ moiety.

3. A compound according to claim 1 having the formula

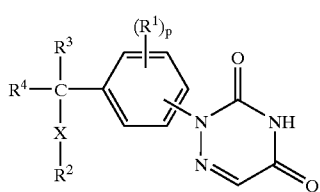

(I'')

a N-oxide, a pharmaceutically acceptable addition salt or a stereochemically isomeric form thereof, wherein:

p represents an integer being 0, 1, 2, 3 or 4;

X represents O, S, $NR^5$ or a direct bond or $-X-R^2$ taken together may represent cyano;

Y represents O, S, $NR^5$, or $S(O)_2$;

each $R^1$ independently represents $C(=O)\cdot Z-R^{14}$, $C_{1-6}$alkyl, halo, polyhalo$C_{1-6}$alkyl, hydroxy, mercapto, $C_{1-6}$alkyloxy, $C_{1-6}$alkylthio, $C_{1-6}$alkylcarbonyloxy, aryl, cyano, nitro, $Het^3$, $R^6$, $NR^7R^8$ or $C_{1-4}$alkyl substituted with $C(=O)-Z\cdot R^{14}$, $Het^3$, $R^6$ or $NR^7R^8$;

$R^2$ represents $Het^1$, $C_{3-7}$cycloalkyl optionally substituted with $C(=O)-Z-R^{14}$, $C_{1-6}$alkyl or $C_{1-6}$alkyl substituted with one or two substituents selected from the group consisting of: $C(=O)\cdot Z-R^{14}$, hydroxy, cyano, amino, mono- or di($C_{1-4}$alkyl)amino, $C_{1-6}$alkyloxy optionally substituted with $C(=O)-Z-R^{14}$, $C_{1-6}$alkylsulfonyloxy, $C_{3-7}$cycloalkyl optionally substituted with $C(=O)-Z-R^{14}$, aryl, aryloxy, arylthio, $Het^1$, $Het^1$oxy and $Het^1$thio; and if X is O, S or $NR^5$, then $R^2$ may also represent aminothiocarbonyl, $C_{1-4}$alkylcarbonyl optionally substituted with $C(=O)-Z-R^{14}$, $C_{1-4}$alkylthiocarbonyl optionally substituted with $C(=O)-Z-R^{14}$, arylcarbonyl, arylthiocarbonyl, $Het^1$carbonyl or $Het^1$thiocarbonyl;

$R^3$ represents hydrogen, $C_{1-6}$alkyl or $C_{3-7}$cycloalkyl;

$R^4$ represents hydrogen, $C_{1-6}$alkyl or $C_{3-7}$cycloalkyl; or $R^3$ and $R^4$ taken together form a $C_{2-6}$alkanediyl;

$R^5$ represents hydrogen or $C_{1-4}$alkyl;

each $R^6$ independently represents $C_{1-6}$alkylsulfonyl, aminosulfonyl, piperidinylsulfonyl, mono- or di($C_{1-4}$alkyl)aminosulfonyl, mono- or di(benzyl) aminosulfonyl, polyhalo$C_{1-6}$alkylsulfonyl, $C_{1-6}$alkylsulfinyl, phenyl$C_{1-4}$alkylsulfonyl, piperazinylsulfonyl, aminopiperidinylsulfonyl, piperidinylaminosulfonyl, $N-C_{1-4}$alkyl-N-piperidinylaminosulfonyl or mono- or di($C_{1-4}$alkyl) amino$C_{1-4}$alkylsulfonyl;

each $R^7$ and each $R^8$ are independently selected from the group consisting of: hydrogen, $C_{1-4}$alkyl, hydroxy$C_{1-4}$alkyl, dihydroxy$C_{1-4}$alkyl, aryl, aryl$C_{1-4}$alkyl, $C_{1-4}$alkyloxy$C_{1-4}$alkyl, $C_{1-4}$alkylcarbonyl, arylcarbonyl, $Het^3$carbonyl, mono- or di($C_{1-4}$alkyl) amino$C_{1-4}$alkyl, arylaminocarbonyl, arylaminothiocarbonyl, $Het^3$aminocarbonyl, $Het^3$aminothiocarbonyl, $C_{3-7}$cycloalkyl, pyridinyl$C_{1-4}$alkyl, $C_{1-4}$ alkanediyl-$C(=O)-Z-R^{14}$, $-C(=O)-Z-R^{14}$, $-Y-C_{1-4}$alkanediyl $-C(=O)-Z-R^{14}$, $Het^3$, $Het^4$ and $R^6$; or $R^7$ and $R^8$ taken together with the nitrogen atom to which they are attached form a radical of formula

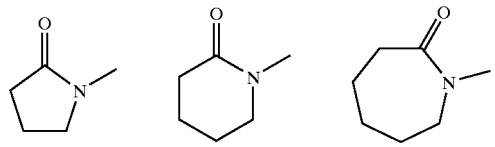

$R^9$ and $R^{10}$ are each independently selected from the group consisting of: hydrogen, $C_{1-4}$alkyl, hydroxy$C_{1-4}$alkyl, dihydroxy$C_{1-4}$alkyl, phenyl, phenyl$C_{1-4}$alkyl, $C_{1-4}$alkyloxy$C_{1-4}$alkyl, $C_{1-4}$alkylcarbonyl, phenylcarbonyl, $Het^3$carbonyl, mono- or di($C_{1-4}$alkyl) amino$C_{1-4}$alkyl, phenylaminocarbonyl, phenylaminothiocarbonyl, $Het^3$aminocarbonyl, $Het^3$aminothiocarbonyl, $C_{3-7}$cycloalkyl, pyridinyl$C_{1-4}$alkyl, $C_{1-4}$alkanediyl-$C(=O)-Z-R^{14}$, $-C(=O)-Z-R^{14}$, $-Y-C_{1-4}$alkanediyl-$C(=O)-Z-R^{14}$, $Het^3$, $Het^4$ and $R^8$; or $R^9$ and $R^{10}$ taken together with the nitrogen atom to which they are attached form a radical of formula

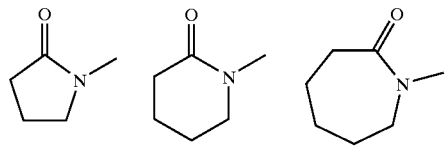

each $R^{11}$ independently being selected from the group consisting of: hydroxy, mercapto, cyano, nitro, halo, trihalomethyl, $C_{1-4}$alkyloxy optionally substituted with $C(=O)-Z-R^{14}$, formyl, trihalo$C_{1-4}$alkylsulfonyloxy, $R^6$, $NR^7R^8$, $C(=O)NR^{15}R^{16}$, $-C(=O)-Z-R^{14}$, $-Y-C_{1-4}$alkanediyl-$C(=O)-Z-R^{14}$, aryl, aryloxy, arylcarbonyl, $C_{3-7}$cycloalkyl optionally substituted with $C(=O)-Z-R^{14}$, $C_{3-7}$cycloalkyloxy optionally substituted with $C(=O)-Z-R^{14}$, phthalimide-2-yl, $Het^3$, $Het^4$ and $C(=O)Het^3$;

$R^{12}$ and $R^{13}$ are each independently selected from the group consisting of: hydrogen, $C_{1-4}$alkyl, hydroxy$C_{1-4}$alkyl, dihydroxy$C_{1-4}$alkyl, phenyl, phenyl$C_{1-4}$alkyl, $C_{1-4}$alkyloxy$C_{1-4}$alkyl, $C_{1-4}$alkylcarbonyl, phenylcarbonyl, mono- or di($C_{1-4}$alkyl)amino$C_{1-4}$alkyl, phenylaminocarbonyl, phenylaminothiocarbonyl, $C_{3-7}$cycloalkyl, pyridinyl$C_{1-4}$alkyl, $C_{1-4}$alkanediyl-$C(=O)-Z-R^{14}$, —C(=O)—Z—R$^{14}$, —Y—C$_{1-4}$alkanediyl-C(=O)—Z—R$^{14}$ and R$^6$; or R$^{12}$ and R$^{13}$ taken together with the nitrogen atom to which they are attached form a radical of formula

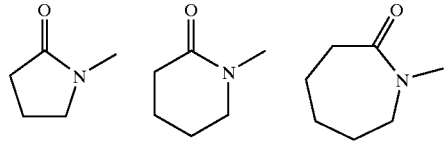

each R$^{14}$ independently represents hydrogen, C$_{1-20}$acyl (having a straight or branched, saturated or unsaturated hydrocarbon chain having 1 to 20 carbon atoms), C$_{1-20}$alkyl, C$_{3-20}$alkenyl optionally substituted with phenyl, C$_{3-20}$alkynyl, C$_{3-7}$cycloalkyl, polyhaloC$_{1-20}$alkyl, Het$^5$, phenyl or C$_{1-20}$alkyl substituted with one or more substituents selected from the group consisting of: hydroxy, NR$^{17}$R$^{18}$, phenyl, mono- or di-(C$_{1-4}$alkyl)amino, cyano, Het$^5$, C$_{1-4}$alkyloxycarbonyl, phenyl C$_{1-4}$alkyloxycarbonyl and C$_{3-7}$ cycloalkyl, or R$^{14}$ represents a radical of formula

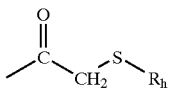 (a)

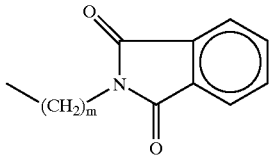 (b)

(c)

(d)

(e)

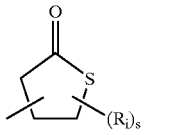 (h)

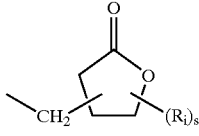 (i)

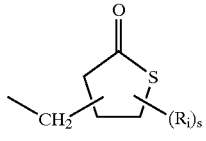 (j)

(k)

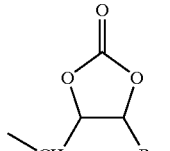 (l)

(m)

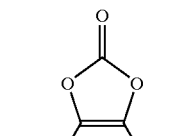 (n)

(o)

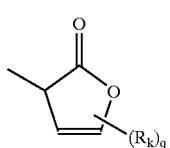 (p)

(q)

 (r)

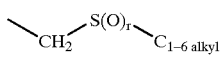 (s)

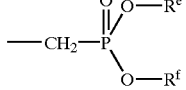 (t)

wherein m is 1 to 4, n is 0 to 5, q is 0 to 2, r is 0 to 2 and s is 0 to 4;

R$^a$, R$^b$, R$^c$, R$^d$, R$^e$ and R$^f$ are each independently hydrogen, C$_{1-6}$alkyl, phenyl or C$_{3-7}$cycloalkyl; or $R^e$ and $R^f$ taken together may form —CH$_2$—CH$_2$—, —CH$_2$—CH$_2$—CH$_2$— or —CH$_2$—CH$_2$—CH$_2$—CH$_2$—;

$R_g$, $R_h$ and $R_k$ are each independently hydrogen or $C_{1-4}$alkyl;

$R_i$ is $C_{1-4}$alkyl;

$R_j$ is —O—$R_b$, $C_{1-6}$alkyl, phenyl or $C_{3-7}$cycloalkyl optionally substituted with $C_{1-4}$ alkyloxy;

where $R_m$ is hydrogen or $C_{1-4}$ alkyloxy and $R_n$ is hydrogen, $C_{1-4}$alkyl, $C_{3-7}$cycloalkyl, phenyl or phenyl$C_{1-4}$alkyl each Z independently represents O, S, NH, —CH$_2$—O— or —CH$_2$—S— whereby —CH$_2$— is attached to the carbonyl group; or —Z—$R^{14}$ taken together form a radical of formula

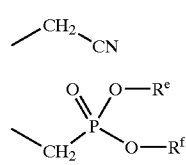

(f)

(g)

$R^{15}$ and $R^{16}$ are each independently selected from hydrogen, $C_{1-4}$alkyl, hydroxy$C_{1-4}$alkyl, dihydroxy$C_{1-4}$alkyl, aryl, aryl$C_{1-4}$alkyl, $C_{1-4}$alkyloxy$C_{1-4}$alkyl, —C(=O)—Z—$R^{14}$, arylcarbonyl, mono- or di($C_{1-4}$alkyl)amino$C_{1-4}$alkyl, arylaminocarbonyl, arylaminothiocarbonyl, aminocarbonylmethylene, mono- or di($C_{1-4}$alkyl) aminocarbonylmethylene, Het$^3$aminocarbonyl, Het$^3$aminothiocarbonyl, pyridinyl$C_{1-4}$alkyl, Het$^3$ or $R^6$; or $R^{15}$ and $R^{16}$ taken together with the nitrogen atom to which they are attached form a radical of formula

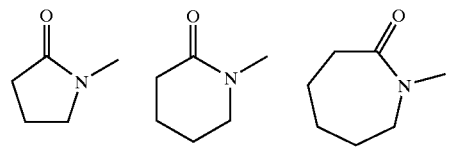

$R^{17}$ and $R^{18}$ are each independently selected from the group consisting of: hydrogen, $C_{1-4}$alkyl, hydroxy$C_{1-4}$alkyl, dihydroxy$C_{1-4}$alkyl, phenyl, phenyl$C_{1-4}$alkyl, $C_{1-4}$alkyloxy$C_{1-4}$alkyl, $C_{1-4}$alkylcarbonyl, phenylcarbonyl, mono- or di($C_{1-4}$alkyl)amino$C_{1-4}$alkyl, phenylaminocarbonyl, phenylaminothiocarbonyl, $C_{3-7}$cycloalkyl, pyridinyl$C_{1-4}$alkyl, $C_{1-4}$alkanediyl-C(=O)—Z—$C_{1-6}$alkyl, —C(=O)—Z—$C_{1-6}$alkyl, —Y—$C_{1-4}$alkanediyl-C(=O)—Z—$C_{1-6}$alkyl and $R^6$;

aryl represents phenyl optionally substituted with one, two or three substituents each independently selected from the group consisting of: nitro, azido, cyano, halo, hydroxy, $C_{1-4}$alkyl, $C_{3-7}$cycloalkyl, $C_{1-4}$alkyloxy, formyl, polyhalo$C_{1-4}$alkyl, NR$^9$R$^{10}$, C(=O)NR$^9$R$^{10}$, C(=O)—Z—$R^{14}$, $R^6$, —O—$R^6$, phenyl, Het$^3$, C(=O)Het$^3$ and $C_{1-4}$alkyl substituted with one or more substituents each independently selected from halo, hydroxy, $C_{1-4}$alkyloxy, C(=O)—Z—$R^{14}$, —Y—$C_{1-4}$alkanendiyl-C(=O)—Z—$R^{14}$, Het$^3$ or NR$^9$R$^{10}$;

Het$^1$ represents a heterocycle selected from pyrrolyl, pyrrolinyl, imidazolyl, imidazolinyl, pyrazolyl, pyrazolinyl, triazolyl, tetrazolyl, furanyl, tetrahydrofuranyl, thienyl, thiolanyl, dioxolanyl, oxazolyl, oxazolinyl, isoxazolyl, thiazolyl, thiazolinyl, isothiazolyl, thiadiazolyl, oxadiazolyl, pyridinyl, pyrimidinyl, pyrazinyl, pyranyl, pyridazinyl, pyrrolidinyl, piperidinyl, piperazinyl, morpholinyl, thiomorpholinyl, dioxanyl, dithianyl, trithianyl, triazinyl, benzothienyl, isobenzothienyl, benzofuranyl, isobenzofuranyl, benzothiazolyl, benzoxazolyl, benzodioxanyl, indolyl, isoindolyl, indolinyl, purinyl, 1H-pyrazolo[3,4-d]pyrimidinyl, benzimidazolyl, quinolyl, isoquinolyl, cinnolinyl, phtalazinyl, quinazolinyl, quinoxalinyl, thiazolopyridinyl, oxazolopyridinyl or imidazo[2,1-b]thiazolyl; wherein said heterocycle may optionally be substituted with one, or where possible, two or three substituents each independently selected from Het$^2$, $R^{11}$ or $C_{1-4}$alkyl optionally substituted with one or two substituents independently selected from Het$^2$ or $R^{11}$;

Het$^2$ represents a heterocycle selected from pyrrolyl, pyrrolinyl, imidazolyl, imidazolinyl, pyrazolyl, pyrazolinyl, triazolyl, tetrazolyl, furanyl, tetrahydrofuranyl, thienyl, thiolanyl, dioxolanyl, oxazolyl, oxazolinyl, isoxazolyl, thiazolyl, thiazolinyl, isothiazolyl, thiadiazolyl, oxadiazolyl, pyridinyl, pyrimidinyl, pyrazinyl, pyranyl, pyridazinyl, dioxanyl, dithianyl, trithianyl, triazinyl, benzothienyl, isobenzothienyl, benzofuranyl, isobenzofuranyl, benzothiazolyl, benzoxazolyl, indolyl, isoindolyl, indolinyl, purinyl, 1H-pyrazolo[3,4-d]pyrimidinyl, benzimidazolyl, quinolyl, isoquinolyl, cinnolinyl, phtalazinyl, quinazolinyl, quinoxalinyl, thiazolopyridinyl, oxazolopyridinyl or imidazo[2,1-b]thiazolyl; wherein said heterocycle may optionally be substituted with one, or where possible, two or three substituents each independently selected from Het$^4$, $R^{11}$ or $C_{1-4}$alkyl optionally substituted with one or two substituents independently selected from Het$^4$ or $R^{11}$;

Het$^3$ represents a monocyclic heterocycle selected from pyrrolidinyl, piperidinyl, piperazinyl, morpholinyl, thiomorpholinyl or tetrahydropyranyl; wherein said monocyclic heterocycle may optionally be substituted with, where possible, one, two, three or four substituents each independently selected from the group consisting of: hydroxy, $C_{1-4}$alkyl, $C_{1-4}$alkyloxy, $C_{1-4}$alkylcarbonyl, piperidinyl, NR$^{12}$R$^{13}$, C(=O)—Z—$R^{14}$, $R^6$ and $C_{1-4}$alkyl substituted with one or two substituents independently selected from hydroxy, $C_{1-4}$alkyloxy, phenyl, C(=O)—Z—$R^{14}$, —Y—$C_{1-4}$alkanediyl-C(=O)—Z—$R^{14}$, $R^6$ or NR$^{12}$R$^{13}$;

Het$^4$ represents a monocyclic heterocycle selected from pyrrolyl, imidazolyl, pyrazolyl, triazolyl, tetrazolyl, furanyl, thienyl, oxazolyl, isoxazolyl, thiazolyl, isothiazolyl, thiadiazolyl, oxadiazolyl, pyridinyl, pyrimidinyl, pyrazinyl, pyranyl, pyridazinyl or triazinyl;

Het$^5$ represents a heterocycle selected from pyrrolyl, pyrrolinyl, imidazolyl, imidazolinyl, pyrazolyl, pyrazolinyl, triazolyl, tetrazolyl, furanyl, tetrahydrofuranyl, thienyl, thiolanyl, dioxolanyl, oxazolyl, oxazolinyl, isoxazolyl, thiazolyl, thiazolinyl, isothiazolyl, thiadiazolyl, oxadiazolyl, pyridinyl, pyrimidinyl, pyrazinyl, pyranyl, pyridazinyl, pyrrolidinyl, piperidinyl, piperazinyl, morpholinyl, thiomorpholinyl, tetrahydropyranyl, dioxanyl, dithianyl, trithianyl, triazinyl, benzothienyl, isobenzothienyl, benzofuranyl, isobenzofuranyl, benzothiazolyl, benzoxazolyl, benzodioxanyl, indolyl, isoindolyl, indolinyl, purinyl, 1H-pyrazolo[3,4-d]pyrimidinyl, benzimidazolyl, quinolyl, isoquinolyl, cinnolinyl, phtalazinyl, quinazolinyl, quinoxalinyl, thiazolopyridinyl, oxazolopyridinyl or imidazo[2,1-b]thiazolyl; wherein said heterocycle may be substituted with, where possible, one, two, three or four substituents each independently selected from the group consisting of: hydroxy, $C_{1-4}$alkyl, $C_{1-4}$alkyloxy, $C_{1-4}$alkylcarbonyl, piperidinyl, $NR^{17}NR^{18}$, $C(=O)$—Z—$C_{1-6}$alkyl, $R^6$, sulfonamido and $C_{1-4}$alkyl substituted with one or two substituents independently selected from hydroxy, $C_{1-4}$alkyloxy, phenyl, $C(=O)$—Z—$C_{1-6}$alkyl, —Y—$C_{1-4}$alkanediyl-C(=O)—Z—$C_{1-6}$alkyl, $R^6$ or $NR^{17}R^{18}$; provided however that $R^2$ is other than $C_{1-6}$ alkyloxycarbonyl$C_{1-6}$alkyl or aminocarbonyl; and $R^7$, $R^8$, $R^9$ and $R^{10}$ are other than aminocarbonyl, $C_{1-4}$alkylcarbonyloxy-$C_{1-4}$alkylcarbonyl, hydroxy $C_{1-4}$alkylcarbonyl, $C_{1-4}$alkyloxycarbonylcarbonyl, $C(=O)$—O—$R^{19}$, $C_{1-4}$alkanediyl$C(=O)$—O—$R^{19}$ or —Y—$C_{1-4}$alkanediyl$C(=O)$—O—$R^{19}$; and $R^{12}$ and $R^{13}$ are other than $C_{1-4}$alkylcarbonyloxy-$C_{1-4}$alkylcarbonyl, hydroxy $C_{1-4}$alkylcarbonyl or $C_{1-4}$alkylcarbonylcarbonyl; and $R^{11}$ is other than $C(=O)$—O—$R^{19}$, Y—$C_{1-4}$alkanediyl—$C(=O)$—OR$^{19}$, $C(=O)NH_2$, $C(=O)NHC_{1-4}$alkyl or $C(=O)NHC_{3-7}$cycloalkyl; and $R^{15}$ and $R^{16}$ are other than aminocarbonyl, $C_{1-4}$alkylcarbonyloxy-$C_{1-4}$alkylcarbonyl, hydroxy $C_{1-4}$alkylcarbonyl or $C_{1-4}$alkyloxycarbonylcarbonyl; and aryl is other than phenyl substituted with $C(=O)$—O—$R^{19}$, $C(=O)NH_2$, $C(=O)NHC_{1-4}$alkyl, $C(=O)NHC_{3-7}$cycloalkyl and/or with $C_{1-4}$alkyl substituted with $C(=O)$—O—$R^{19}$ or Y—$C_{1-4}$alkanediyl—$C(=O)$—O—$R^{14}$; and Het$^3$ is other than a monocyclic heterocycle substituted with $C(=O)\cdot O$—$R^{19}$ and/or with $C_{1-4}$alkyl subsituted with $C(=O)$—O—$R^{19}$ and/or Y—$C_{1-4}$alkanediyl —$(=O)$—O—$R^{19}$; and in each of the above proviso's $R^{19}$ is defined as hydrogen, $C_{1-4}$alkyl, $C_{3-7}$cycloalkyl, aminocarbonylmethylene or mono- or di($C_{1-4}$alkyl) aminocarbonylmethylene; and the said compound of formula (I) contains at least one —$C(=O)$—Z—$R^{14}$ moiety.

4. A compound according to claim 1 wherein the 6-azauracil moiety is in the pare position relative to the carbon atom bearing the —X—$R^2$, $R^3$ and $R^4$ substituents.

5. A compound according to claim 1 wherein $R^2$ is a monocyclic heterocycle selected from the group consisting of: pyrrolyl, imidazolyl, pyrazolyl, triazolyl, tetrazolyl, furanyl, thienyl, oxazolyl, isoxazolyl, thiazolyl, isothiazolyl, thiadiazolyl, oxadiazolyl, pyridinyl, pyrimidinyl, pyrazinyl, pyranyl, pyridazinyl and triazinyl, wherein said monocyclic heterocycle may optionally be substituted with one, or where possible, two or three substituents each independently selected from Het$^2$, $R^{11}$ or $C_{1-4}$alkyl optionally substituted with Het$^2$ or $R^{11}$.

6. A compound according to claim 1 wherein $R^3$ and $R^4$ are both methyl and —X—$R^2$ is Het$^1$.

7. A compound according to claim 1 wherein p is 1 or 2 and each $R^1$ is chloro.

8. A compound according to claim 1 wherein $R^3$ and $R^4$ are both methyl, —X—$R^2$ is optionally substituted 2-thiazolyl or 3-oxadiazolyl, the 6-azauracil moiety is in the para position relative to the carbon atom bearing the —X—$R^2$, $R^3$ and $R^4$ substituents, and p is 2 whereby both $R^1$ substituents are chloro positioned ortho relative to the carbon atom bearing the —X—$R^2$, $R^3$ and $R^4$ substituents.

9. A compound according to claim 8 wherein X—$R^2$ is di-substituted with phenyl and either (i) $R^{11}$ where $R^{11}$ is a group of formula —$C(=O)$—Z—$R^{14}$ in which Z is O and $R^{14}$ is $C_{1-20}$alkyl substituted with hydroxy or with Het$^5$ where Het$^5$ is piperazinyl substituted with Het$^6$sulfonyl, or $R^{14}$ is a radical of formula (a) in which $R_j$ is $C_{1-6}$alkyl and s is 2, or (ii) $C_{1-4}$alkyl substituted with $R^{11}$ where $R^{11}$ is a a group of formula —$C(=O)$—Z—$R^{14}$ in which Z is O and $R^{14}$ is a radical of formula (a) in which $R_j$ is $C_{1-6}$alkyl and s is 2.

10. A compound selected from the group consisting of formulae (A), (B), (C) and (D) below:

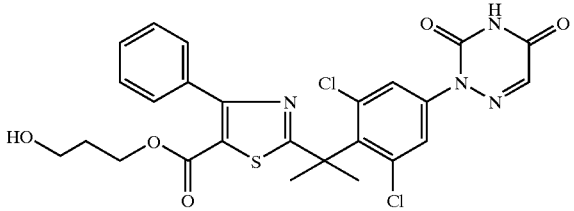

(A)

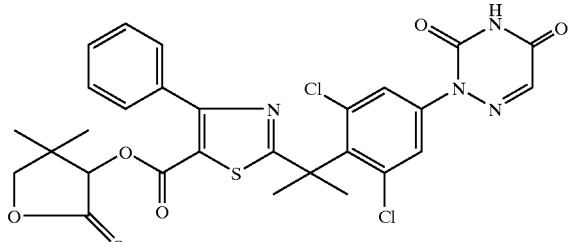

(B)

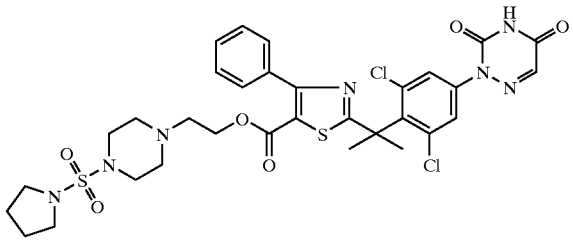

(C)

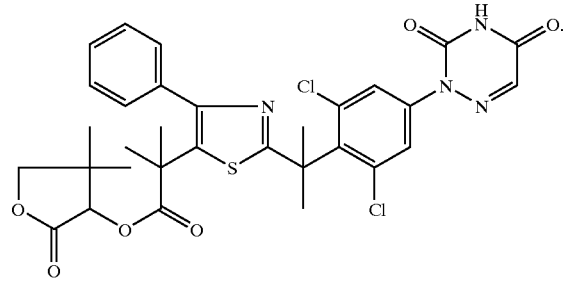

(D)

11. A composition comprising a pharmaceutically acceptable carrier and, as active ingredient, a therapeutically effective amount of a compound according to claim 1.

12. A method for treating eosinophil-dependent inflammatory diseases comprising administering to a subject in need thereof an effective amount of a compound of claim 1.

13. A process for preparing a compound as claimed in claim 1, comprising the step of a) reacting an intermediate of formula (II) wherein $W^1$ is a suitable leaving group with an appropriate reagent of formula (III) optionally in a reaction-inert solvent and optionally in the presence of a base at a temperature ranging between −70° C. and reflux temperature;

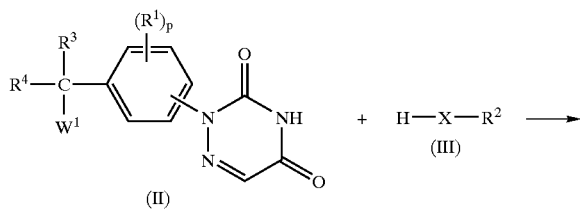

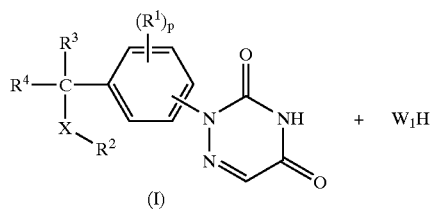

wherein $R^1$, $R^2$, $R^3$, $R^4$, p and X are as defined in claim 1 or;

b) eliminating the group E of a triazinedione of formula (V)

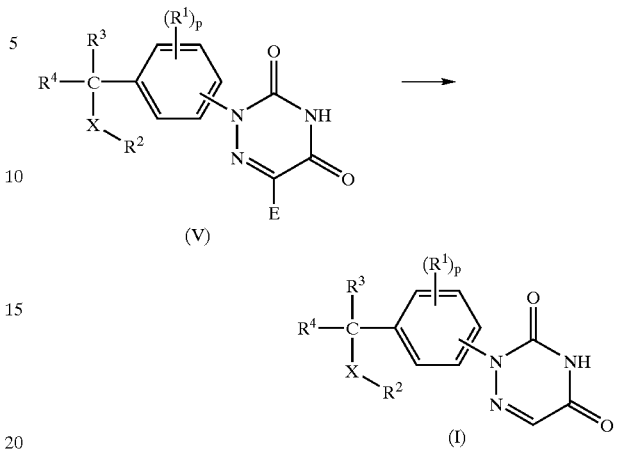

wherein E is an appropriate electron attracting group and $R^1$, $R^2$, $R^3$, $R^4$, X and p are as defined in claim 1; and, if desired, converting compounds of formula (I) into each other following art-known transformations, and further, if desired, converting the compounds of formula (I), into a therapeutically active non-toxic acid addition salt by treatment with an acid, or into a therapeutically active non-toxic base addition salt by treatment with a base, or conversely, converting the acid addition salt form into the free base by treatment with alkali, or converting the base addition salt into the free acid by treatment with acid; and also, if desired, preparing stereochemically isomeric forms or N-oxide forms thereof.

* * * * *